(12) United States Patent
Deckman et al.

(10) Patent No.: US 10,028,858 B2
(45) Date of Patent: Jul. 24, 2018

(54) INTRAUTERINE SYSTEMS, IUD INSERTION DEVICES, AND RELATED METHODS AND KITS THEREFOR

(75) Inventors: Rob Deckman, San Bruno, CA (US); Richard E. Repp, San Jose, CA (US); Curt Guyer, Dublin, CA (US); Justin Westendorf, Santa Clara, CA (US); Timothy Parmer, Brooklyn Park, MN (US)

(73) Assignee: Medicines360, San Francisco, CA (US)

( * ) Notice: Subject to any disclaimer, the term of this patent is extended or adjusted under 35 U.S.C. 154(b) by 628 days.

(21) Appl. No.: 13/539,843

(22) Filed: Jul. 2, 2012

(65) Prior Publication Data

US 2013/0014762 A1 Jan. 17, 2013

Related U.S. Application Data

(60) Provisional application No. 61/506,434, filed on Jul. 11, 2011.

(51) Int. Cl.
| | | |
|---|---|---|
| *A61F 6/18* | (2006.01) | |
| *A61F 6/14* | (2006.01) | |
| *A61F 6/12* | (2006.01) | |

(52) U.S. Cl.
CPC ............. *A61F 6/144* (2013.01); *A61F 6/18* (2013.01); *A61F 6/12* (2013.01)

(58) Field of Classification Search
CPC ...... A61F 6/00; A61F 6/06; A61F 6/12; A61F 6/14; A61F 6/142; A61F 6/144; A61F 6/18; A61F 2/2436; A61F 2/95; A61F 2/962; A61F 2/966; A61F 2/97; A61F 6/22; A61F 6/225; A61F 6/24; A61K 9/0039; A61B 14/4241; A61B 17/3207; A61B 2017/291; A61B 1/00002; A61B 1/00064; A61B 1/00066; A61B 1/00073; A61B 1/00121; A61B 1/00135; A61B 1/00137; A61B 1/0014; A61B 1/00142; A61B 1/00147; A61B 1/0052; A61B 1/303; A61B 1/307; A61B 1/31; A61B 1/00101;
(Continued)

(56) References Cited

U.S. PATENT DOCUMENTS

| 3,230,953 A | 1/1966 | Bimberg et al. |
| 3,253,590 A | 5/1966 | Bimberg et al. |

(Continued)

FOREIGN PATENT DOCUMENTS

| AU | 2015221468 B2 | 12/2017 |
| CA | 2163762 A1 | 12/1994 |

(Continued)

*Primary Examiner* — Alireza Nia
*Assistant Examiner* — Rachel Berezik
(74) *Attorney, Agent, or Firm* — Shartsis Friese LLP; Cecily Anne O'Regan

(57) ABSTRACT

Intrauterine systems and components thereof. The systems include an intrauterine device (IUD), an insertion device or applicator for inserting the IUD into the cervix of a female patient. The insertion device includes an elongated sheath; an elongated inner member positioned within a lumen of the elongated sheath; a handle with one or more elongated guides; and a moveable sheath slider. Additionally, methods related to the insertion procedure, and methods of manufacture for the insertion device.

26 Claims, 44 Drawing Sheets

(58) Field of Classification Search
CPC ............ A61B 1/00098; A61B 1/00105; A61B 1/00112; A61B 1/00149; A61B 1/01; A61B 1/012; A61B 1/0125; A61B 1/00131; A61M 25/0015; A61M 25/0014; A61M 25/0028; A61M 25/0029; A61M 25/003; A61M 25/005; A61M 25/01; A61M 25/0138; A61M 25/0147; A61M 25/09016; A61M 25/09025; A61M 25/0102; A61M 25/0105; A61M 25/0152; A61M 25/1025; A61M 2025/0059; A61M 2025/015; A61M 2025/0175; A61M 2025/0004; A61M 2025/0006; A61M 2025/0024; A61M 2025/0034; A61M 2025/0031; A61M 2025/0177

See application file for complete search history.

(56) References Cited

U.S. PATENT DOCUMENTS

| | | | |
|---|---|---|---|
| 3,407,806 A | 10/1968 | Hulka et al. | |
| 3,467,088 A | 9/1969 | Robinson | |
| 3,577,987 A | 5/1971 | Bronnenkant | |
| 3,783,861 A | 1/1974 | Abramson | |
| 3,794,025 A | 2/1974 | Lerner | |
| 3,902,483 A | 9/1975 | Place et al. | |
| 3,918,444 A | 11/1975 | Hoff et al. | |
| 3,937,217 A | 2/1976 | Kosonen | |
| 4,353,363 A | 10/1982 | Sopena | |
| 4,359,046 A | 11/1982 | Shaw | |
| 4,361,150 A * | 11/1982 | Voss | 604/15 |
| 4,372,302 A | 2/1983 | Akerlund | |
| 4,381,001 A | 4/1983 | Shaw, Jr. | |
| 4,381,011 A | 4/1983 | Shaw | |
| 4,495,934 A | 1/1985 | Shaw | |
| 4,830,025 A | 6/1989 | Gainutdinova et al. | |
| 4,920,727 A | 5/1990 | Ristimaki et al. | |
| 4,949,732 A | 8/1990 | Spoon et al. | |
| 4,957,119 A | 9/1990 | De Nijs | |
| 5,084,004 A | 1/1992 | Ranoux | |
| 5,088,505 A | 2/1992 | De Nijs | |
| 5,370,129 A * | 12/1994 | Diaz et al. | 128/839 |
| 5,400,804 A | 5/1995 | Helle et al. | |
| RE35,636 E | 10/1997 | Diaz et al. | |
| 5,785,053 A * | 7/1998 | Macandrew et al. | 128/840 |
| 6,039,968 A | 3/2000 | Nabahi | |
| 6,056,976 A | 5/2000 | Makkula et al. | |
| 6,063,395 A | 5/2000 | Markkula et al. | |
| 6,103,256 A | 8/2000 | Nabahi | |
| 6,117,442 A | 9/2000 | Markkula et al. | |
| 6,414,151 B1 | 7/2002 | Matson et al. | |
| 6,588,429 B1 | 7/2003 | Wildemeersch | |
| 6,794,464 B2 | 9/2004 | Jukarainen et al. | |
| 6,887,948 B2 | 5/2005 | Jukarainen et al. | |
| 7,591,268 B2 | 9/2009 | Lowe et al. | |
| D603,038 S | 10/2009 | Kortesuo et al. | |
| 7,661,429 B2 | 2/2010 | Jutila | |
| D612,931 S | 3/2010 | Kortesuo et al. | |
| 7,862,552 B2 | 1/2011 | McIntyre et al. | |
| 8,381,733 B2 | 2/2013 | Lowe et al. | |
| 8,679,103 B2 | 3/2014 | Krespi | |
| 8,726,906 B2 | 5/2014 | Lee-Sepsick et al. | |
| 8,733,360 B2 | 5/2014 | Nikolchev et al. | |
| 8,733,361 B2 | 5/2014 | Nikolchev et al. | |
| D718,435 S | 11/2014 | Deckman et al. | |
| 9,668,912 B2 | 6/2017 | Jutila et al. | |
| 2003/0028236 A1 * | 2/2003 | Gillick et al. | 623/1.11 |
| 2004/0163650 A1 * | 8/2004 | Lowe et al. | 128/830 |
| 2005/0045183 A1 | 3/2005 | Callister et al. | |
| 2007/0009564 A1 | 1/2007 | McClain et al. | |
| 2008/0095825 A1 | 4/2008 | Lafront | |
| 2008/0147182 A1 * | 6/2008 | Righini et al. | 623/2.11 |
| 2009/0069890 A1 * | 3/2009 | Suri et al. | 623/2.11 |
| 2009/0105794 A1 * | 4/2009 | Ziarno et al. | 607/120 |
| 2009/0123522 A1 | 5/2009 | Browing | |
| 2009/0270835 A1 | 10/2009 | Kushner | |
| 2010/0015200 A1 | 1/2010 | McClain | |
| 2010/0049313 A1 * | 2/2010 | Alon et al. | 623/2.11 |
| 2010/0168756 A1 * | 7/2010 | Dorn et al. | 606/108 |
| 2011/0061659 A1 * | 3/2011 | Cruzada et al. | 128/831 |
| 2011/0079226 A1 * | 4/2011 | Sakhel | 128/830 |
| 2011/0162656 A1 * | 7/2011 | Jutila et al. | 128/830 |
| 2011/0166508 A1 * | 7/2011 | Lyytikainen et al. | 604/48 |
| 2011/0238147 A1 * | 9/2011 | Bennett et al. | 623/1.11 |
| 2011/0251679 A1 * | 10/2011 | Wiemeyer et al. | 623/2.11 |
| 2012/0143209 A1 * | 6/2012 | Brecheen et al. | 606/119 |
| 2012/0247481 A1 * | 10/2012 | Sakhel | 128/830 |
| 2013/0152942 A1 | 6/2013 | Jutila et al. | |
| 2013/0213406 A1 | 8/2013 | Frankenne et al. | |
| 2017/0273820 A1 | 9/2017 | Deckman et al. | |

FOREIGN PATENT DOCUMENTS

| | | |
|---|---|---|
| CN | 104023681 A | 9/2014 |
| DE | 19815552 C1 | 9/1999 |
| EP | 0455767 B1 | 1/1995 |
| JP | 10510444 A | 10/1998 |
| JP | 2014523780 A | 9/2014 |
| WO | WO1988-04544 A1 | 6/1988 |
| WO | WO1990-02478 A1 | 3/1990 |
| WO | WO1991-07934 A1 | 6/1991 |
| WO | WO1992-07590 A1 | 5/1992 |
| WO | WO1993-00055 A1 | 1/1993 |
| WO | WO1993-20797 A1 | 10/1993 |
| WO | WO1994-04109 A1 | 3/1994 |
| WO | WO1995-09006 A1 | 4/1995 |
| WO | 9618365 A1 | 6/1996 |
| WO | WO1996-18365 A1 | 6/1996 |
| WO | WO1996-40259 A2 | 12/1996 |
| WO | WO1997-39743 A1 | 10/1997 |
| WO | WO1999-02141 A1 | 1/1999 |
| WO | WO2000-45797 A1 | 2/2000 |
| WO | WO2001-37770 A1 | 5/2001 |
| WO | WO2001-85132 A1 | 11/2001 |
| WO | WO2002-43806 A2 | 6/2002 |
| WO | WO2002-079778 A2 | 10/2002 |
| WO | WO2003-017971 A1 | 3/2003 |
| WO | WO2003-018102 A2 | 3/2003 |
| WO | WO2005-000161 A2 | 1/2005 |
| WO | WO2008-023389 A1 | 2/2008 |
| WO | WO2008-081175 A2 | 7/2008 |
| WO | WO2009-002542 A1 | 12/2008 |
| WO | WO2009-101412 A1 | 8/2009 |
| WO | WO2010-000943 A1 | 1/2010 |
| WO | 2010031899 A1 | 3/2010 |
| WO | 2010031902 A1 | 3/2010 |
| WO | WO2010-031900 A1 | 3/2010 |
| WO | 2011034755 A2 | 3/2011 |
| WO | 2013009674 A3 | 1/2013 |
| WO | 2015036465 A1 | 3/2015 |
| WO | 2017165602 A1 | 9/2017 |

* cited by examiner

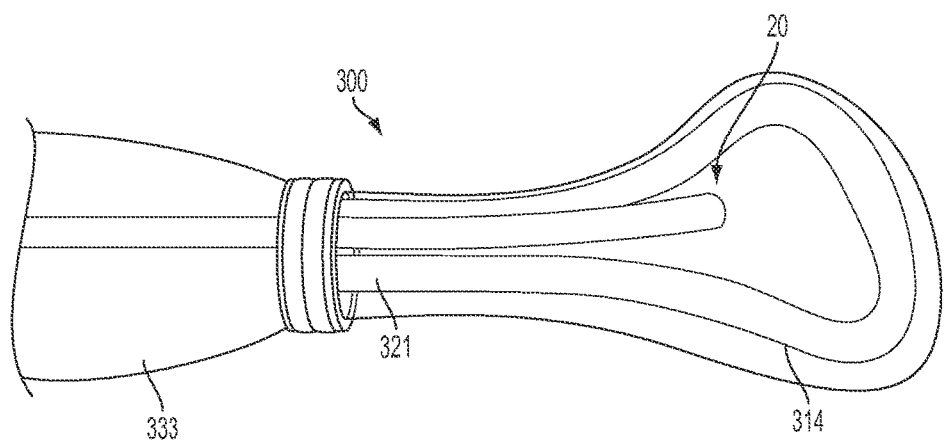
FIG. 3A
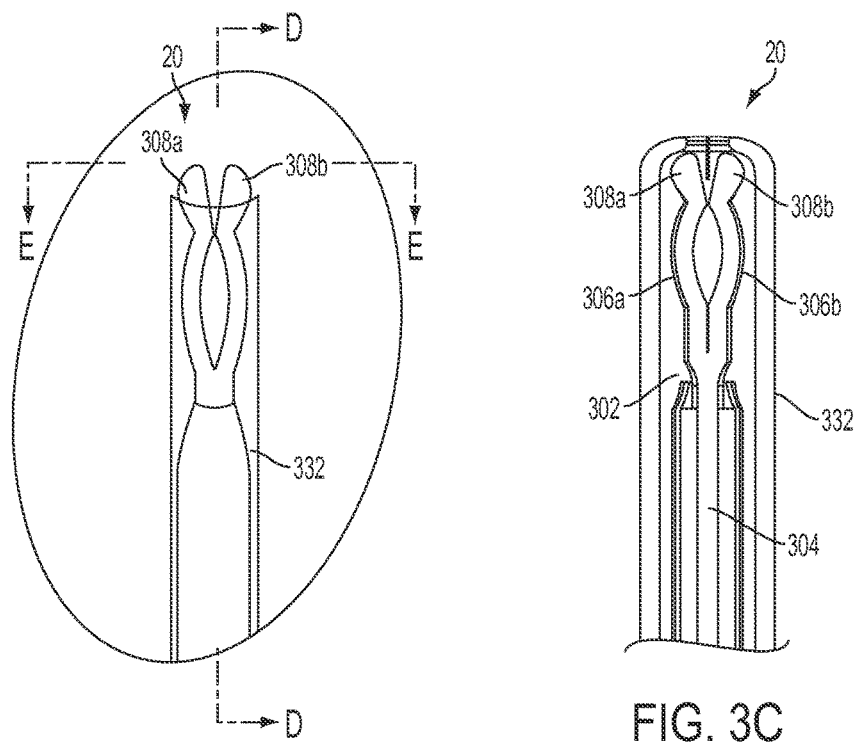
FIG. 3B
FIG. 3C

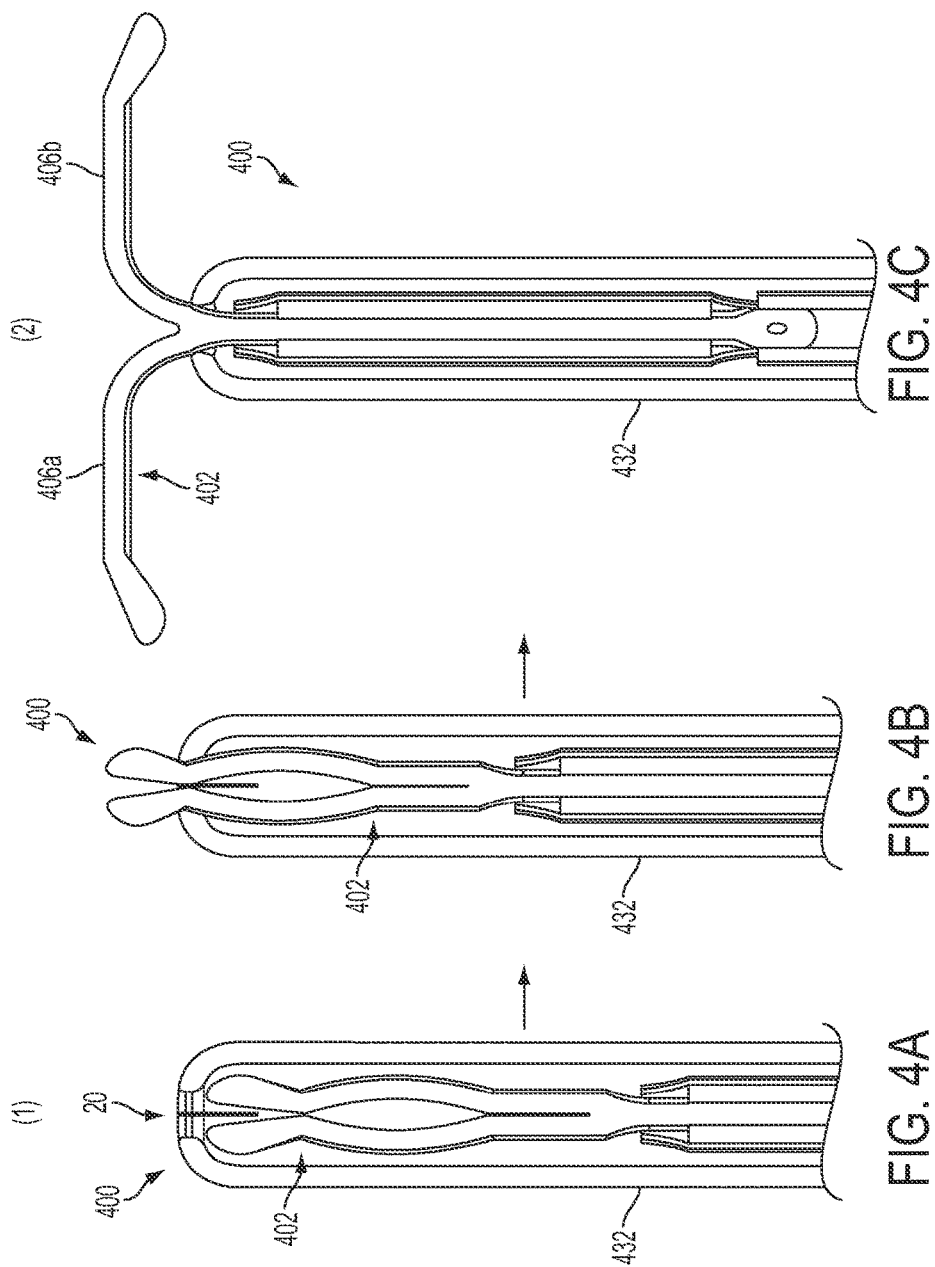

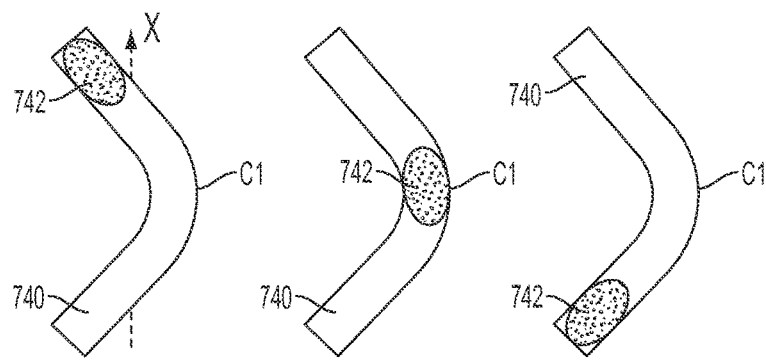
FIG. 7A(1)   FIG. 7A(2)   FIG. 7A(3)
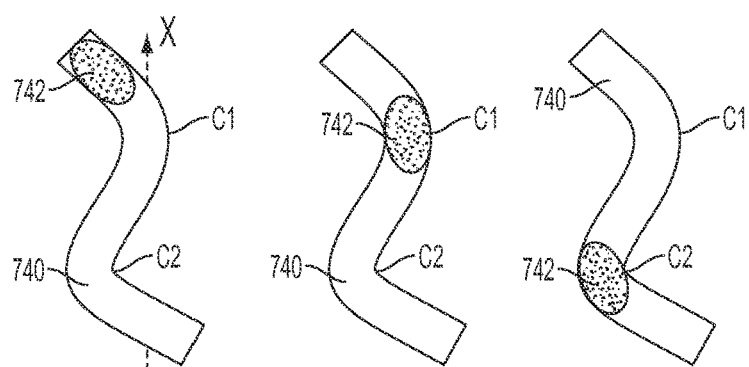
FIG. 7B(1)   FIG. 7B(2)   FIG. 7B(3)
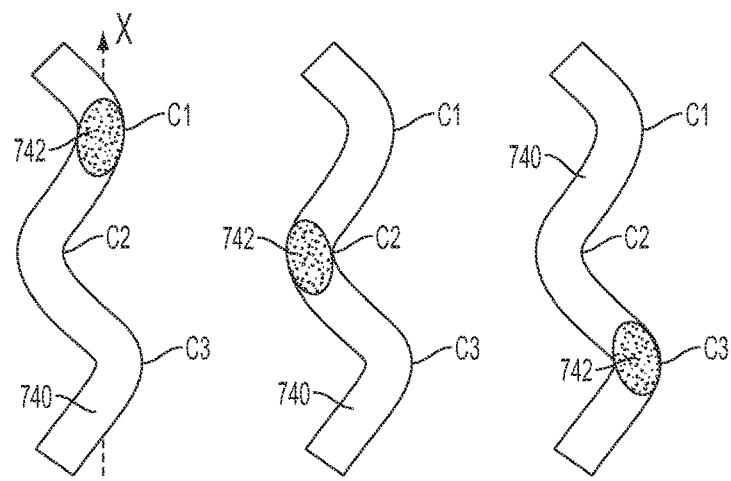
FIG. 7C(1)   FIG. 7C(2)   FIG. 7C(3)

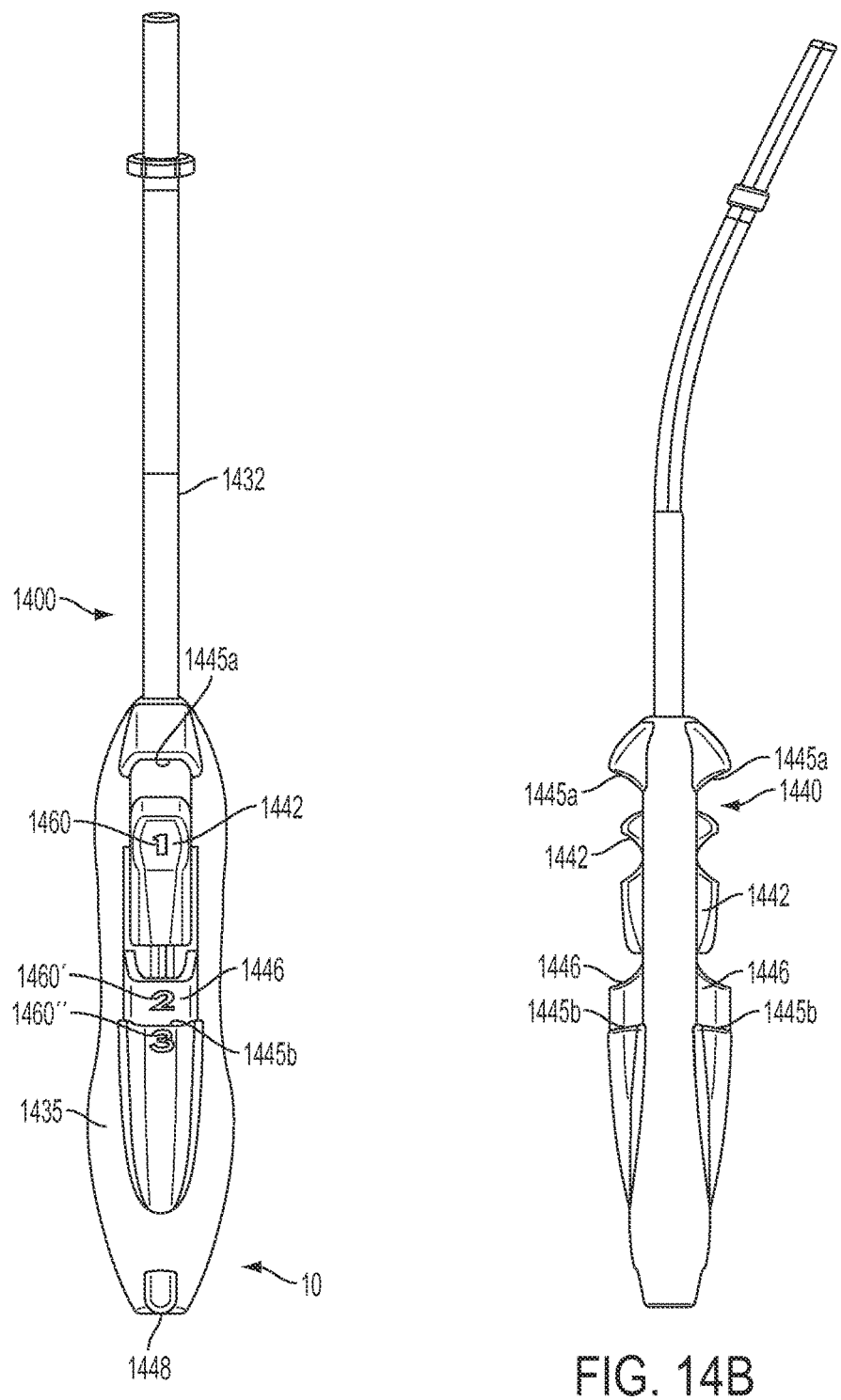

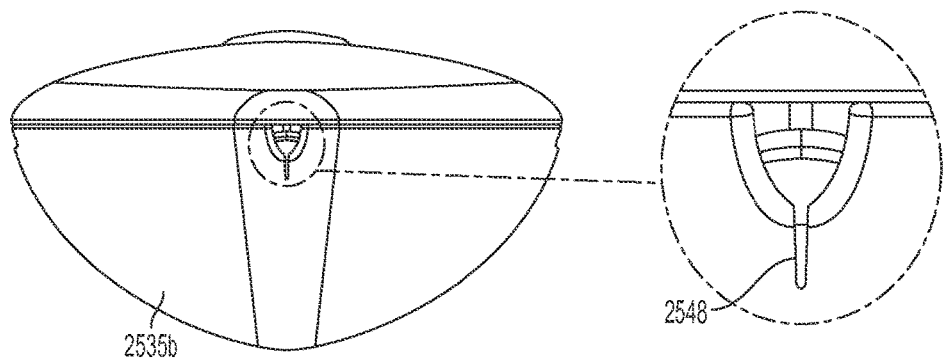
FIG. 25A
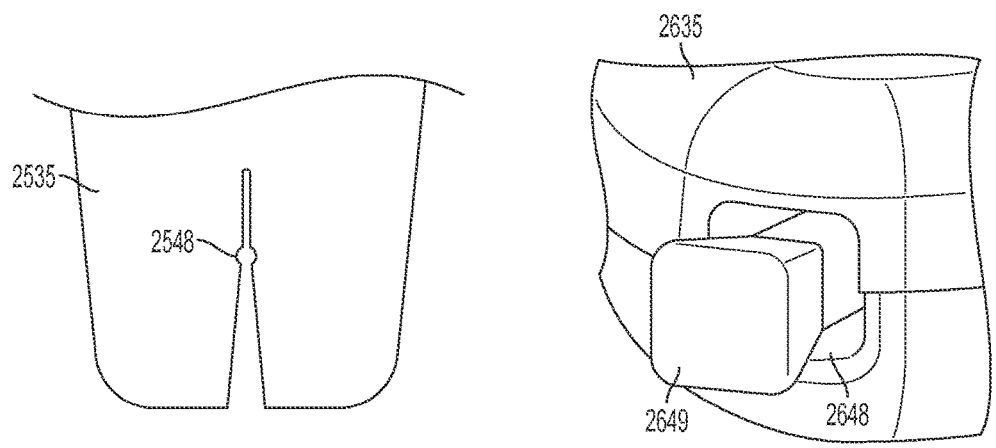
FIG. 25B
FIG. 26A

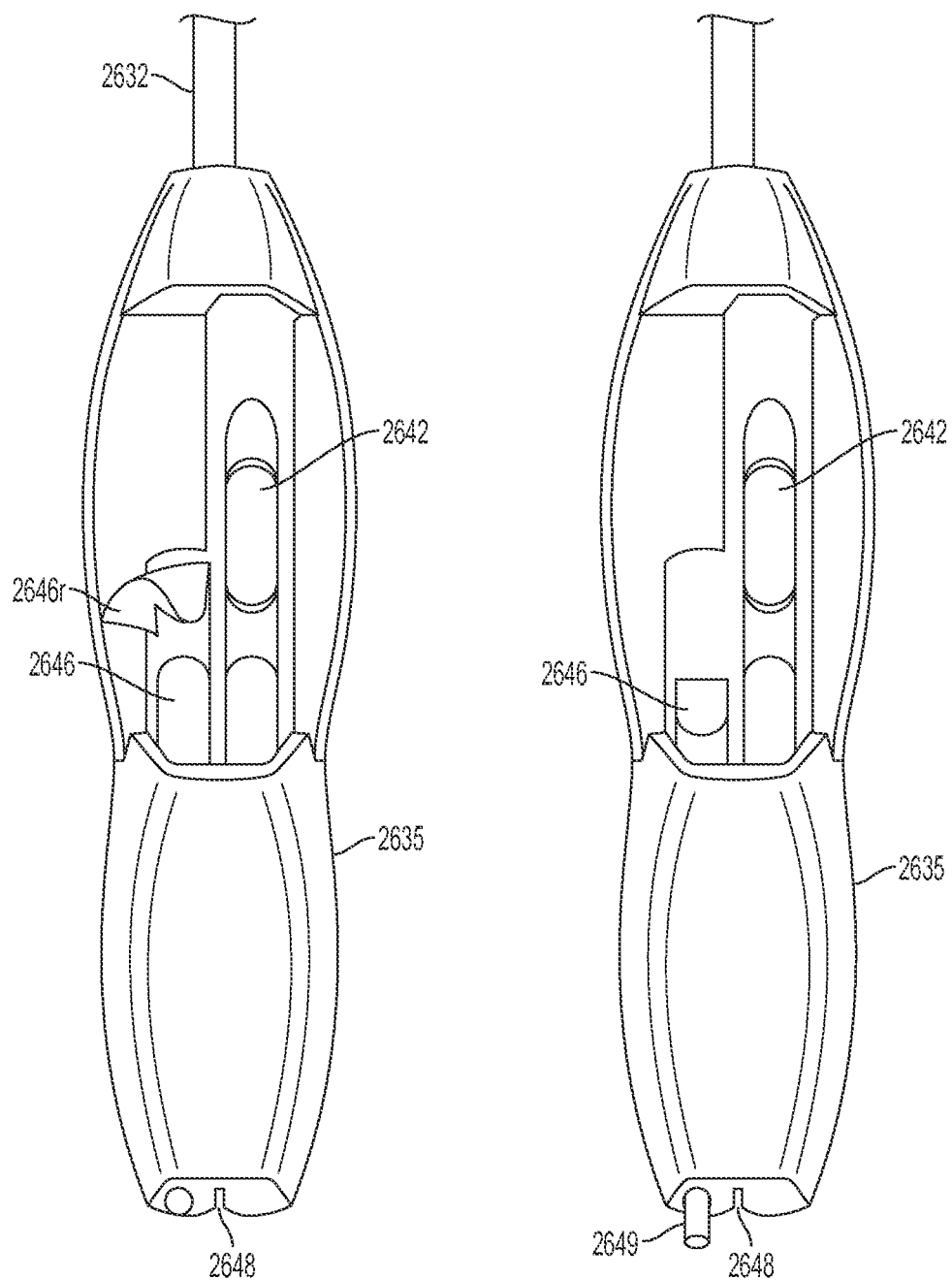

INTRAUTERINE SYSTEMS, IUD INSERTION DEVICES, AND RELATED METHODS AND KITS THEREFOR

CROSS-REFERENCE

This application claims the benefit of U.S. Provisional Application No. 61/506,434, filed Jul. 11, 2011, which application is incorporated herein by reference.

BACKGROUND OF THE INVENTION

Field of the Invention

The disclosure relates to intraurinary systems, intrauterine devices (IUDs), insertion devices, methods of use, and kits therefor.

Background of the Invention

An intrauterine device (IUD) is an object that, when placed in the uterus of a female, acts as a birth control device to prevent pregnancy. Two types of IUDs are commonly available, copper-containing devices and hormone-containing devices that release a progestogen. Hormonal containing devices are considered to be a different form of birth control and are may be distinguished in the literature by the term intrauterine system (IUS).

Copper IUDs work by negatively affecting the mobility of sperm and preventing the sperm from joining an egg. Additionally, the foreign copper body positioned within the uterus also irritates the lining of the uterus and uterine wall making it difficult for an embryo to plant in the wall if the egg is fertilized by the sperm. IUS devices, such as the hormonal IUD Mirena® (marketed by Bayer) reduce or prevent menstrual bleeding. The Mirena® device releases levonorgestrel (a progestogen).

A variety of shapes and sizes have been previously disclosed for IUD devices. See, for example, U.S. Pat. No. 3,407,806 to Hulka et al for Contraceptive Intra-Uterine Devices issued Oct. 29, 1968; U.S. Pat. No. 3,902,483 to Place et al. for Intrauterine Device with Locator Means for Indicating Uterine Position of Device issued Sep. 2, 1975; U.S. Pat. No. 4,372,302 to Akerlund for Instrument for Retrieval of Retracted Threads of Intrauterine Contraceptive Devices issued Feb. 8, 1983; U.S. Pat. No. 3,973,217 to Kosenen for Intrauterine Contraceptive Device issued Feb. 10, 1976; U.S. Pat. No. 4,353,363 to Sopena Quesada for Intrauterine Spermacide issued Oct. 12, 1982; U.S. Pat. No. 4,359,046 to Shaw Jr. for IUD Arrangement issued Nov. 16, 1982; U.S. Pat. No. 4,381,001 to Shaw Jr. for IUD Arrangement issued Apr. 26, 1983; U.S. Pat. No. 4,495,934 to Shaw Jr. for IUD Arrangement issued Jan. 29, 1985; U.S. Pat. No. 4,830,025 to Gainutdinova et al. for Intrauterine Contraceptive Device issued May 16, 1989; U.S. Pat. No. 4,957,119 to de Nijs for Contraceptive Implant issued Sep. 18, 1990; U.S. Pat. No. 5,088,505 to de Nijs for Contraceptive Implant issued Feb. 18, 1992; U.S. Pat. No. 6,039,968 to Nabahi for Intravaginal Drug Delivery Device issued Mar. 21, 2000; U.S. Pat. No. 7,862,552 to McIntyre et al. for Medical Devices for Treating Urological and Uterine Conditions issued Jan. 4, 2011; and U.S. Patent Publications 2005/0045183 A1 to Callister et al. for Methods and Devices issued Mar. 3, 2005.

IUDs are typically inserted using an insertion device or instrument. See, for example, U.S. Pat. No. 3,783,861 to Abramson for Inserter for Intrauterine Devices issued Jan. 8, 1974; U.S. Pat. No. 3,794,025 to Lerner for Intrauterine Device Saddle Inserter issued Feb. 26, 1974; U.S. Pat. No. 4,920,727 to Ristimaki et al. for Cassette System and Apparatus for Manufacturing an Active Agent Liberating Capsule for Subcutnaeous Use issued May 1, 1990; U.S. Pat. No. 4,949,732 to Spoon et al. for Apparatus for Insertion and Fixation of an Intra Uterine Contraceptive Device to the Uterine Fundus issued Aug. 21, 1990; U.S. Pat. No. 5,084,004 to Ranoux for Process for Intra-Uterine Fertilization in Mammals and Device for Implementation Thereof issued Jan. 28, 1992; U.S. Pat. No. 5,370,129 to Diaz et al. for IUD Inserting Apparatus issued Dec. 6, 1994; U.S. Pat. No. 5,400,804 to Helle et al. for Method and Equipment for Installing a Medicine Capsule on a Support issued Mar. 28, 1995; U.S. Pat. No. 5,785,053 to Macandrew et al. for Inserter for the Positioning of an Intrauterine Device issued Jul. 28, 1998.

Other references of interest in the IUS and IUD field include, for example, U.S. Pat. No. 6,056,76 to Markkula et al. for Elastomer, Its Preparation and Use issued May 2, 2000; U.S. Pat. No. 6,063,395 to Markkula et al. for Drug Delivery Device Especially for the Delivery of Progestins and Estrogens issued May 16, 2000; U.S. Pat. No. 6,103,256 to Nahabi for Intravaginal Drug Delivery Device issued Aug. 15, 2000; U.S. Pat. No. 6,117,442 to Markkula et al. for Drug Delivery Device, Especially for the Delivery of Androgens issued Sep. 12, 2000; and U.S. Patent Publication US 2008/0095825 A1 to LaFont for Method for Making a Reservoir Containing an Active Substance Diffused through the Reservoir and Installation Therefor published Apr. 24, 2008.

Conventional insertion devices used with IUDs (which includes devices used for IUSs) can cause pain and even loss of consciousness to a patient during the insertion procedure as a result of induction of a vagal reflex response. Conventional insertion devices lack smooth operability and exhibit issues with ease of use. Thus, there exists a need for an insertion device adaptable and configurable for use with IUDs and related methods and kits which reduce patient pain and trauma during the insertion procedure and provides a simple, high-quality, easy-to-use, smoothly operating, economical solution.

SUMMARY OF THE INVENTION

An aspect of the disclosure is directed to insertion devices comprising: an elongated sheath having a proximal end and a distal end and a lumen extending between the proximal end and the distal end; an elongated inner member having a proximal end and a distal end disposable within the lumen of the elongated sheath; a proximally positioned user interface, wherein the proximally positioned user interface further comprises one or more elongated guides formed at least partially therein and along at least a portion of a length thereof; and a moveable sheath slider in communication with the elongated sheath wherein the moveable sheath slider is adaptable and configurable to securely move within the elongated guide and further wherein the moveable sheath slider controls axial movement of the elongated sheath. The elongated guide is further configurable to comprise one or more motion control features along the length of the elongated guide. Additionally, the one or more motion control features are selected from the group comprising a hard motion control feature, a soft motion control feature. Moreover, the one or more motion control features comprises at least one force-limiting feature configurable to limit an amount of force applied to the moveable sheath slider. The one or more motion control features are selectable from the group comprising detents, notches, grooves, protrusions, tabs, ridges, flanges, flaps, gates, flexible members, elongated guide contours, and elongated guide curved surface. Additionally, the elongated guide has a length, a width and a depth, and further wherein the elongated guide width is at least one of a variable length along and a staged width selected from two or more of a first width and a second width. The elongated guide can further be configured to have an in-plane profile selected from rectangular, s-shaped, c-shaped, u-shaped, w-shaped, circular, semi-circular, and oval. The sheath slider can also be configured to comprise one or more surface profiles adapted and configured to mechanically complement the one or more motion control features. The one or more surface profiles of the sheath slider are selected from the group comprising one or more of each of non-planar surfaces, curved surfaces, and angled surfaces. Additionally, the housing and the sheath slider further comprises one or more alignment surfaces, wherein the one or more alignment surfaces of the housing is adapted and configured to mechanically complement the one or more alignment surfaces of the sheath. In at least some configurations, a first sheath slider alignment surface aligns with a first housing alignment surface at a first position along the length of the elongated guide. Additionally, the one or more sheath slider alignment surfaces and the one or more housing alignment surfaces are selected from the group comprising a curved surface, an angled surface, a tilted surface and a dimensional surface. The elongated guide can further be configured to comprise one or more cavities on one or more of the proximal end of the elongated guide and the distal end of the elongated guide wherein the one or more cavities are adapted and configured to house at least a portion of the movable sheath slider. In at least some configurations, the devices further comprise a string control slider. The string control slider can be adaptable and configurable to securely move within the elongated guide. Additionally, the elongated sheath slider and the string control slider are adapted and configured to operate at least one of simultaneously and independently within one or more elongated guides. In at least some configurations, the sheath slider and the string control slider are telescopically movable along at least a first portion of the elongated guide, and further wherein the sheath slider and the string control slider are configurable such that at least one of the sheath slider and the string slider partially surrounds the remaining slider. The sheath slider and string control slider are further configurable to comprise one or more vertical surfaces, wherein the one or more vertical surfaces are selected from the group comprising a first sheath slider vertical surface, a second sheath slider vertical surface, a first string control slider vertical surface, and a second string control vertical surface, wherein one or more of the vertical surfaces are configured to form an aligned adjacent surface at one or more positions along the length of the elongated guide. Typically, devices are configurable such that the sheath slider and the string control slider have a combined width less than or equal to at least one of 0.75 inches (19 mm), 0.7 inches (17.8 mm), 0.5 inches (12.7 mm), 0.35 inches (8.9 mm), or 0.25 inches (6.3 mm). The insertion device is also configurable to receive an IUD within the distal end of the lumen of the elongated sheath further comprising at least one string locking feature adaptable and configurable to secure one or more string components of the IUD. In some configurations the at least one string locking feature comprises one or more of a cleft, a clamp, a wedge, a pincher, a spring, or teeth. In other configurations, the string locking feature comprises a cleft, and the string unlocking feature comprises a movable member which pushes the one or more strings out of the cleft to unlock the one or more strings. The distal end of the elongated sheath is also configurable such that it has an atraumatic tip selected from the group comprising a rounded tip and a tapered tip. The distal end of the elongated sheath has an outer diameter of about 3 mm to 5 mm. In some configurations, the distal end of the elongated sheath has an outer diameter which is equal to or less than 80%, 50%, 30% of the outer diameter of the proximal end of the elongated sheath. Additionally, the distal end of the elongated sheath is configurable such that it has an outer diameter which is less than the maximum cross-sectional dimension of an IUD positionable within the lumen of the elongated sheath. In at least some configurations, the distal end of the elongated sheath further comprises one or more slits or flaps at the forward end of the sheath. Additionally, one or more feedback mechanisms can be provided which selected from the group comprising audible, visible, and tactile.

Another aspect of the disclosure is directed to insertion devices comprising: an elongated sheath having a proximal end and a distal end and a lumen extending between the proximal end and the distal end; an elongated inner member having a proximal end and a distal end disposable within at least a portion of the lumen of the elongated sheath; a proximally positioned user interface; and an actuatable sheath control button associated with the proximally positioned user interface in communication with the elongated sheath wherein the actuatable sheath control button is adaptable and configurable to controls axial movement of the elongated sheath wherein the elongated sheath extends distally from the housing, and wherein the sheath control button causes the sheath to proximally retract when the sheath control button is actuated. The elongated guide is further configurable to comprise one or more motion control features along the length of the elongated guide. Additionally, the one or more motion control features are selected from the group comprising a hard motion control feature, a soft motion control feature. Moreover, the one or more motion control features comprises at least one force-limiting feature configurable to limit an amount of force applied to the moveable sheath slider. The one or more motion control features are selectable from the group comprising detents, notches, grooves, protrusions, tabs, ridges, flanges, flaps, gates, flexible members, elongated guide contours, and elongated guide curved surface. Additionally, the elongated guide has a length, a width and a depth, and further wherein the elongated guide width is at least one of a variable length along and a staged width selected from two or more of a first width and a second width. The elongated guide can further be configured to have an in-plane profile selected from rectangular, s-shaped, c-shaped, u-shaped, w-shaped, circular, semi-circular, and oval. The sheath slider can also be configured to comprise one or more surface profiles adapted and configured to mechanically complement the one or more motion control features. The one or more surface profiles of the sheath slider are selected from the group comprising one or more of each of non-planar surfaces, curved surfaces, and angled surfaces. Additionally, the housing and the sheath slider further comprises one or more alignment surfaces, wherein the one or more alignment surfaces of the housing is adapted and configured to mechanically complement the one or more alignment surfaces of the sheath. In at least some configurations, a first sheath slider alignment surface aligns with a first housing alignment surface at a first position along the length of the elongated guide. Additionally, the one or more sheath slider alignment surfaces and the one or more housing alignment surfaces are selected from the group comprising a curved surface, an angled surface, a tilted surface and a dimensional surface. In at least some configurations, the sheath slider and the string control slider are telescopically movable along at least a first portion of the elongated guide, and further wherein the sheath slider and the string control slider are configurable such that at least one of the sheath slider and the string slider partially surrounds the remaining slider. The sheath slider and string control slider are further configurable to comprise one or more vertical surfaces, wherein the one or more vertical surfaces are selected from the group comprising a first sheath slider vertical surface, a second sheath slider vertical surface, a first string control slider vertical surface, and a second string control vertical surface, wherein one or more of the vertical surfaces are configured to form an aligned adjacent surface at one or more positions along the length of the elongated guide. Typically, devices are configurable such that the sheath slider and the string control slider have a combined width less than or equal to at least one of 0.75 inches (19 mm), 0.7 inches (17.8 mm), 0.5 inches (12.7 mm), 0.35 inches (8.9 mm), or 0.25 inches (6.3 mm). The insertion device is also configurable to receive an IUD within the distal end of the lumen of the elongated sheath further comprising at least one string locking feature adaptable and configurable to secure one or more string components of the IUD. In some configurations the at least one string locking feature comprises one or more of a cleft, a clamp, a wedge, a pincher, a spring, or teeth. In other configurations, the string locking feature comprises a cleft, and the string unlocking feature comprises a movable member which pushes the one or more strings out of the cleft to unlock the one or more strings. The distal end of the elongated sheath is also configurable such that it has an atraumatic tip selected from the group comprising a rounded tip and a tapered tip. The distal end of the elongated sheath has an outer diameter of about 3 mm to 5 mm. In some configurations, the distal end of the elongated sheath has an outer diameter which is equal to or less than 80%, 50%, 30% of the outer diameter of the proximal end of the elongated sheath. Additionally, the distal end of the elongated sheath is configurable such that it has an outer diameter which is less than the maximum cross-sectional dimension of an IUD positionable within the lumen of the elongated sheath. In at least some configurations, the distal end of the elongated sheath further comprises one or more slits or flaps at the forward end of the sheath. In some configurations, the sheath control button and the string control button are disposable adjacent to one another on the housing.

Still another aspect of the disclosure is directed to insertion devices comprising: an elongated sheath having a proximal end and a distal end and a lumen extending between the proximal end and the distal end wherein the distal end of the elongated sheath forms an atraumatic tip selected from the group comprising a rounded tip and a tapered tip; an elongated inner member having a proximal end and a distal end disposable within the lumen of the elongated sheath; and a proximally positioned user interface. The elongated guide is further configurable to comprise one or more motion control features along the length of the elongated guide. Additionally, the one or more motion control features are selected from the group comprising a hard motion control feature, a soft motion control feature. Moreover, the one or more motion control features comprises at least one force-limiting feature configurable to limit an amount of force applied to the moveable sheath slider. The one or more motion control features are selectable from the group comprising detents, notches, grooves, protrusions, tabs, ridges, flanges, flaps, gates, flexible members, elongated guide contours, and elongated guide curved surface.

Additionally, the elongated guide has a length, a width and a depth, and further wherein the elongated guide width is at least one of a variable length along and a staged width selected from two or more of a first width and a second width. The elongated guide can further be configured to have an in-plane profile selected from rectangular, s-shaped, c-shaped, u-shaped, w-shaped, circular, semi-circular, and oval. The sheath slider can also be configured to comprise one or more surface profiles adapted and configured to mechanically complement the one or more motion control features. The one or more surface profiles of the sheath slider are selected from the group comprising one or more of each of non-planar surfaces, curved surfaces, and angled surfaces. Additionally, the housing and the sheath slider further comprises one or more alignment surfaces, wherein the one or more alignment surfaces of the housing is adapted and configured to mechanically complement the one or more alignment surfaces of the sheath. In at least some configurations, a first sheath slider alignment surface aligns with a first housing alignment surface at a first position along the length of the elongated guide. Additionally, the one or more sheath slider alignment surfaces and the one or more housing alignment surfaces are selected from the group comprising a curved surface, an angled surface, a tilted surface and a dimensional surface. The elongated guide can further be configured to comprise one or more cavities on one or more of the proximal end of the elongated guide and the distal end of the elongated guide wherein the one or more cavities are adapted and configured to house at least a portion of the movable sheath slider. In at least some configurations, the devices further comprise a string control slider. The string control slider can be adaptable and configurable to securely move within the elongated guide. Additionally, the elongated sheath slider and the string control slider are adapted and configured to operate at least one of simultaneously and independently within one or more elongated guides. In at least some configurations, the sheath slider and the string control slider are telescopically movable along at least a first portion of the elongated guide, and further wherein the sheath slider and the string control slider are configurable such that at least one of the sheath slider and the string slider partially surrounds the remaining slider. The sheath slider and string control slider are further configurable to comprise one or more vertical surfaces, wherein the one or more vertical surfaces are selected from the group comprising a first sheath slider vertical surface, a second sheath slider vertical surface, a first string control slider vertical surface, and a second string control vertical surface, wherein one or more of the vertical surfaces are configured to form an aligned adjacent surface at one or more positions along the length of the elongated guide. Typically, devices are configurable such that the sheath slider and the string control slider have a combined width less than or equal to at least one of 0.75 inches (19 mm), 0.7 inches (17.8 mm), 0.5 inches (12.7 mm), 0.35 inches (8.9 mm), or 0.25 inches (6.3 mm). The insertion device is also configurable to receive an IUD within the distal end of the lumen of the elongated sheath further comprising at least one string locking feature adaptable and configurable to secure one or more string components of the IUD. In some configurations the at least one string locking feature comprises one or more of a cleft, a clamp, a wedge, a pincher, a spring, or teeth. In other configurations, the string locking feature comprises a cleft, and the string unlocking feature comprises a movable member which pushes the one or more strings out of the cleft to unlock the one or more strings. The distal end of the elongated sheath has an outer diameter of about 3 mm to 5 mm. In some configurations, the distal end of the elongated sheath has an outer diameter which is equal to or less than 80%, 50%, 30% of the outer diameter of the proximal end of the elongated sheath. Additionally, the distal end of the elongated sheath is configurable such that it has an outer diameter which is less than the maximum cross-sectional dimension of an IUD positionable within the lumen of the elongated sheath. In at least some configurations, the distal end of the elongated sheath further comprises one or more slits or flaps at the forward end of the sheath. Additionally, one or more feedback mechanisms can be provided which selected from the group comprising audible, visible, and tactile. In at least some configurations, the device further comprises one or more motion control features along the length of the elongated guide.

An additional aspect of the disclosure is directed to kits comprising: an insertion device having an elongated sheath having a proximal end and a distal end and a lumen extending between the proximal end and the distal end; an elongated inner member having a proximal end and a distal end disposable within the lumen of the elongated sheath; a proximally positioned user interface, wherein the proximally positioned user interface further comprises one or more elongated guides formed at least partially therein and along at least a portion of a length thereof; and a moveable sheath slider in communication with the elongated sheath wherein the moveable sheath slider is adaptable and configurable to securely move within the elongated guide and further wherein the moveable sheath slider controls axial movement of the elongated sheath; and an intrauterine device positionable within the distal lumen of the elongated sheath.

Still other aspects of the disclosure are directed to kits comprising: an insertion device having an elongated sheath having a proximal end and a distal end and a lumen extending between the proximal end and the distal end, an elongated inner member having a proximal end and a distal end disposable within the lumen of the elongated sheath, a proximally positioned user interface, and an actuatable sheath control button associated with the proximally positioned user interface in communication with the elongated sheath wherein the actuatable sheath slider is adaptable and configurable to controls axial movement of the elongated sheath, wherein the elongated sheath extends outward from the housing, and wherein the sheath control button causes the sheath to proximally retract when the sheath control button is actuated, and an intrauterine device positionable within the distal lumen of the elongated sheath.

Yet another aspect of the disclosure is directed to kits comprising an insertion device having an elongated sheath having a proximal end and a distal end and a lumen extending between the proximal end and the distal end, wherein the distal end of the elongated sheath forms an atraumatic tip selected from the group comprising a rounded tip and a tapered tip, an elongated inner member having a proximal end and a distal end disposable within the lumen of the elongated sheath, and a proximally positioned user interface; and an intrauterine device positionable within the distal lumen of the elongated sheath.

Still other aspects of the disclosure are directed to methods of using an insertion device comprising: advancing an insertion device having an elongated sheath having a proximal end and a distal end and a lumen extending between the proximal end and the distal end; an elongated inner member having a proximal end and a distal end disposable within the lumen of the elongated sheath; a proximally positioned user interface, wherein the proximally positioned user interface further comprises one or more elongated guides formed at least partially therein and along at least a portion of a length thereof; and a moveable sheath slider in communication with the elongated sheath wherein the moveable sheath slider is adaptable and configurable to securely move within the elongated guide and further wherein the moveable sheath slider controls axial movement of the elongated sheath; actuating the sheath slider; at least one of moving the elongated sheath proximally and advancing the IUD distally; automatically or semi-automatically increasing a radial diameter of the IUD; and releasing the IUD from the insertion device.

Additional aspects of the disclosure are directed to methods of using an insertion device comprising: advancing an insertion device having an elongated sheath having a proximal end and a distal end and a lumen extending between the proximal end and the distal end, an elongated inner member having a proximal end and a distal end disposable within the lumen of the elongated sheath, a proximally positioned user interface, and an actuatable sheath control button associated with the proximally positioned user interface in communication with the elongated sheath wherein the actuatable sheath slider is adaptable and configurable to controls axial movement of the elongated sheath, wherein the elongated sheath extends outward from the housing, and wherein the sheath control button causes the sheath to proximally retract when the sheath control button is actuated; actuating the sheath control button; at least one of moving the elongated sheath proximally and advancing the IUD distally; automatically or semi-automatically increasing a radial diameter of the IUD; and releasing the IUD from the insertion device.

The disclosure also contemplates methods of using an insertion device comprising: advancing an insertion device having an elongated sheath having a proximal end and a distal end and a lumen extending between the proximal end and the distal end, wherein the distal end of the elongated sheath forms an atraumatic tip selected from the group comprising a rounded tip and a tapered tip, an elongated inner member having a proximal end and a distal end disposable within the lumen of the elongated sheath, and a proximally positioned user interface; at least one of moving the elongated sheath proximally and advancing the IUD distally; automatically or semi-automatically increasing a radial diameter of the IUD; and releasing the IUD from the insertion device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

FIGS. 3A-3E illustrate positioning of an IUD during the first phase of IUD insertion;

FIGS. 4A-4C illustrate an animation of positioning of an IUD within an insertion device during transition from the first phase (1) to the second phase (2) of IUD insertion.

FIGS. 7A-A(3), 7B(1)-B(3), and 7C(1)-7C(3) illustrate various slot features and configurations suitable for incorporation into an insertion device handle;

FIG. 14A illustrates a top view and FIG. 14B illustrates a side view of an insertion device with telescoping sliders;

FIGS. 25A-25B illustrate various string locking features;

FIGS. 26A-26E illustrate various string control features, including string locking and string unlocking features;

DETAILED DESCRIPTION OF THE INVENTION

I. Insertion Procedure

Figures 1A, 1B, 1C:
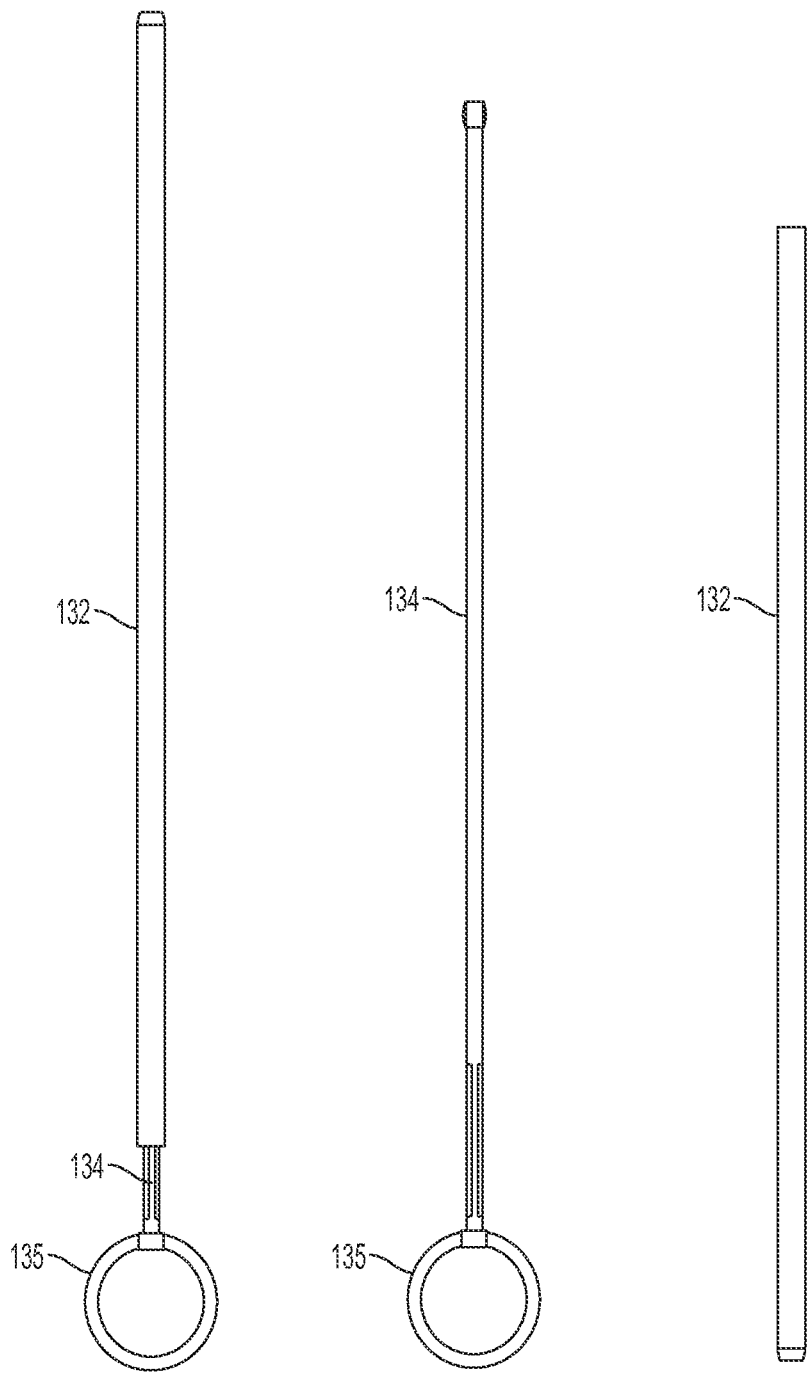
FIGS. 1A-1C illustrate a conventional IUD insertion device.

Conventional intrauterine insertion devices include an inserter or insertion device such as the device shown in FIGS. 1A-1C, which includes a sheath 132 having a proximal end and a distal end and a lumen extending between the proximal end and the distal end for housing the IUD, a plunger 134 for pushing the IUD through the sheath, and user interface such as a handle 135 for holding the insertion device. The device shown in FIGS. 1A-1C requires a two-handed procedure, whereby the operator holds the handle 135 in one hand and the sheath 132 in another hand.

As will be discussed in more detail below, in contrast to conventional insertion devices, such as depicted in FIG. 1, the insertion devices of the present disclosure are configured to house an IUD during the insertion procedure and is further configured to aid in positioning the IUD during the insertion procedure as well as advancing the IUD from the insertion device into a patient's uterus. The insertion device is adaptable and configurable for insertion of a variety of IUDs configurations.

Figure 2:
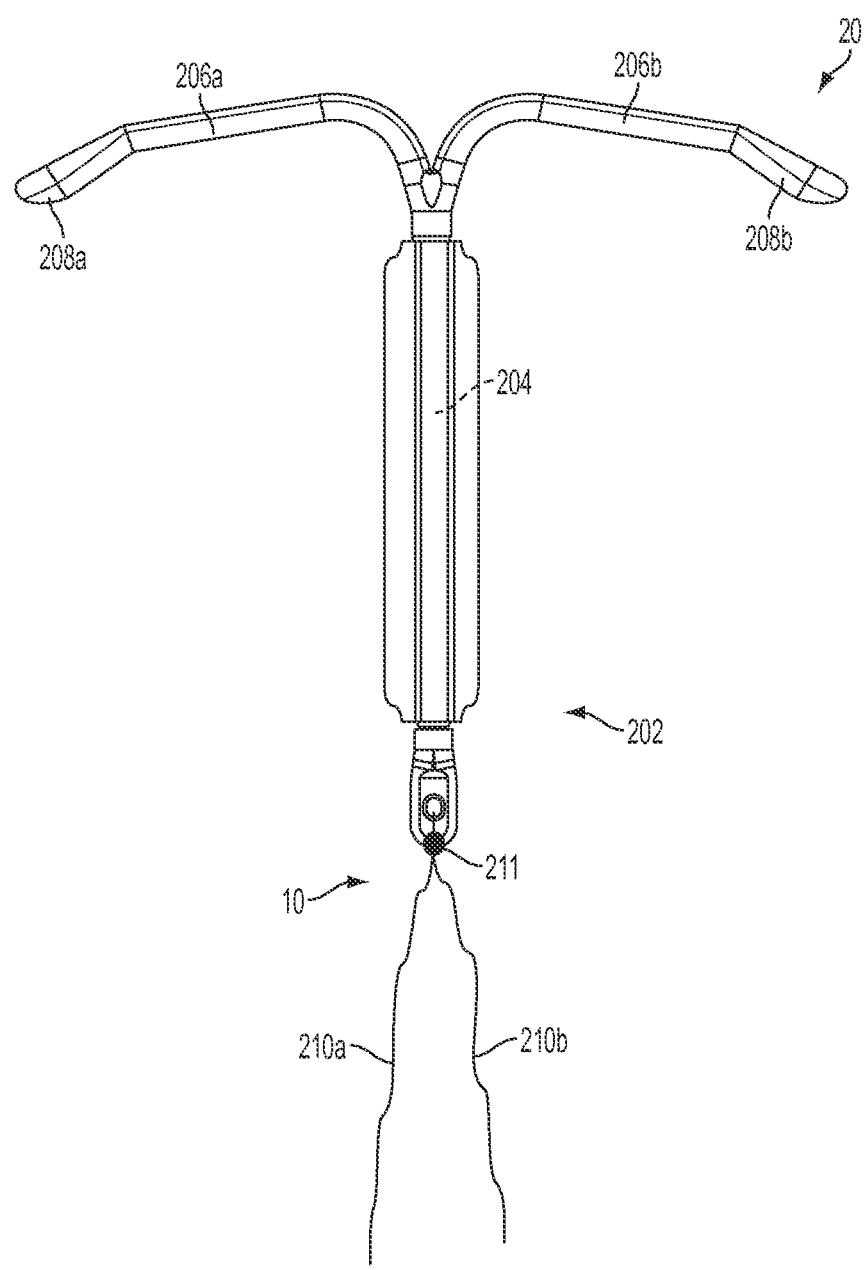
FIG. 2 illustrates a conventional T-shaped IUD.

The insertion devices can, for example, be used with a T-shaped IUD 202, such as the IUD as shown in FIG. 2. IUDs typically have a length of from about 31.90 mm to about 32.22 mm and a width of from about 31.81 mm to about 32.13 mm when the IUD is in the fully deployed position. As will be appreciated by those skilled in the art, the length does not include the knot or strings that may accompany the IUD. The T-shaped IUD comprises an elongated body 204 having a proximal end 10 and a distal end 20. The elongated body 204 can include a coating such as a time-release drug or hormone. The elongated body can be formed from any suitable material, including, but not limited to plastic or copper. At the distal end 20 of the IUD (i.e., the end positioned away from the physician's hand), arms 206a, 206b are attached to or integrally formed with the elongated body 204. The arms 206a, 206b are configurable to fold upward u or downward d to minimize the IUD cross-section such that the IUD can fit into an insertion device sheath or tube for insertion through the cervix and into the uterus. Additionally, either or both of the arms 206a, 206b are configurable to include an enlarged or bulbous tip 208a, 208b, which can, for example, have a curved, spherical or semi-spherical shape. The tips 208a, 208b of the arms 206a, 206b can be formed such that the arms, when folded upward and pushed together, form a smooth and rounded distal tip, for example, as shown in FIGS. 3B-3C and described below. At the proximal end of the IUD 10, the IUD can further include one or more strings 210a, 210b attached to the IUD. The strings are connectable to the IUD at a connection point 211, e.g., tied in a knot as illustrated.

Although the insertion device is generally described herein with regard to a T-shaped IUD such as the IUD shown in FIG. 2, it should be noted that the insertion devices of the present disclosure are adaptable to facilitate insertion of other IUD configurations, as would be appreciated by a person of skill in the art. Moreover, insertion device operation and IUD insertion procedures can include any number of steps corresponding to a desired IUD position. In addition to the features described below, the insertion devices of the present disclosure include IUD position control features which may be advantageous for insertion of IUDs having a variety of configurations. For example, while the IUD insertion procedure described below refers to a three-phase procedure corresponding to three different IUD positions, the insertion device operation procedure can include less than three or more than three steps. Accordingly, the insertion devices can include any number of position control features corresponding to the desired IUD positions. The insertion device of the present disclosure can be used with various conventional IUDs available on the market, including such devices as the T-frame LNg-20 IUD, marketed as Mirena® by Bayer®, as well as the Neo-Safe CuT 380A™ available from Mona-Lisa™.

Insertion device disclosed herein are configurable to operate according to procedural steps which generally mimic commonly known and used procedures for IUD insertion. However, the insertion device of the present disclosure includes improvements in device structure and operation. In another aspect of the disclosed devices, procedural steps for IUD insertion include: (i) pre-insertion insertion device preparation procedures, (ii) a first phase of IUD insertion (also referred to herein as phase 1, position 1, or step 1), (iii) a second phase of IUD insertion (also referred to herein as phase 2, position 2, or step 2), (iv) a third phase of IUD insertion (also referred to herein as phase 3, position 3, or step 3), and (v) post-insertion procedures.

Pre-insertion insertion device preparation procedures can include loading an IUD, such as the IUD illustrated in FIG. 2, into an insertion device, aligning the IUD in-plane with a patient, positioning the IUD in a correct longitudinal position along the length of a sheath of the insertion device, and locking the IUD into a position for insertion. Such pre-insertion insertion device preparation procedures are described in further detail below.

Figure 3D:
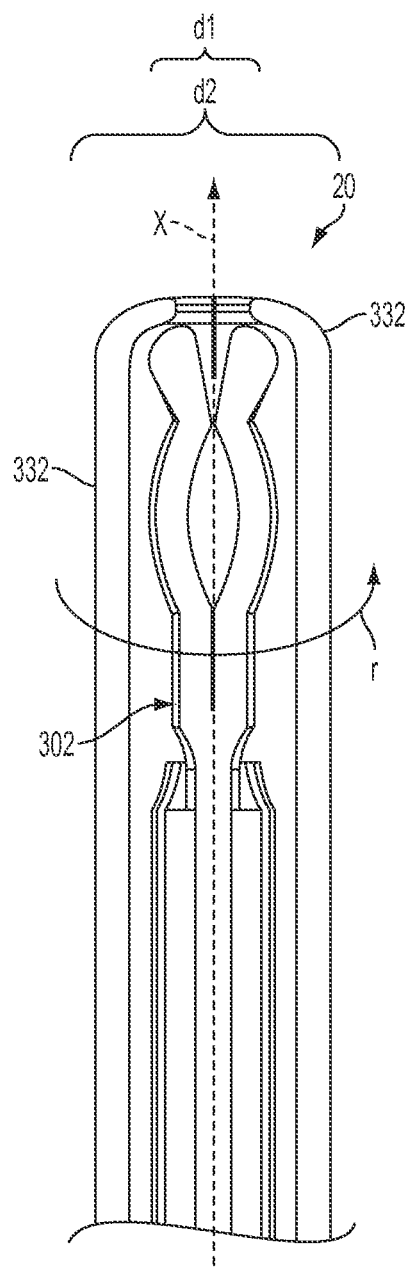

FIGS. 3A-3D illustrate positioning of an insertion device 300 during a first phase of IUD insertion according to an aspect of the present disclosure. The insertion device 300 is sized and configured for positioning within a uterus, having a tube length (or working length) of from 15 cm to 25 cm, and a diameter of 3 mm to about 5 mm. A distal end 20 of sheath 332, having a proximal end and a distal end and a lumen extending between the proximal end and the distal end, is advanced through a cervical canal (not shown) such that the sheath 332 protrudes slightly into the uterus, as illustrated in FIG. 3A using a demonstrator 333 representing a portion of the female anatomy engaged by the IUD including a cervical canal 321 area and a uterus 314 area. The IUD 302 is not yet deployed and remains within the sheath 332. The IUD hands 308a, 308b may be partially deployed to create a rounded shape at the distal tip 20 of the insertion device 300, as shown in FIG. 3B, while the elongated body 304 of the IUD remains within the sheath 332 Alternatively, in aspects where the insertion device sheath 332 or other feature provides a rounded distal tip, the IUD arms 306a, 306b are encasable by sheath 332, as shown in the cross-section taken along the lines B-B in FIG. 3B and shown in FIG. 3C. The distal end 20 of the sheath 332 is configurable such that it forms a rounded tip which can flare open when the IUD positioned within the sheath is advanced beyond its distal end (e.g., has an aperture of a first diameter when the IUD is fully positioned within the sheath, and an aperture of a second, larger, diameter when the IUD is advanced distally beyond the tip of the sheath).

A contraceptive device, which is available on the market and which releases levooorgestrel, consists of a T-shaped IUD 302 having an elongate member fabricated of polyethylene equipped with a reservoir adjusted around it and containing the hormone levooorgestrel. The IUD comprises a core part around which a jacket-like polymeric reservoir containing an active agent has been fitted. The active agent includes hormones used for the treatment of menopausal troubles or for contraception. The IUD is sold in sterile packaging together with the inserter with the plunger contained within the protecting tube. The T-shaped IUD device 302 is positioned at the forward end of the plunger with the hormone-containing elongate member protected by the tube. The wings 306a, 306b of the transverse member, on the other hand, are expanded in order to prevent fatigue. The strings by which the T-shaped device is retracted towards the outside run between the plunger and the protective tube and end at the end of the handle.

Figure 3E:
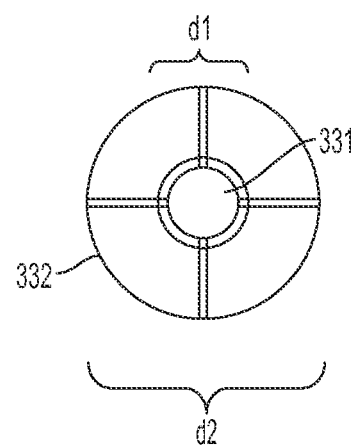

FIG. 3D shows another cross-section taken along the lines D-D in FIG. 3B of the insertion device 300. As can be seen in this illustration when the IUD 302 is positioned fully within the sheath 332, the distal 20 tip has an aperture 331 with a diameter d1 that is smaller than the diameter d2 of the IUD 302. FIG. 3E illustrates a view down the barrel of the device taken from the view E-E in FIG. 3B of the insertion device 300, during a first phase of IUD insertion according to an aspect of the present disclosure. Aperture 331 has a diameter d1 that is smaller than the diameter d2 of the sheath 332. The IUD 302 is rotatable r in-plane about longitudinal axis x as shown in FIG. 3D, such that the IUD arms or similar features of the IUD will deploy in-line with respective openings of the patient's fallopian tubes.

Figure 4D:
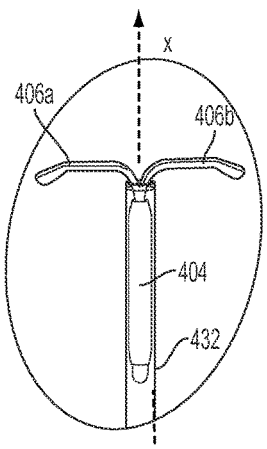
FIGS. 4D-4F illustrate positioning of an IUD within an insertion device during the second phase of IUD insertion.
Figure 4E:
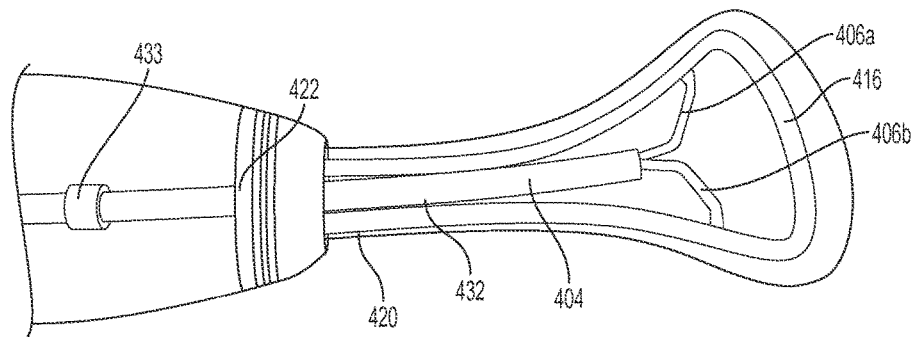
Figure 4F:
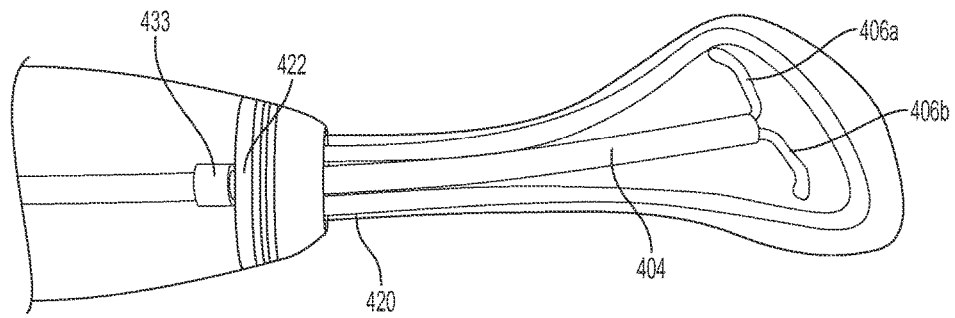

FIGS. 4A-4C depict a cross-section of the IUD 402 in combination with an insertion device 400 during transition from a first phase (1) to a second phase (2) of IUD insertion, along cross-section D-D of FIG. 3B. As illustrated in FIG. 4c the arms 406a, 406b of the IUD 402 have been advanced distally (i.e., towards the distal end 20) and out of the sheath 432, which has a proximal end and a distal end and a lumen extending between the proximal end and the distal end, which allows the arms 406a, 406b to extend radially away from a central axis x. FIGS. 4D-4F illustrate positioning of an insertion device 400 during a second phase of IUD insertion. In phase 2, the IUD 402 is partially deployed from the sheath 432 as shown in FIG. 4B.

Turning now to FIGS. 4D-4F, the IUD 402 is partially deployed such that the elongated body 404 of the IUD 402 remains positioned within the sheath 432, and the arms 406a, 406b deploy from the sheath 432 and unfold to extend outward from the elongated body 404 of the IUD 402. As shown in FIG. 4E, the insertion device 400 is extended distally into the uterus (not shown) until a flange 433 reaches a set distance from an external orifice 422 of the cervix 420, and the IUD is partially deployed from the insertion device sheath 432 into the uterus (not shown). A clinician operating the insertion device can, during use, maintain a position shown in FIG. 4E for a period of time, e.g., 10-25 seconds, and more often 15 seconds, to ensure that the IUD arms 406a, 406b are fully unfolded or expanded to the desired position or configuration. Subsequently, as shown in FIG. 4F, the insertion device 400 is advanced distally until the flange 433 reaches the external orifice of the cervix (not shown), whereby the IUD arms 406a, 406b contact the fundus 416 of the uterus (not shown).

Figure 5A:
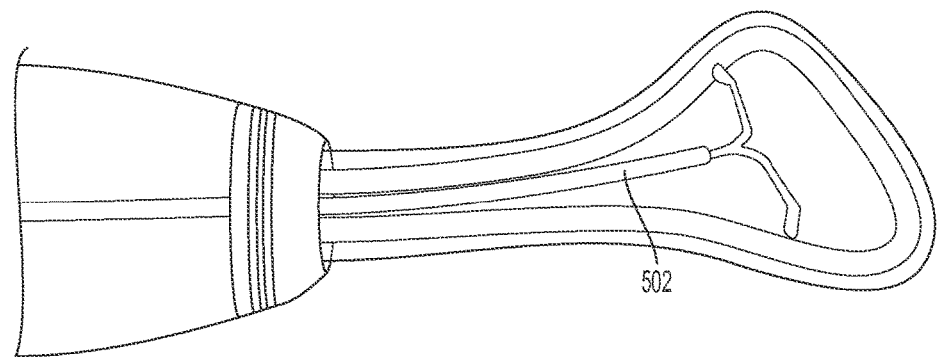
FIGS. 5A-5C illustrate positioning of an IUD during the third phase of insertion.
Figure 5B:
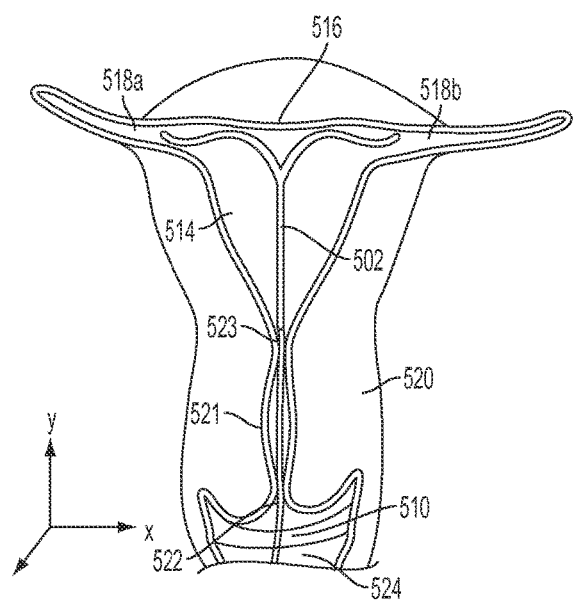
Figure 5C:
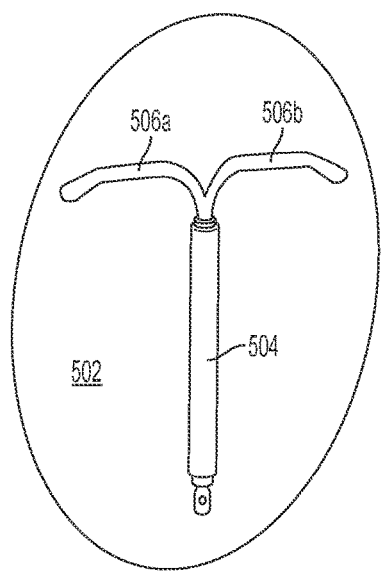

FIGS. 5A-5C illustrate positioning of an IUD 502 during a third phase of an insertion procedure. As shown in FIGS. 5A-5B, the IUD 502 is completely deployed from the insertion device (not shown) into the uterus 514, and the IUD strings 510 extend from the uterus 514, through the cervix 520, and into the vagina 524, as shown in FIG. 5B. FIG. 5B provides a planar view showing a detailed illustration of the relevant female anatomy, including the uterus 514, fundus 516, openings of the fallopian tubes 518a, 518b, cervix 520, cervical canal 521, external orifice 522 of the cervix 520, and internal orifice 523 of the cervix 520.

Upon completion of the IUD insertion phase, post-insertion procedures are performed, such as removal of the insertion device sheath from the patient and trimming the IUD strings to an appropriate length for a particular patient.

The insertion devices of the present disclosure demonstrate improved device structure and operation technique, as well as increases the ease of operability. The insertion devices of the present disclosure are configured to reduce pain and trauma suffered by patients during the IUD insertion procedure. Most women have a cervix which varies in diameter of the opening from about 1 to about 3 millimeters. The size and shape of the cervix varies widely with the patient's age, the patient's hormonal state, and whether the patient has born a child via vaginal birth. However, the IUD and insertion device typically have a diameter larger than the diameter of the cervical canal, especially at the external orifice and internal orifice of the cervix or uterus. Such a mismatch between the diameters of the cervix and insertion device creates a resistive pathway for IUD insertion which can hinder proper insertion of the IUD and result in a traumatic insertion for the patient. Diameters of IUDs and traditional insertion devices are large compared to the typical female human cervical canal into which the IUD and applicator are inserted during the IUD insertion process. As will be appreciated by those skilled in the art, traumatic IUD insertion procedures can cause a variety of adverse side effects including, but not limited to, bleeding, intense pain, and an adverse vasovagal response, which can result in fainting or seizure.

Pain during the IUD insertion procedure is reduced by the structure and operation of the insertion device, as well as by the ease of operability of the insertion device. Traumatic insertion can result from difficulties in operating the IUD insertion tool, malfunctioning of the insertion device, improper IUD positioning during insertion, operator error, and inherent design features of the insertion device itself. The insertion devices of the present disclosure are configured to reduce resistance and friction during the IUD insertion process. The insertion devices are configurable to operate smoothly, quickly, steadily, easily, and in a highly controlled and consistent manner, thereby reducing trauma to the patient during insertion and deployment of the IUD.

The present disclosure provides insertion device structures and operation which controls the position of the IUD during various phases of the insertion procedure. Traditional insertion devices do not provide a reliable mechanism to position the IUD and maintain appropriate IUD positioning throughout the insertion procedure. Securing the IUD in the proper location during multiple stages of insertion is important for proper and painless insertion. Improper IUD positioning such as misalignment and premature or late deployment of the IUD can cause unsuccessful and painful insertion. The present disclosure provides improved position control through the use of position control features for control of both in-plane and longitudinal alignment of the IUD during the insertion procedure. In an aspect of the disclosed devices, the insertion device further includes position control feedback or signal features to provide verification and assurance of proper IUD positioning.

II. IUD Position & Allotment Control

The insertion devices of the present disclosure are configurable to exhibit a high degree of control and accuracy of the position of an IUD during an IUD insertion procedure. It is important to control the positioning and alignment of the IUD with a high degree of accuracy during the IUD insertion procedure. For example, in the IUD insertion procedure illustrated in FIGS. 3-5 and discussed above, it is important to control the longitudinal position of the IUD, in-plane alignment of the IUD, and cross-section of the IUD and insertion device sheath.

As discussed above, the IUD 302 is rotatable r in-plane about longitudinal axis x as shown in FIG. 3D, such that the IUD arms or similar features of the IUD will deploy in-line with respective openings of the patient's fallopian tubes 518a, 518b, as shown in FIG. 5B, to achieve an in-plane alignment. Generally speaking, when an IUD is in an in-plane alignment the IUD is laid flat, or substantially flat, within a plane defined by the openings of fallopian tubes 518a, 518b and cervical canal 521, such as the coronal plane shown x-y in FIG. 5B. The IUD arms 506a, 506b, or the like functional feature for a non-T-shaped IUDs, will be positioned near the openings of the fallopian tubes 518a, 518b when the IUD is deployed. The proximal end of the IUD elongated body 504 is proximate to the internal orifice 523 of the cervix, and the IUD strings 510 extend proximally from the IUD 502 into the vagina 524.

In phase 1 of insertion, as shown in FIGS. 3A-3E, the IUD 302 is positioned within a delivery device 300 such that the IUD 302 will not prematurely deploy but will deploy readily during the transition to phase 2. The cross-section of a distal end 20 of the insertion device 300 is configurable such that it presents a minimal diameter along a longitudinal portion of the insertion device that is inserted into a patient's cervix and uterus, and the distal tip 301 of the insertion device 300 is further configurable to present a distal end that is rounded or curved, smooth, and free of blunt or abrupt features. The use of a rounded distal tip which is free of blunt or abrupt features reduces or eliminates harm or trauma to the patient and reduces any impediment to smooth insertion of the insertion device through the cervical canal and into the uterus. The IUD 302 is preferably deployed into the uterus having in-plane alignment such that the deployed IUD will be substantially in, for example, a coronal plane as discussed above.

Position Control Features

The present disclosure describes insertion devices comprising one or more features for controlling a longitudinal position of an IUD throughout various phases of the IUD insertion procedure. The insertion devices are adaptable and configurable to include an IUD insertion device comprising an elongated inner member and an elongated sheath at least partially encasing or surrounding the elongated inner member, wherein the inner member and sheath are configurable to engage in translation movement relative to one another along the longitudinal axis. The IUD insertion devices moreover can accommodate a variety of IUD configurations.

The elongated sheath of the insertion device houses the IUD during the insertion procedure and has a narrow sheath tip cross-section at its distal end such that the distal end of the sheath and IUD housed therein will fit through the cervix during insertion of the insertion device into the uterus. In at least some configurations, the distal 1 mm to 2 mm of the tip of the tube is tapered from its maximum diameter (e.g., 3-5 mm) to a value at the distal most portion that is about 50-90% of the diameter (e.g., a diameter from about 2.4 mm to about 4.4 mm). The insertion device sheath tip is configured to compress an IUD positioned within the sheath along the elongated or longitudinal axis of the IUD by confining the IUD within a narrow sheath opening. In at least some configurations, the insertion device sheath is an elongated member which is hollow, such as an elongated hollow cylinder or tube, along at least a portion of its longitudinal length. The elongated sheath of the insertion device is further configurable to be flexible enough to allow the sheath to be moldable or conformable to each patient's unique anatomy, yet strong and rigid enough to prevent collapsing or undesired movement during the insertion procedure. Suitable materials for the insertion device sheath include biocompatible materials such as plastic or thermoplastic polymer including, for example, polyethylene or polypropylene.

The elongated inner member fits at least partially within the cavity or opening of the sheath, and thus, the elongated inner member is at least partially encased or surrounded by the sheath, whereby the inner member can glide within the sheath along a longitudinal axis without undesired friction. The elongated inner member can be a rod, sheath, or any elongated member capable of translating the IUD along a longitudinal axis during the IUD insertion procedure. The elongated inner member, or plunger, is typically configured such that it is flexible enough to allow the plunger to take the shape of the elongated sheath once molded or conformed to an individual patient's anatomy. Suitable materials for the insertion device sheath includes biocompatible thermoplastic polymers such as polyethylene or polypropylene. In an aspect of the disclosed devices, at least a portion of the plunger is hollow to provide a pathway for one or more string components of the IUD to pass.

The translational movement of the elongated inner member and insertion device sheath relative to one another along a longitudinal axis allows for translational movement of the IUD relative to the insertion device sheath and/or elongated inner member along the longitudinal axis. The IUD and inner member typically do not translate along the longitudinal axis relative to one another. Additionally, the insertion device sheath and IUD typically translate relative to one another along the longitudinal axis during the IUD insertion procedure, whereby the insertion device sheath is pulled proximally (withdrawn) from the uterus and cervix while the IUD remains deployed in the uterus.

As will be appreciated by those skilled in the art, the insertion devices are configurable such that the elongated inner member can be pushed or extended distally (toward the patient and away from the operator) to deploy the IUD or withdrawn or extended proximally (away from the patient and towards the operator). Thus, for example, the sheath can be withdrawn proximally and/or the elongated inner member can be extended distally to deploy the IUD.

In some configurations, the plunger is configurable such that it remains stationary during the insertion procedure and only the sheath is retracted. In other aspects, the sheath is configurable to remain stationary and only the plunger is advanced distally. In still other aspects, the insertion device includes one or more of sheath and plunger position control features which allow movement of both the sheath and the plunger, either simultaneously or at different times and either the same distance or different distances. For example, in step 1, the insertion device is advanced distally through the cervical canal and into the uterus. In step 2, the position control feature pushes the plunger distally slightly to deploy the IUD arms. Optionally, the position control feature then moves both the plunger and sheath distally so that the arms of the IUD approach the fundus of the uterus (i.e., the top portion opposite the cervix). In step 3, either the sheath is retracted and the plunger is advanced distally, or the sheath alone is retracted proximally.

The insertion devices of the disclosure are further adaptable and configurable to include a handheld IUD insertion device further comprising an elongated inner member, an elongated sheath at least partially encasing or surrounding the elongated inner member, and at least one control feature which controls the translational movement of the elongated inner member and the elongated sheath relative to one another along a longitudinal axis.

III. Slider Controls

Figure 6A:
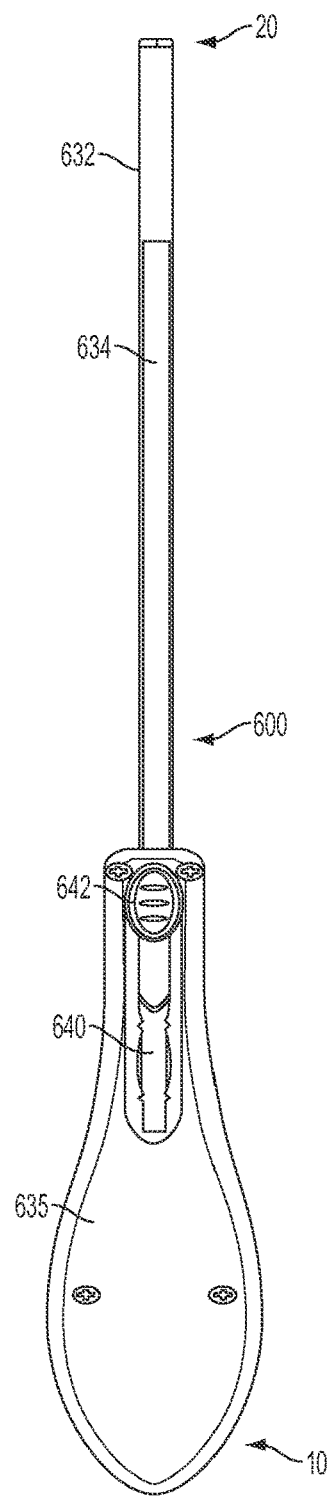
FIG. 6A illustrates a top view of an insertion device.
Figure 6B:
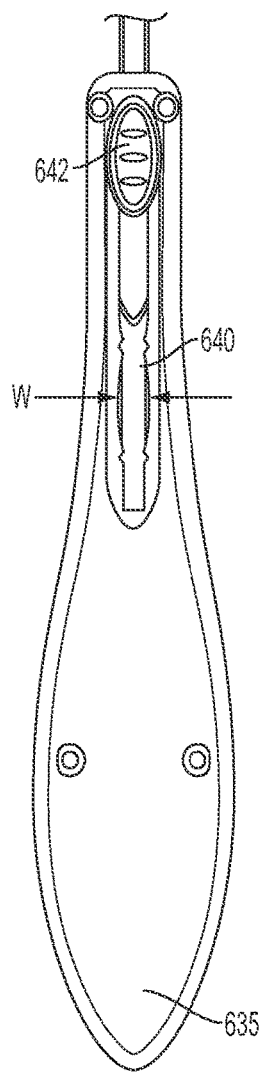
FIGS. 6B-6D illustrate details of an insertion device handle, slider, and slot features.
Figure 6C:
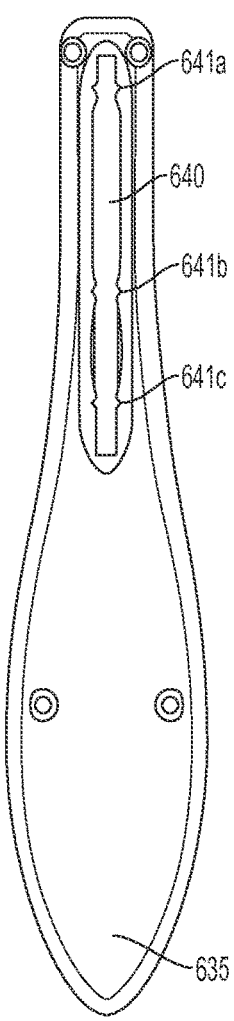

In an aspect of the insertion devices of the present disclosure, as illustrated in FIGS. 6A-6C, the insertion device 600 having a proximal end 10 and a distal end 20, comprises a handheld insertion device, comprising an elongated inner member (plunger) 634, an elongated sheath 632, an interface such as user interface or handle 635, and a slider 642 for actuating or controlling the translational movement of the elongated sheath 632 and the elongated inner member 634 relative to one another along their longitudinal axes. The insertion device handle 635 provides a housing for insertion device parts such as the proximal end 10 of the sheath 632, the proximal end of the plunger 634, and slider 642. The handle 635 is further configurable to enable an operator to engage the handle 635 when operating the insertion device 600. The handle 635 is configurable to include an elongated guide (slot, channel, slider track or slider window) 640. Elongated guide 640 is adaptable and configurable to provide a guide or channel (e.g., u-shaped channel, or a channel having a lower surface, and two side walls) along which the slider 642 can move or glide during operation. Slider 642 is configurable such that it physically attaches to the elongated sheath 632 and directly controls the longitudinal location and translational movement of sheath 632 in at least one of a proximal and distal direction relative to elongated inner member 634 and the IUD (not shown). In operation, an operator's finger, or, more preferably, thumb, moves the slider 642 along the elongated guide 640.

The slider and elongated guide system is configurable to enable the user to control IUD positioning during the insertion procedure. As shown in FIG. 6B, slider 642 is located in a distal-most starting position during step 1 of the insertion procedure. In step 2, the user moves the slider 642 along elongated guide 640 to a second position (not shown). In step 3, the user moves the slider 642 along the elongated guide 640 to a third position (not shown). Typically, the slider 640 is positioned in a distal position and then moved proximally for steps 2 and 3.

As described above, preserving a smooth, rounded, and low profile tip of the insertion device, as shown in FIGS. 3A-4A, reduces pain and prevents premature deployment of the IUD from the insertion device. Maintaining a proper IUD position and controlling the positions of the IUD, the elongated sheath of the insertion device, and the elongated inner member of the insertion device during insertion process can also alleviate other issues that can arise during the insertion procedure, such as management of the IUD strings. In addition to the slider and elongated guide system described above, the insertion devices of the present disclosure are further configurable to include one or more additional features to improve IUD position control.

Figure 6D:
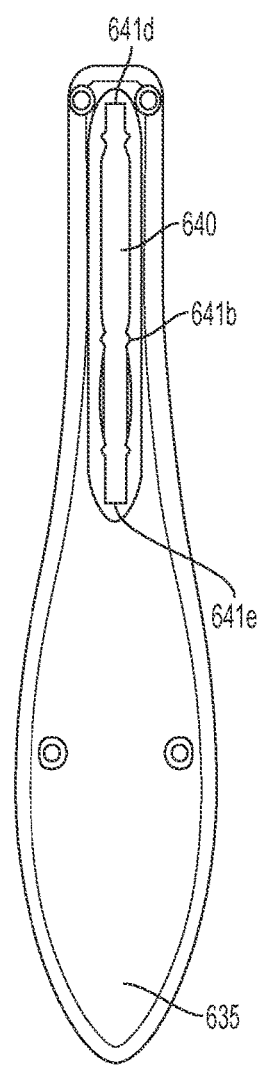

In another aspect of the disclosed devices, the slider, elongated guide, and/or housing are adaptable and configurable to include one or more position control features which can ensure that the slider is maintained at the proper location in each of the phases of the insertion procedure, such as the positions shown in FIGS. 3-5. For example, as shown in FIG. 6C (which depicts the handle without the slider 642 positioned in the elongated guide 640) the position control features 641a, 641b, 641c aid the user in controlling the slider position, thereby positioning the slider in a predefined location corresponding to each procedural step. As illustrated in FIGS. 6c-d, the position control features 641a, 641b, 641c are female indentions configured to mate with male protrusions on the slider (not shown). These position control features are detents that act as a mechanism that temporarily keeps one part (the slider and its attachment) in a certain position relative to that of another (the handle), and can be released by applying force to one of the parts. By precisely controlling the position of the sheath slider of the insertion device, the sheath will be positioned properly relative to the IUD since the sheath slider controls the sheath. Position control features can be "soft stop" features which impede or interrupt an otherwise uniform sliding movement of the slider along the elongated guide.

In some configurations, the soft motion control features (e.g., stop features, position control features, and movement control features) do not rely on hard stop contact surfaces between motion control surfaces of different components of the insertion device (e.g., when the distal end of the sheath slider 642 engages the distal end 641d of the elongated guide 640), such as provided with the detent configuration. For example, the elongated guide soft stops 641a, 641b, 641c are adaptable and configurable to include a decrease in a width w of the elongated guide 640, or a decrease in tolerance between the elongated guide and the slider, whereby increased friction exists between the sheath slider 642 and the housing 635 at different locations along the elongated guide 640 corresponding to a procedural stop or pause—e.g., step 1, 2, or 3 corresponding to IUD positions shown in FIGS. 3A, 4C, and 5C, respectively. The soft stops provide tactile feedback when the sheath slider 642 moves proximally and distally along the length of the channel of the elongated guide 640 without rotation of the sheath slider 642. This configuration could be in lieu of the detent configuration described above. The position control features of the housing, elongated guide, and/or slider can include physical features such as detents, notches, grooves, protrusions, tabs, ridges, flanges, flaps, gates, flexible members, contours, curves, shapes, etc., which are configurable to impede slider movement at the corresponding locations in the housing or elongated guide. Soft motion control features may, for at least some configurations, be advantageous over hard motion control features because the soft motion control features may increase a user's control during operation.

As will be appreciated by those skilled in the art, motion control features can also include "hard stop" features which include physical contact between the slider and the surface of other components of the insertion device to prohibit further movement of the slider in an undesired direction. Typically, hard stops include direct physical contact between two or more device components, whereby the hard stop prohibits further movement of either component past the hard stop point. For example, the insertion device shown in FIG. 6D includes a first hard motion control surface 641d (e.g., stop surface) at the distal end of the elongated guide 640 and a second hard motion control surface 641e at the proximal end of the elongated guide 640. In this configuration, step 1 of the insertion procedure can be defined by physical contact between the slider 642 and the first hard motion control surface 641d, and step 3 of the insertion procedure can be defined by physical contact between the slider (not shown) and the second hard motion control surface 641e. Intermediate stopping can be facilitated with the use of a soft-stop 641b similar to the soft-stop illustrated in FIG. 6c.

When the stopping position for a procedural phase involves a hard motion control feature (e.g., stop features, position control features, and movement control features), the user might be more likely to use excessive speed or force when moving the slider. Hard motion control features might encourage the user to disregard the need for caution, precision, and delicacy, because the user will rely on contact between the hard motion control surfaces for assurance that the procedural step is complete. The user might be more likely to use excessive force and forcefully slam the slider or other position control feature into contact with the hard motion control surface, which could result in disruptive movement of the entire insertion device as a whole and cause pain to the patient or disrupt the insertion procedure. Unlike hard stops, the soft motion control surfaces of the present disclosure encourage the user to exercise caution, precision, and delicacy during the insertion procedure. Further, certain soft stop control features of the present disclosure features can be tactilely felt by the user's thumb or finger, providing a sensory signal to the user corresponding to procedural steps or stopping points. For example, with the device shown in FIG. 6D, the user would not feel the hard motion control surfaces 641d, 641e directly in contact with the user's thumb.

However, as explained in further detail below regarding the device shown in FIGS. 8A-8F, the device has a proximal end 10, a distal end 20, an upper surface 30, a lower surface 40, and at least one side surface 50. When using the devices of the disclosure, the user can feel the housing surfaces 844a, 844b, which are force limiting features, in direct contact with the user's thumb at steps 1 and 3, respectively, as shown in FIGS. 8D and 8F. Although the force-limiting features 844a, 844b of insertion device 800 prevent slider 842 movement beyond the housing surface 844a, 844b, the force-limiting features do not require contact between multiple insertion device components, e.g., between the slider 842 and the housing surfaces 844a, 844b. Additional benefits of soft motion control features will be recognized by persons of skill in the art. For example, soft motion control features can minimize sharp edges of the insertion device and prevent the insertion device from pinching the user.

Position control features of the present disclosure, such as slider features, elongated guide features, and/or housing features, are soft motion control features which provide a soft stop during insertion device operation and merely impede or interrupt the sliding movement of the slider along the elongated guide, thereby contributing to a smooth, uninterrupted sliding motion. However, the features can also include "hard stop" features which prohibit further movement of the slider in an undesired direction.

Alternatively or additionally, the housing or elongated guide can be adapted and configured to include one or more sensory signal features or indicators which provide a sensory feedback to the user that the slider is in the appropriate position corresponding to one or more phases of the insertion procedure. Indication features such as sensory signal features are discussed in further detail below. For example, sensory signal features of the insertion device can include a visual indicator such as a visual alignment feature, an auditory indicator such as a click or other noise heard by the insertion device operator, and/or a tangible indicator feature which can be felt by the operator, such as a tangible indicator felt by the operator's finger or thumb.

The slider can be a sheath slider attached to the elongated sheath for retracting the sheath to deploy the IUD. Alternatively or additionally, the slider can be a plunger slider which is attached to the plunger and pushes the plunger distally to deploy the IUD. The slider can include any appropriate structure which allows the user to move the slider. For example, the slider can include a button, tab, slot, or any suitable interface for moving the slider and the attached sheath or plunger in the appropriate direction. Preferably, the slider glides smoothly along the elongated guide, although it is also preferred that some friction exists between the slider and elongated guide such that the slider will not glide too easily along the elongated guide. Some friction between these components is preferred so that the user has control over the slider movement and the slider will not glide easily or unintentionally along the elongated guide without user-applied force—i.e., the slider will not move in the elongated guide due to mere gravitational force or external motion. As will be understood by persons of skill in the art, the tolerance or spacing between the insertion device components can be adjusted to provide the appropriate amount of frictional force between the components. Such frictional force or resistance exists unanimously or substantially between the slider and the housing or elongated guide rather than between the sheath and the plunger.

Additional elongated guide configurations can be incorporated into any of the insertion devices of the present disclosure. For example, the housing or handle described above is adaptable and configurable to have a variety of elongated guide configurations as shown in FIGS. 7A-7C. For example, for a curved elongated guide 740, as shown in the examples depicted in the figures. In FIGS. 7A-7C, the one or more curves c1, c2, c3, are configurable to correspond to a procedural step such as a stop or pause, whereby the curves provide a soft stop or increased resistance to movement of the slider 742 within the elongated guide 740 or channel. The increased friction between the elongated guide 740 and the slider 742 at the one or more curves c1, c2, c3 of the elongated guide 740 slows the slider 742 motion, thereby creating a soft stop at the one or more curved locations along the length of the elongated guide. The curves c1, c2, c3 in the elongated guide 740 are disposed along the longitudinal axis x of the insertion device handle, whereby the slider moves from side to side as it slides along the elongated guide. As will be appreciated by those skilled in the art, in some configurations, both a side-to-side movement and longitudinal movement are achievable by the slider. In still other embodiments (not shown), the elongated guide curves are disposed at different depths within the handle, whereby the slider moves up and down as it slides along the elongated guide. As will be understood by persons of ordinary skill in the art, the elongated guide can be disposed along any suitable axis of the insertion device. For example, the elongated guide can be disposed along the longitudinal x-axis of the insertion device or along an axis perpendicular thereto. Additionally, as will be understood by persons of ordinary skill in the art, the elongated guide can have any suitable shape not limited to the straight or curved paths shown in the figures and described herein.

Additional aspects for the slider or other position control features are discussed in further detail below. For example, the insertion device is configurable to include multiple sliders for control of multiple insertion device components. For example, the insertion device can have a bilateral configuration such that the slider or other control features can be operated from the top or bottom side of the device housing, thereby allowing for left-handed or right-handed control while still providing the benefits of the improved insertion device of the present disclosure. The insertion device is further adaptable to include additional control features built into the slider itself to allow for added functionality in addition to control of the sheath or plunger movement. For example, the insertion device can include IUD string control features and signal features for indication of procedural steps or IUD location.

As shown in the configuration of the insertion device illustrated in FIGS. 8A-8F, the insertion device 800 of the present disclosure includes an elongated sheath 832, sheath flange 833, an elongated inner member or plunger 834, a slider 842, a string control slider 846, housing 835 including a housing top piece or upper surface 835a and a housing bottom piece or lower surface 835b, and elongated guide 840 wherein the insertion device 800 has a longitudinal axis from a proximal end 10 to a distal end 20. Slider 842 can be integrally formed from a sheath slider, e.g., such that it operates in a unified manner or is constructed or constructable from a single piece, attached to the elongated sheath 832. However, as will be understood by persons of skill in the art, a slider 842 can be attached to the plunger or formed integrally therewith out departing from the scope of the disclosure. The insertion device 800 includes control features for controlling the relative positions of the sheath 832, plunger 834, and IUD (not shown in FIG. 8). Such position control features can include slider features, elongated guide features, and/or housing features, including, but not limited to, any of the features described above. The slider 842 and housing 835 or elongated guide 840 each includes at least one alignment surface, wherein the surfaces become aligned when the slider is positioned at a location corresponding to the appropriate slider position corresponding to a defined step in the IUD insertion procedure. The slider and housing/elongated guide can further be adapted and configured to include multiple alignment surfaces, wherein different slider and/or housing/elongated guide surfaces are differently aligned during different phases of the IUD insertion procedure—e.g., at different locations along the elongated guide, at different phases of the insertion procedure, or at different times during the insertion procedure.

Figures 8A, 8B:
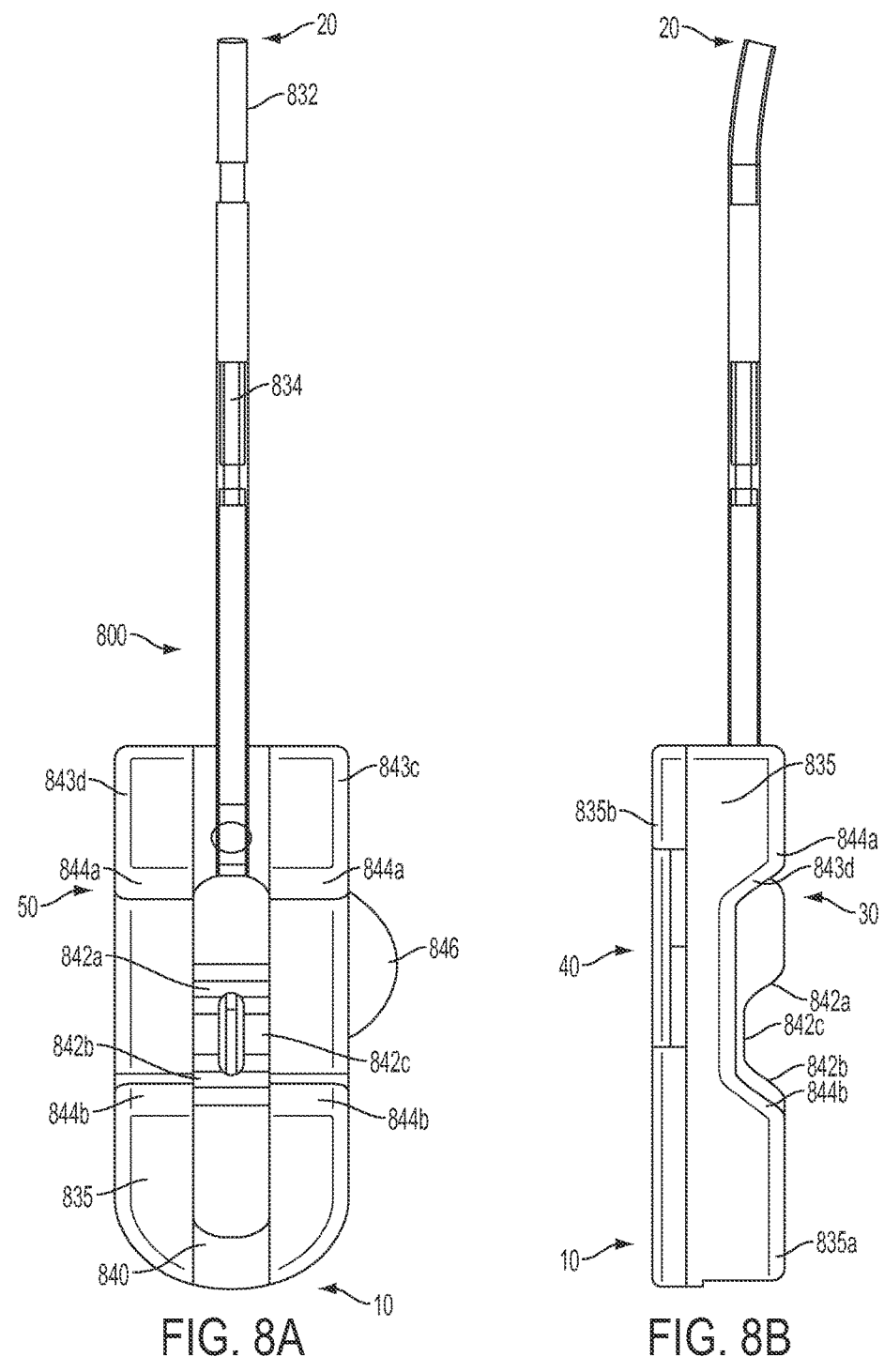
FIGS. 8A illustrates a top view, and 8B illustrates a side view of an insertion device.
Figure 8C:
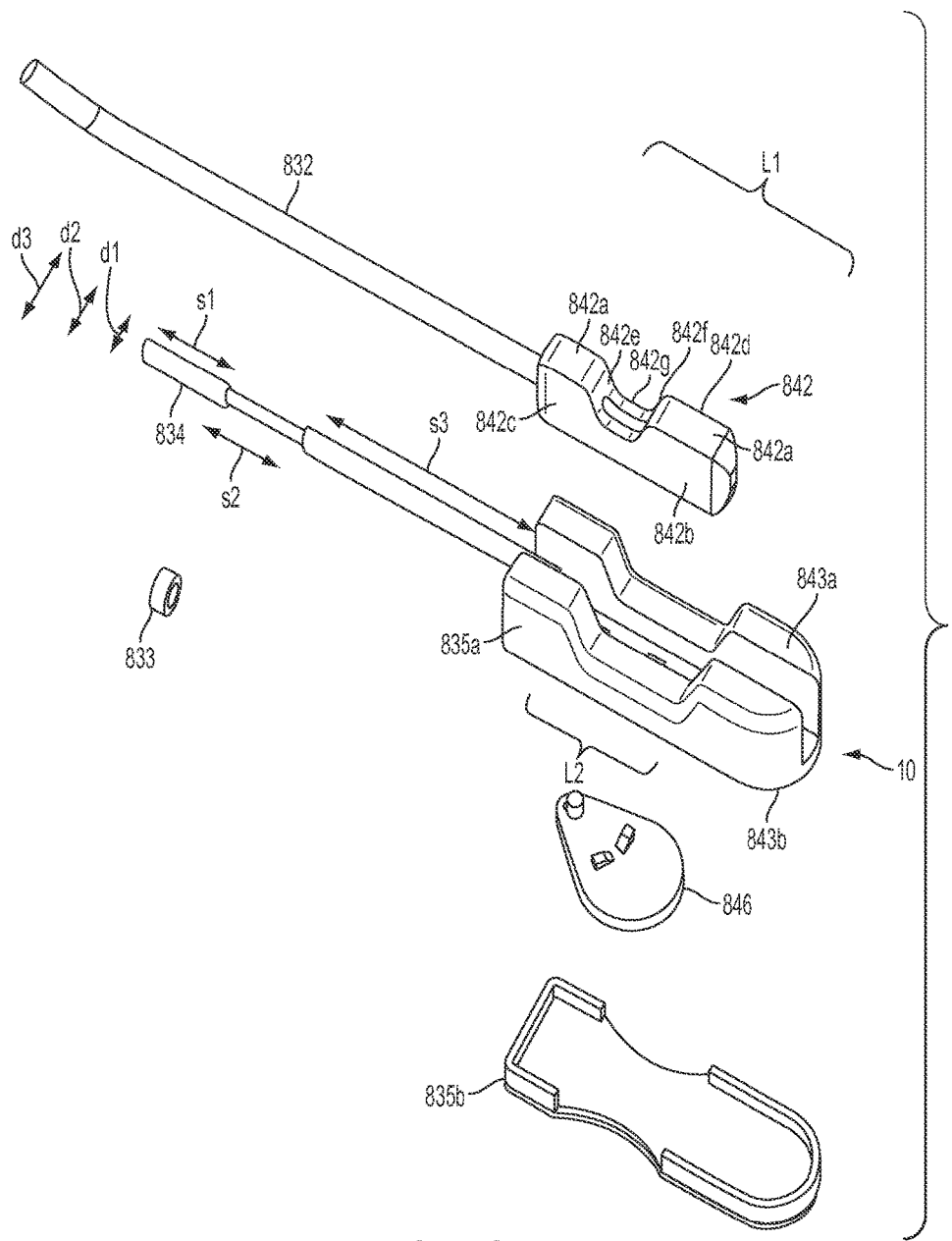
FIG. 8C illustrates an exploded view of the device of FIGS. 8A-8B, showing individual components and a method of assembling the device.
Figure 8D:
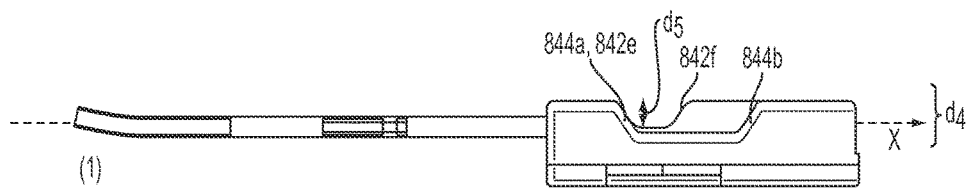
FIGS. 8D-8F show a side view of the device with slider in different positions.

Turning to FIG. 8C, the sheath 832 engages the slider 842 at the proximal end 10 of the sheath and the distal end 20 of the slider mechanism. The slider 842, as depicted, has a recess which has an upper surface 842a, a lower surface 842b, and two side surfaces 842c, 842d. The upper surface 842a is further characterized by an indentation having a length L1 and sized sufficiently to communicate with user's finger during use. The indentation is further characterized by a first side surface 842e, a second side surface 842f which faces the first side surface 842e, and a lower surface 842g. The plunger 834 engages the housing 835 at the proximal end 10 of the plunger 834 and the distal end of the housing 835. The plunger 834 is an elongated shaft having a first diameter d1 along a distal section s1, second diameter d2 along a penultimate section s2, different than the first diameter d1, and a third diameter d3 along a proximal section s3, which is greater than the second diameter and may be the same as the first diameter. The housing 835, as depicted, has an upper surface 843a, a lower surface 843b, and two side surfaces 843c, 843d. The upper surface 843a is further characterized by an indentation having a length L2 greater than the length L1 of the slider. The indentation or channel is defined by a first side surface 842a, a second side surface 842b which faces the first side surface 842a, and a lower surface 842c. As depicted in the configuration of FIG. 8, the width of the slider 842 is such that it fits within an elongated channel 840 of the housing 835.

Figure 8E:
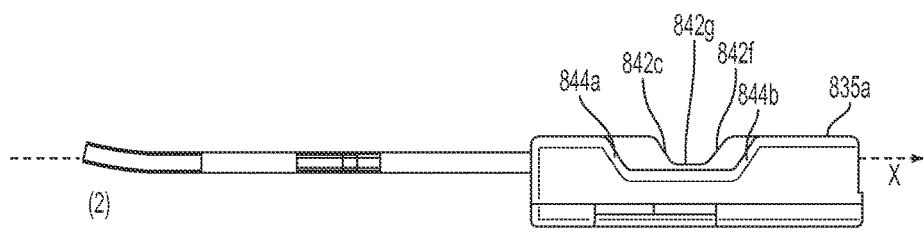
Figure 8F:
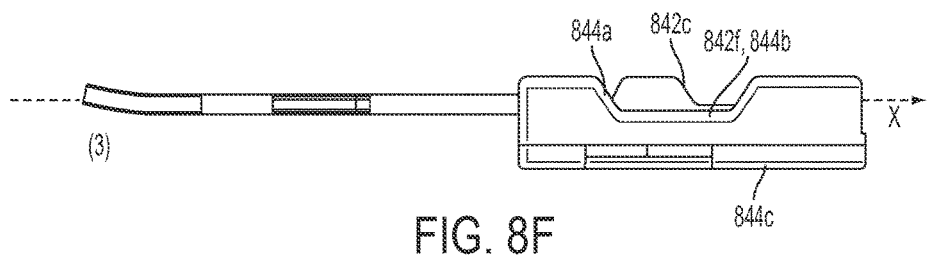

In the configuration illustrated in FIGS. 8A-F, slider 842 has a recess that includes at least a first slider surface 842e and at least a second slider surface 842f, and housing 835 having a recess which includes at least a first surface 844a and at least a second surface 844b. FIGS. 8D-8F illustrate these position control features of the slider 842 and housing 835 during the different phases of an IUD insertion procedure. Each of the slider 842 and the housing 835 have a recess into which a user's thumb fits. The length of the recess of the slider 842 is shorter than the recess of the housing 835, but the depth from the top surface is aligned. FIG. 8D corresponds to step 1, FIG. 8E corresponds to step 2, and FIG. 8F corresponds to step 3 of the insertion procedure described above. As the slider 842 is moved along a longitudinal axis x of the insertion device 800, between the proximal end 10 and the distal end 20, during the various phases of IUD insertion, slider 842 surfaces 842e, 842f are configured to align with one of the housing surfaces 844a, 844b during at least one step of the procedure. In step 1, the first slider surface 842e of the slider recess is aligned with the first housing surface 844a of the housing recess, while the second slider surface 842f and the second housing surface 844b are not aligned. In step 3, the second slider surface 842e of the slider recess is aligned with the second housing surface 844b of the housing recess, but the first slider surface 842f and the first housing surface 844a are not aligned. While only two alignment points are shown in FIGS. 8D-8F, fewer or more than two alignment points are envisioned by the present disclosure. For example, the insertion device can further include additional slider and/or housing surfaces which are aligned at step 2 of the insertion procedure. Lower surface 842g of the slider 842 and lower surface 844c of the housing are configurable such that the depths d4 (the depth established between 835a and 844c), d5 (the depth established between 842a and 842g) relative to the upper surfaces 835a, 842a of the housing 835 and the slider 842 are the same or similar.

When the respective features (e.g., surfaces 842, 844 of the recesses of each of the slider 842 and the housing 835) are aligned during use, such alignment indicates to the user that the IUD is in the proper location corresponding to the corresponding procedural step. The position control features can be configured such that the features are force-limiting (or force-absorbing) features which restrain or prohibit further movement of the slider past designated locations in the elongated guide. The features are also configurable to prevent the user from applying excessive force to the slider, which could interfere with the IUD positioning or even cause damage to the insertion device.

Figure 9A:
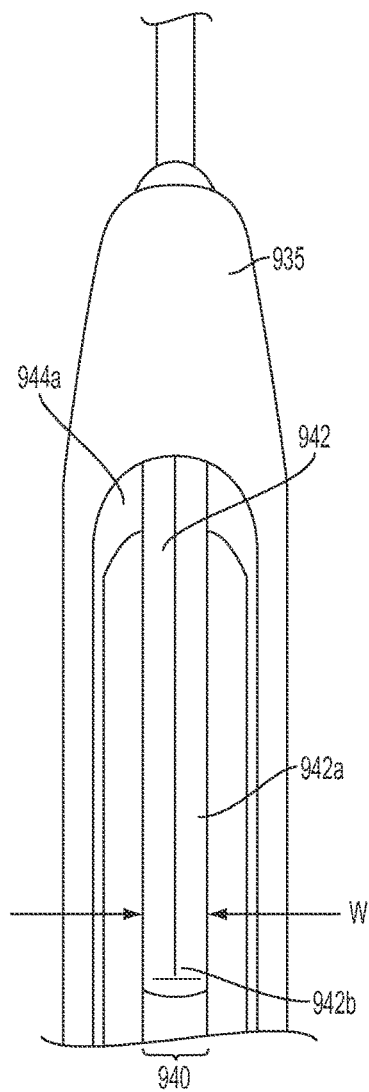
FIGS. 9A and 9B illustrate position control features of an insertion device.
Figure 9B:
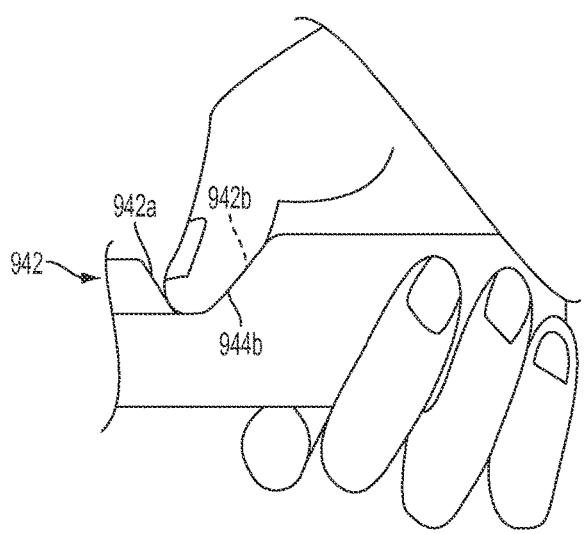

As shown in FIGS. 9A-9B, the proximal end of an insertion device is illustrated where the width w of the sheath slider 942 and/or elongated guide 940 is sufficiently narrow such that the user's finger or thumb fits within a recess illustrated in FIG. 9B and can control and move the slider 942 along the elongated guide 940 without the ability to move the slider 942 past the force-limiting features on the handle 935 or elongated guide 940. For example, in one aspect, the elongated guide 940, slider 942, and slider surfaces 942a, 942b each has a width which prevents the user from moving the slider 942 past the force-limiting features 944a, 944b of the handle 935 housing. This limited width prevents the user from moving the slider past the alignment points.

The force-limiting features improve IUD position control by preventing the user from moving the IUD out of the appropriate position. For example, in step 1 corresponding to FIG. 8D and FIGS. 3A-3D, the force-limiting feature 844a prevents user-applied force to the slider from moving the slider past the force-limiting feature 844a when the surfaces of the recesses align. Since the user's thumb cannot fit through the elongated guide past the force-limiting feature 844a, the user's thumb abuts the force-limiting feature 844a and the slider 842 will not move distally. As shown in FIGS. 9A-9B, the user's thumb is prevented from moving beyond the force-limiting features 944a and 944b due to the narrow width w of the slider 942 and the elongated guide 940. Preferably, the width of the elongated guide 940 or slider 942 (or the combined width of multiple sliders) is 0.75 inches (19 mm) or less, 0.7 inches (17.8 mm) or less, 0.5 inches (12.7 mm) or less, 0.35 inches (8.9 mm) or less, or 0.25 inches (6.3 mm) or less.

Any excessive force applied to the slider by the user will be completely transferred to or absorbed by the stationary force-limiting feature. As an additional benefit, the force-limiting features, such as force-limiting features 844a and 844b, prevent undesirable movement of the entire insertion device as a whole during the insertion procedure. As mentioned above, the alignment or coinciding of the slider and housing features can provide a signal to the user which indicates that the IUD is in the proper location corresponding to the corresponding procedural step.

As will be appreciated by those skilled in the art, additional features and mechanisms in addition to the surfaces, recesses, and alignment discussed above, can be used for position control and are envisioned by the present disclosure. The control features can include additional or different characteristics, as will be understood by a person of skill in the art. Such position control features of the slider, housing, and/or elongated guide can include physical attributes such as shapes, distinctive physical features, angles, contours patterns, colors, sizes, or visual symbols, which aid the user in precisely controlling the IUD position throughout the insertion procedure. For example, the features could be misaligned when the defined procedural steps occur and aligned at other times—i.e., misaligned at defined procedural steps 1, 2, and/or 3, and aligned at times between said steps. The mechanical features could also be configured to coincide in a manner other than by alignment of the surfaces or other physical features. In certain aspects, when a defined procedural step is achieved such that a slider is in the appropriate corresponding position, an insertion device can display a visual signal to the user which appears only when the slider is in the proper location corresponding to such procedural step. For example, the insertion device could display a visual indicator symbol such as a picture, word, character, number, pattern, color change, etc., whenever the slider location corresponds to a procedural step (or whenever the slider location does not correspond to a procedural step). Indication features of the insertion device of the present disclosure are discussed in further detail below.

The present devices can be configured to include a handheld insertion device adapted and configured to insert an IUD or IUS comprising an elongated inner member, an elongated sheath at least partially encasing or surrounding the elongated inner member, and one or more control features for controlling various features of the insertion device. The control features are further adaptable and configurable to include at least one control feature which controls the translational movement of the elongated sheath and the elongated inner member relative to one another along the longitudinal axis, and at least one control feature for controlling one or more string components of the IUD during the insertion procedure and/or post-insertion. String control features, mechanisms, and methods of the present disclosure are discussed in further detail below. As will be appreciated by persons of skill in the art, any such string control features, mechanisms, and methods can be used in combination with the various insertion device designs discussed herein.

In one aspect of the insertion device of the present disclosure, as illustrated by the example in FIGS. 10A-10F, the insertion device 1000 having a proximal end 10 and a distal end 20 comprises a handheld insertion device comprising an elongated inner member or plunger 1034, an elongated sheath 1032, a handle or housing 1035, a sheath slider 1042 projecting or extending from an upper and/or lower surface of the housing 1035 and adapted and configured to control the translational movement of the elongated sheath 1032 and the elongated inner member relative to one another along their longitudinal axes in one or more of a proximal and/or distal direction, and at least one string control feature for controlling one or more strings attached to the IUD (shown and described above with respect to FIG. 2). The insertion device 1000 has a longitudinal axis from a proximal end 10 to a distal end 20. A string control feature can include, for example, a string control slider 1046, as shown in FIGS. 10A-10F. As explained in further detail below, the string control slider 1046 is adaptable and configurable to control securement of the strings, e.g., by allowing locking and unlocking of one or more strings attached to the IUD.

Figure 10A:
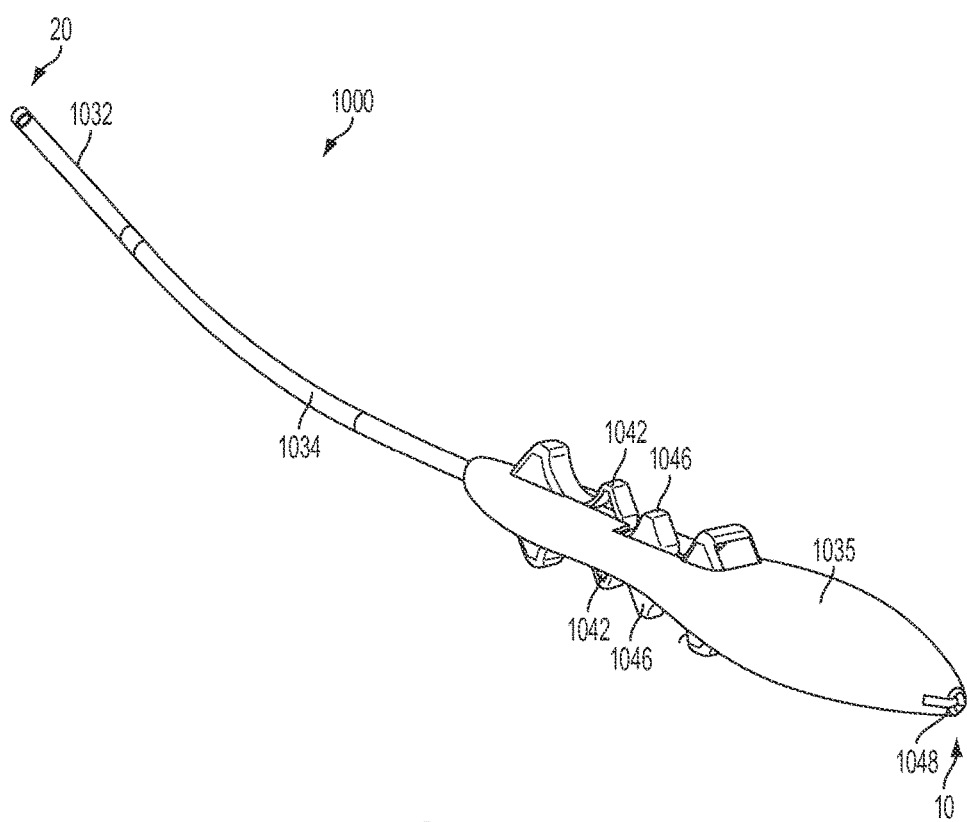
FIG. 10A illustrates perspective view of an insertion device.

The insertion device housing 1035 provides a housing for the proximal end of insertion device parts such as the sheath 1032, plunger 1034, and slider 1042. Each of the slider 1042 and the string control slider 1046 have a curved surface forming a recess into which a user's thumb fits as shown in FIG. 10C. Additionally, the housing 1035 forms a handle configured for an operator to hold the insertion device during use. The housing 1035 includes one or more slider windows or elongated guides 1040a, 1040b which allow user access to sliders 1042, 1046. A first elongated guide 1040a provides a guide along which the sheath control slider 1042 can glide or move during operation. A second elongated guide 1040b provides a guide along which the string control slider 1046 can glide during operation. Slider 1042 can be a sheath slider which is physically attached to sheath 1032 and is adapted and configured to control the longitudinal location and translational movement of sheath 1032 relative to inner member 1034 and the IUD. In an insertion procedure, the operator's thumb is used to move sliders 1042, 1046 along their respective elongated guides 1040a, 1040b which are positioned adjacent to each other and may be partially or completely overlapping to control both the elongated sheath 1032 and the IUD strings (not shown in FIG. 10), respectively.

Figure 10B:
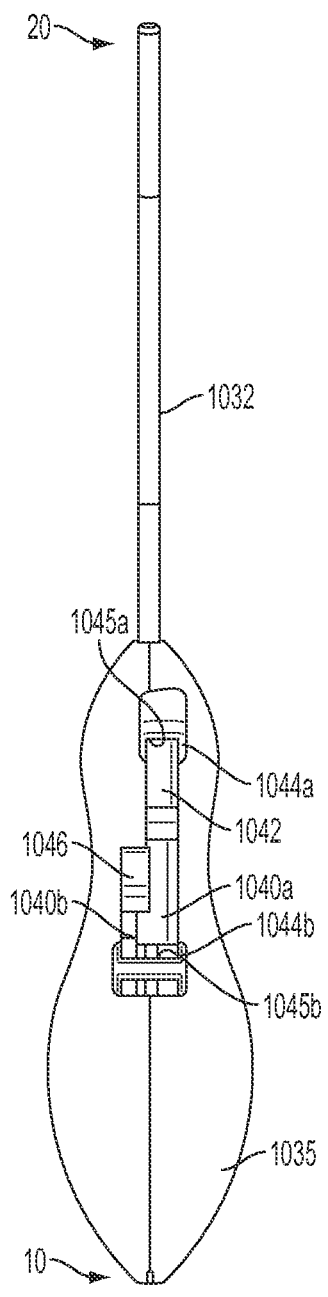
FIG. 10B illustrates a top view.
Figure 10C:
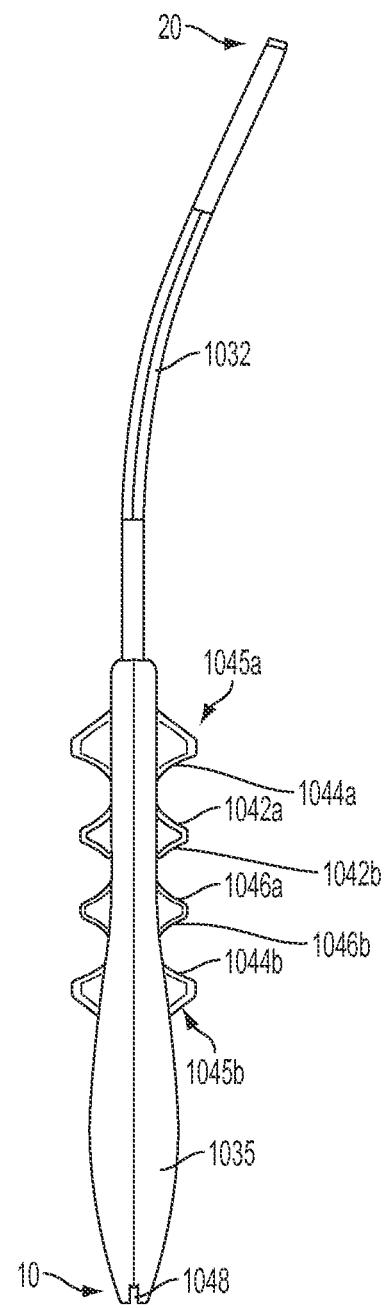
FIG. 10C illustrates a side view of an insertion device shown in FIG. 10A.

As can be seen in FIG. 10B, the insertion device 1000 includes a bilateral configuration, wherein the side-by-side sheath control and string control sliders 1042, 1046 are accessible from either the top (upper) or bottom (lower) surface of the housing/handle 1035. Bilateral configuration of the sliders 1042, 1046 allows for both left-handed and right-handed users to operate the insertion device in the same manner. The sheath 1032 comprises a flexible yet rigid material which is shapeable or moldable to each patient's unique anatomy. Insertion device 1000 is further configurable to include one or more force-limiting features 1044a, 1044b adapted and configured to prevent the user from applying excessive force to the sliders 1042, 1046. The one or more force-limiting features 1044a, 1044b can be configured such that the features extend either one or both of above and below either or both of the upper and lower surface of the housing. The force-limiting features 1044a, 1044b can also be formed integrally with the housing 1035, as shown in FIG. 10A-10B. In at least some configurations, at least one said force-limiting feature functions as a soft stop rather than as a hard stop, whereby user-applied force is limited by the force-limiting feature without requiring contact between insertion device components or insertion device component surfaces. Rather, the force-limiting feature limits user-applied force applicable to the one or more sliders by impeding or prohibiting the user's finger from moving the slider past a certain point along the longitudinal axis. For example, as shown in FIG. 10C, the insertion device 1000 includes a sheath control slider 1042 having a first surface 1042a and a second surface 1042b, a string control slider 1046 having at least a first surface 1046a and a second surface 1046b, and a housing 1035 having a first surface 1044a and a second surface 1044b. The housing 1035 includes at least one force-limiting feature corresponding to the housing surfaces 1044a, 1044b.

As will be appreciated by those skilled in the art, the force limiting feature prevents the slider from continuing motion in a distal (forward) direction when the force limiting feature(s) are engaged, e.g., when the surfaces of the features are aligned. Without the force limiting feature, the slider would continue distal (forward) movement.

Figure 10D:
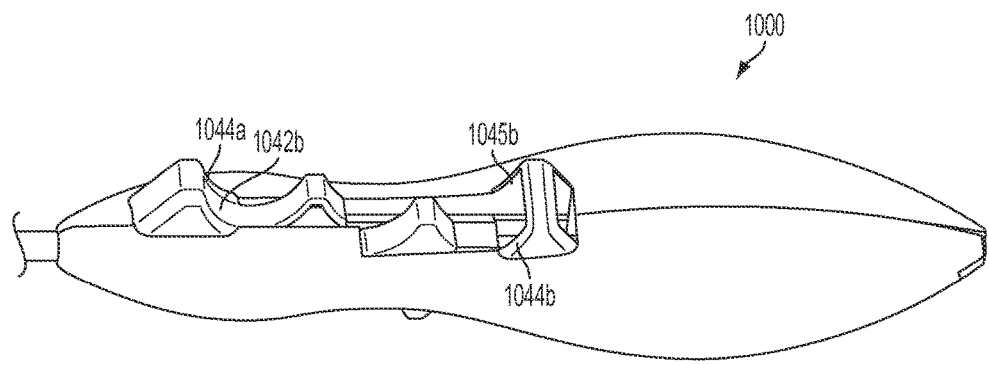
FIGS. 10D-10F illustrate operational positioning of the insertion device during a first, second, and third phase of an IUD insertion procedure.
Figure 10E:
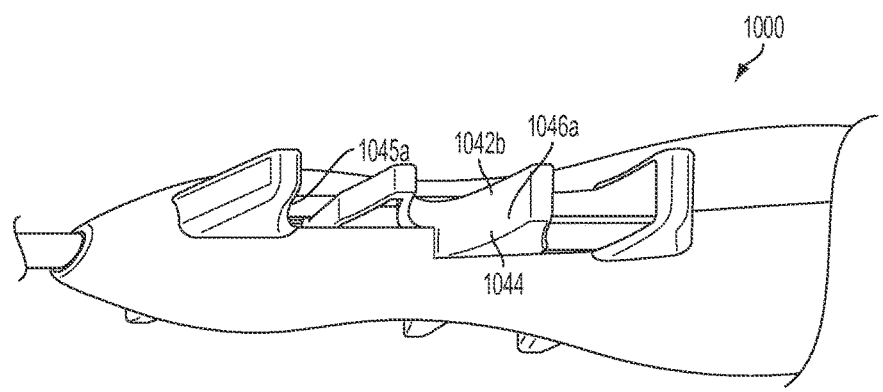
Figure 10F:
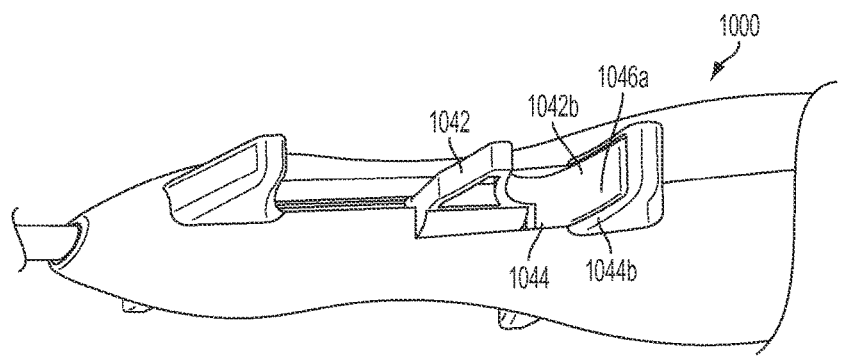

As shown in FIGS. 10A-10F, the bilaterally operative insertion device 1000 can further be configured to comprise a housing 1035 which includes one or more garage, aperture, cavity, or opening features which surround or cover at least a portion of one or more sliders 1042, 1046 at one or more positions during certain phases of the insertion procedure. For example, as shown in FIGS. 10D-E, the distal and proximal force-limiting features of the housing 1035 each comprises a cavity 1045a, 1045b. In step 1 of the insertion procedure, the sheath slider 1042 is located in the first cavity 1045a, near the distal end of the sheath elongated guide 1040a. In step 3 of the insertion procedure, both the sheath slider 1042 and the string control slider 1046 are located in the second cavity 1045b, near the proximal end of the elongated guides 1040a, 1040b. Insertion device 1000 further comprises one or more alignment features, such as surface features of the one or more sliders and housing or elongated guides. As shown in FIG. 10D, the housing includes a first surface 1044a at the distal end of the sheath elongated guide 1040a and a second surface 1044b at the proximal end of the sheath elongated guide. The sheath slider 1042 includes a first surface 1042a and a second surface 1042b. As shown in FIGS. 10E-F, the string control slider 1046 includes a first surface 1046a and a second surface 1046b. As mentioned above, the alignment or coinciding of the slider and housing features can provide a signal to the user which indicates that the IUD is in the proper location corresponding to the corresponding procedural step. For example, alignment/position control surfaces 1044a and 1042b are aligned at step 1, as shown in FIG. 10D. Surfaces 1042a and 1046a are aligned at step 2, as shown in FIG.

10E. Surfaces 1042*a*, 1046*a*, and 1044*b* are aligned at step 3, as shown in FIG. 10F. As described above, the force-limiting features and the alignment features are soft motion control features which do not require physical contact between the insertion device features or components. Such a soft motion control feature prevents undesirable movement of the insertion device during the insertion procedure and promotes smooth user movements without disruptions caused by components of the insertion device contacting one another.

As shown in FIGS. 10C-10F, the alignment of the position control features or alignment surfaces corresponds to defined procedural steps and corresponding IUD positions. Additionally, alignment of these features provides a force-limiting mechanism to prevent further slider movement caused by user-applied force. As shown in FIG. 10D, corresponding to the insertion device 1000 configuration during step 1 of the insertion procedure, the sheath slider is in the full distal position along the longitudinal axis of the elongated guide. The sheath slider first surface 1042*a* is aligned with the housing first surface 1044*a*, whereby the user's finger can simultaneously contact both aligned surfaces 1042*a* and 1044*a*. The housing first surface 1044*a* is a force-limiting feature, whereby the user's finger will abut the housing first surface 1044*a*, and the user is prevented from sliding the sheath slider 1042 past the force-limiting feature 1044*a*. Preferably, the combined width of both sliders is sufficiently narrow to prevent the user's finger from entering either of the cavities 1045*a*, 1045*b*.

As shown in FIG. 10E, corresponding to the insertion device configuration during step 2 of the insertion procedure, the sheath slider and string control slider are each in a middle position along the longitudinal axis of the elongated guide. During steps 1 and 2, the string control slider can be disposed in a separate elongated guide 1040*b*, and the string control slider can be positioned in the full distal position of the elongated guide 1040*b*. As the user slides the sheath slider 1042 backward along the elongated guide, the sheath slider 1042 approaches the string control slider 1046. Eventually, the sheath slider 1042 second surface 1042*a* and the string control slider first surface 1046*a* are aligned, signifying that the IUD is in the appropriate position corresponding to step 2.

As shown in FIG. 10F, corresponding to the insertion device 1000 configuration during step 3 of the insertion procedure, the sheath slider 1042 and string control slider 1044 are in the full proximal position along the longitudinal axis of the elongated guides 1040*a*, 1040*b*. The sheath slider second surface 1042*b* is aligned with the string control first surface 1048*a*, and the user simultaneously slides both the sheath slider and string control slider 1048 backward toward the housing second surface 1044*a*. Upon reaching step 3 of the insertion procedure, the user's finger contacts both aligned surfaces 1042*b* and 1046*a*, as well as the housing second surface 1044*b*. The housing second surface 1044*b* is a force-limiting since the user's finger abuts the housing second surface 1044*b* and the user is thereby prevented from sliding the first sheath slider surface 1042*a* and the first string control slider surface 1046*a* past the force-limiting feature 1044*b*.

The sheath slider 1042 and string control slider 1046 are configurable such that they may but need not be physically attached to one another, Moreover, the sheath slider 1042 and string control slider 1046 are configurable so that they can translate or slide freely and independently of one another. The combined width of the sheath slider 1042 and string control slider 1046 has a width sufficient to allow a user's finger or thumb to control and move the sliders along their respective elongated guides 1040*a*, 1040*b*. In at least some configurations, the control and movement of the sliders is performed simultaneously. The housing 1035 includes one or more garage, cavity, or opening which is configured to surround or covers at least a portion of one or more sliders. For example, as shown in FIG. 10C, force-limiting features 1044*a* and 1044*b* of housing 1035 each comprise a cavity 1045*a*, 1045*b*. In step 1 of the insertion procedure, the sheath slider 1042 is at least partially positionable within the first cavity 1045*a* during at least part of the procedure, near the distal end of the elongated guide. In step 3 of the insertion procedure, the sheath slider 1042 and string control slider 1046 are both at least partially positionable within a second cavity 1045*b*, near the proximal end 10 of the elongated guides 1040*a*, 1040*b*. As described above, force-limiting features of the insertion device 1000 can be soft motion control features which do not require physical contact between the insertion device features. Such a soft motion control feature prevents undesirable movement of the insertion device during the insertion procedure and promotes smooth user movements without disruptions caused by components of the insertion device contacting one another. Additionally, the alignment or coinciding of the slider and housing features can provide a signal to the user which indicates that the IUD is in the proper location corresponding to the corresponding procedural step.

Figure 11:
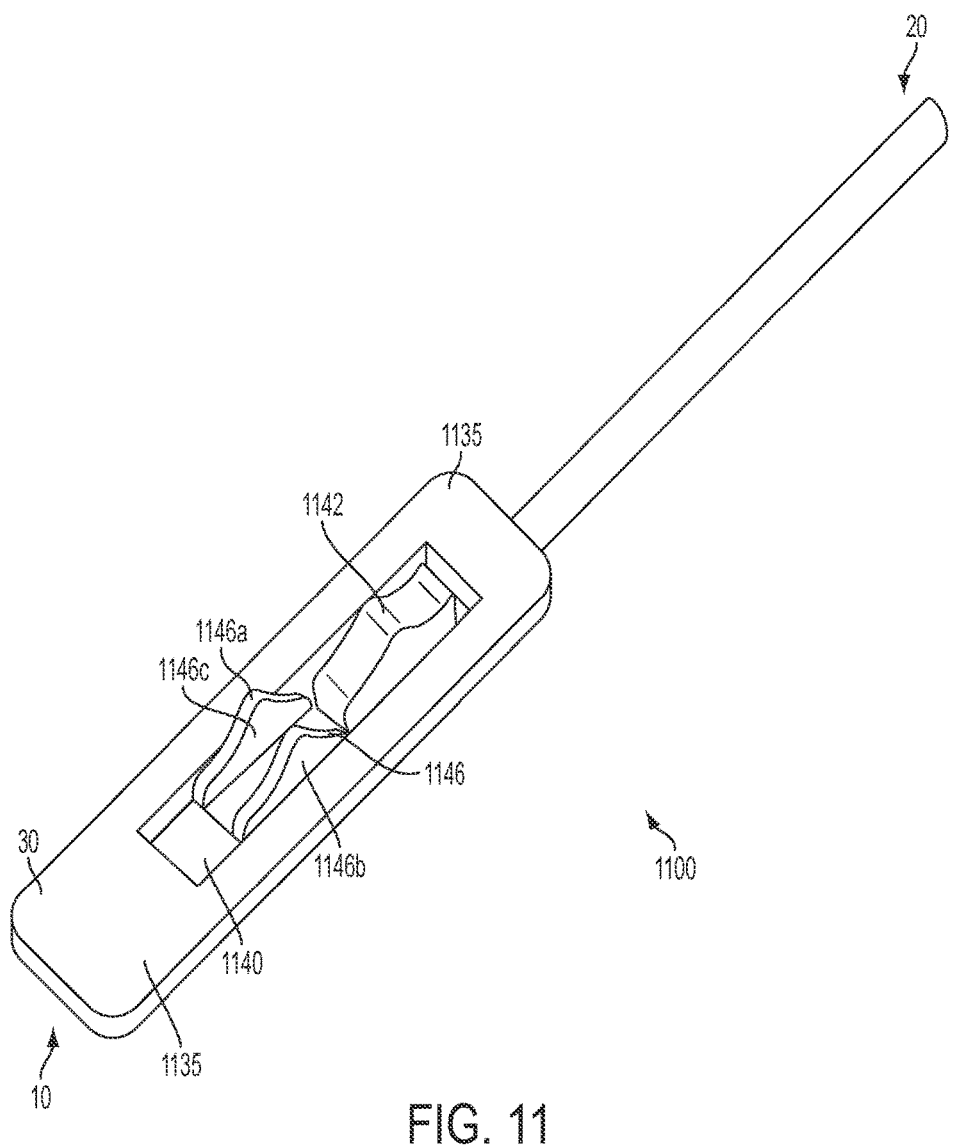
FIG. 11 illustrates an insertion device having multiple sliders.

As shown in FIG. 11, the distal (forward) limit of the sheath slider movement is configurable such that the distal end 20 of the sheath control elongated guide 1140, and the proximal limit of the sheath control slider 1142 movement is defined by the proximal end 10 of the sheath control elongated guide 1140. As with other configurations, the insertion device has a longitudinal axis from a proximal end 10 to a distal end 20. In addition to the sheath control elongated guide 1140, the insertion device 1100 further comprises a string control slider 1146 which has a curved distal surface and is adaptable and configurable to move within the elongated guide 1140. The string control slider 1146 is configured such that it has two protrusions 1146*a*, 1146*b*, with an interior surface 1146*c*, extending above the upper surface 30 of the handle 1135. A channel 1136*c* is formed in the string control slider 1146 between the two protrusions 1146*a*, 1146*b*. When the user slides the sheath control slider 1142 proximally to the position where the user's thumb contacts both the sheath control slider 1142 and the string control slider 1146 when the surfaces align, the sheath control slider 1142 is dimensioned such that it can slide between the channel 1136*c* formed in the string control slider 1146. When the sheath control slider 1142 and the string control slider 1146 are both advanced in a distal most direction 20, the sheath control slider fits within the channel of the string control slider 1146 such that the two sliders create a single profile extending from the housing 1135. Moreover, alignment of both sliders sends feedback to the user that the sheath control slider is in the appropriate position for step 2. The feedback can be tactile, visual, or audible. When the user slides the sheath control slider 1142 and string control slider 1146 simultaneously during the transition from step 2 to step 3 of the insertion procedure, both sliders 1142, 1146 contact the distal end of the elongated guide 1140, thereby prohibiting the user from further movement of the sliders in the distal direction. Distal movement of the sheath slider 1142 is also impeded since the sheath control slider 1142 and string control slider 1146 are moved simultaneously by the user. This mechanism sends feedback to the user, indicating that step 3 of the insertion procedure has been accomplished.

In another example, the insertion device includes multiple sheath sliders or multiple string control sliders. Thus, for example, the string control slider 1146 can be formed from two distinct sliders 1146b, 1146c which are configured to operate independently and wherein each slider controls one of the two strings on the IUD device.

Figures 12A, 12B:
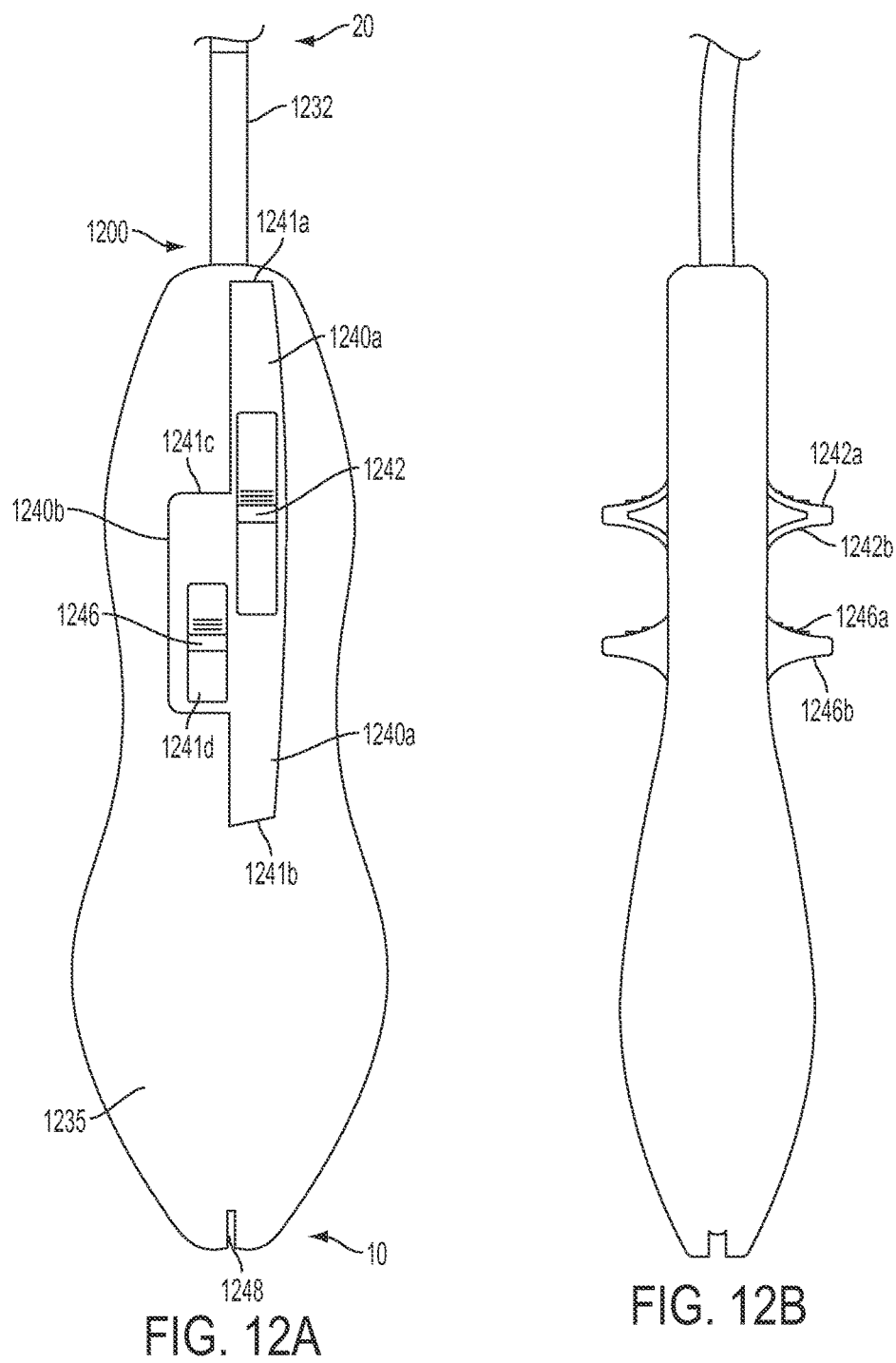
FIG. 12A illustrates a top view and FIG. 12B illustrates a side view of an insertion device.

In yet another aspect, as shown in FIGS. 12A-12B, the insertion device 1200 which has an elongated sheath 1232 and a handle 1235, includes a sheath slider 1242, having a first sheath slider surface 1242a and a second sheath slider surface 1242b, and a string control slider 1246, having a first string control slider surface 1246a and a second string control slider surface 1246b, in the handle 1235. The insertion device 1200 has a longitudinal axis from a proximal end 10 to a distal end 20. As in the configuration depicted in FIGS. 10A-10F, the sheath slider 1242 slides in a proximal 10 and a distal 20 direction along a pathway defined by a first elongated guide 1240a, and the string control slider 1246 is moveable along a pathway defined by a second elongated guide 1240b. Each of the sheath slider 1242 and the string control slider 1246 have a curved surface forming a recess into which a user's thumb fits as shown in FIG. 12B. In this aspect, the distal and proximal limits of movement for the sliders 1242, 1246 can include elongated guide features such as hard motion control surfaces 1241a, 1241b, 1241c, 1241d, rather than the cavities of insertion device 1000 illustrated in FIGS. 10A-10F. The distal limit for movement of the sheath slider 1242 is the hard motion control feature 1241a of elongated guide 1240a, and the proximal limit for movement of the sheath slider 1242 is the hard motion control feature 1241b of elongated guide 1240a. The distal limit for movement of the string control slider 1246 is the hard motion control feature 1241c of elongated guide 1240b, and the proximal limit for movement of the string control slider is the hard motion control feature 1241d of elongated guide 1240b.

In step 1 of the insertion procedure (position not shown), the sheath slider 1242 is in the distal most position at the hard motion control feature 1241a of elongated guide 1240a, and the string control slider 1246 is the distal most position at the hard motion control feature 1241c of elongated guide 1240b. In step 2 of the insertion procedure (position not shown), the sheath slider 1242 is in a median position, positioned somewhere along the length of the elongated guide, with the string control slider 1246 which is in the full distal position at the hard motion control feature 1241c of elongated guide 1240b. In step 3 of the insertion procedure (position not shown), the sheath slider 1242 and string control slider 1246 are aligned and located at the proximal hard motion control feature 1241d of elongated guide 1240b. Although the proximal limit of movement for the sheath slider 1242 is configured as a proximal hard motion control feature 1241b of the sheath control elongated guide 1240a, the insertion procedure is complete at step 3 when the sheath slider 1242 is aligned with the proximal hard motion control feature 1241d of elongated guide 1240b. An optional hollow area, indentation, cleft or cleavage 1248 can be provided in a proximal surface of the handle 1235 into which one or more strings can be held.

As will be understood by persons of skill in the art, the insertion devices of the present disclosure can include any suitable combination of position control features, including, but not limited to hard motion control features, soft motion control features, force-limiting features, cavities, or the like. For the sake of clarity and conciseness, all possible combinations of such features are not discussed in detail herein, but such combinations are included in the insertion device of the present disclosure.

The insertion devices of the disclosure are also configurable to include a handheld IUD insertion device further comprising an elongated inner member, an elongated sheath at least partially encasing or surrounding the elongated inner member, and one or more control features for controlling various features of the insertion device. Control features include, but are not limited to, at least one control feature which controls the translational movement of the elongated sheath and the elongated inner member relative to one another along the longitudinal axis in one or both of a proximal and distal direction, and at least one control feature for controlling one or more strings attached to the IUD during the insertion procedure and/or post-insertion. The sheath slider and string control slider are configured such that the sliders have a telescopic configuration. The string control features, mechanisms, and methods of the present disclosure are discussed in further detail below. As will be appreciated by persons of skill in the art, any such string control features, mechanisms, and methods can be used in combination with the various insertion device configurations discussed herein.

Figure 13A:
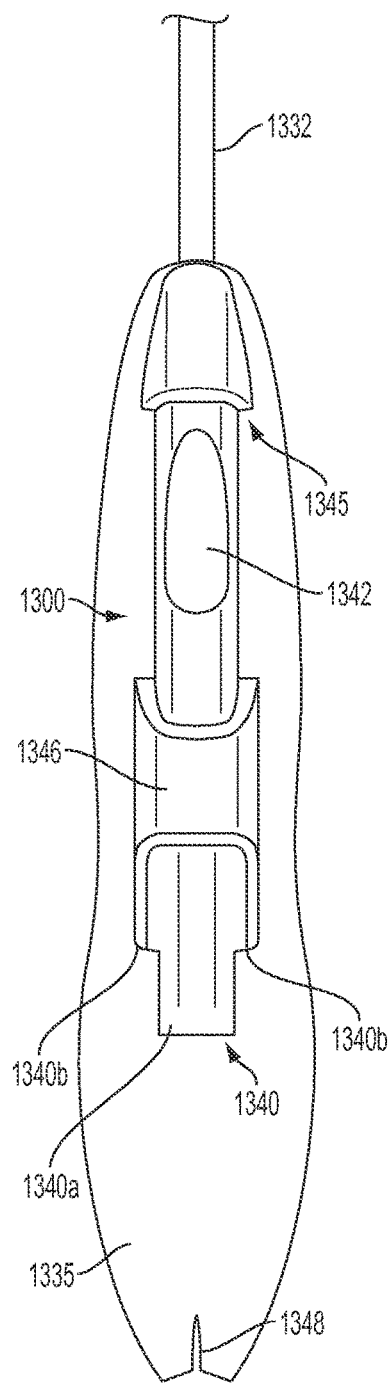
FIG. 13A illustrates a top view and FIG. 13B illustrates a side view of an insertion device with telescoping sliders.
Figure 13B:
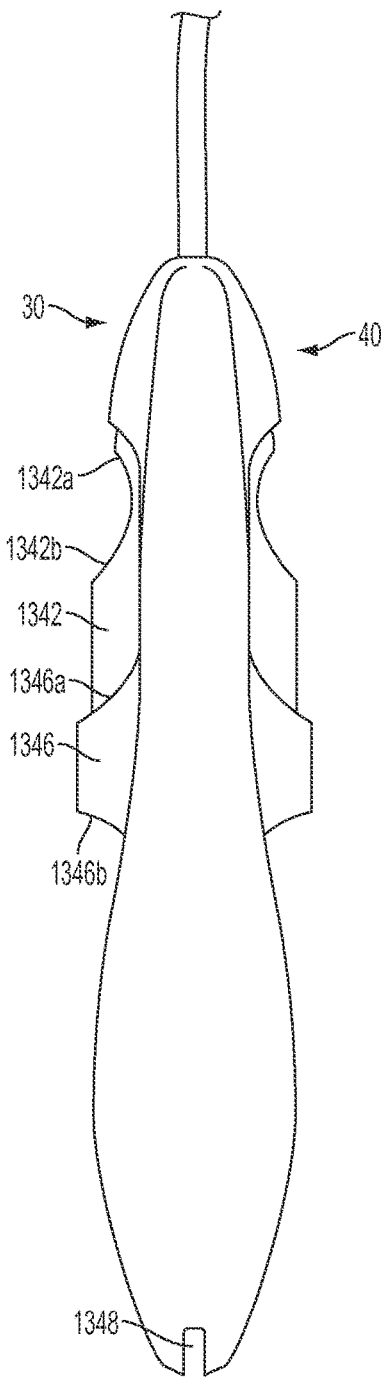

As illustrated by the example in FIGS. 13A-13B, the insertion device 1300 comprises an elongated sheath 1332, an elongated inner member or plunger (not shown), a handle or housing 1335, at least one elongated guide, a first slider 1342 having a depression with a first slider surface 1342a and a second slider surface 1342b, for controlling the translational movement of the elongated sheath 1332 and the elongated inner member relative to one another along their longitudinal axes, and a string control slider 1346, having a first string control slider surface 1346a and a second string control slider surface 1346b, for controlling one or more strings attached to the IUD. The insertion device 1300 has a longitudinal axis from a proximal end 10 to a distal end 20. Each of the first slider 1342 and the string control slider 1346 have a curved surface forming a recess into which a user's thumb fits as shown in FIG. 13B. The string control feature can include a string control slider 1346, as shown in FIGS. 13A-13B. As explained in further detail below, the string control slider 1346 can control the locking and unlocking of one or more strings attached to the IUD. The insertion device housing 1335 is adaptable and configurable to provide a housing for insertion device parts such as the sheath 1332, plunger, and sliders 1342, 1346, and provides a handle for the operator to hold the insertion device during operation. The housing 1335 is further adaptable and configurable to include a slider window or elongated guide which allows user access to the sliders 1342, 1346. The elongated guide can be configured as illustrated in FIGS. 13A-B to include multiple elongated guides 1340a, 1340b which provide a guide 1340 along which the sliders 1342, 1346 can glide during operation. As will be appreciated by those skilled in the art, movement of the sliders along the one or more elongated guide can be one or more of concurrent or independent, at any given time during the procedure. As illustrated, slider 1342 is a sheath slider which is attachable to sheath 1332 and directly controls the longitudinal location and translational movement of the sheath 1332 relative to the elongated inner member and IUD. Slider 1346 is a string control slider (e.g., a string-unlocking or string release slider). In an insertion procedure, the operator's thumb is used to move both sliders 1342, 1346 proximally and distally along the respective elongated guides 1340a, 1340b to control the sheath 1332 and IUD strings, respectively. As can be seen in FIG. 13B, the insertion device 1300 is configurable to include a bilateral configuration, wherein the sliders 1342, 1346 are accessible from either the top 30 (upper) or bottom 40 (lower) face or surface of the handle 1335. Moreover, the telescoping slider configuration allows for left-handed or right-handed user operation without the need for a bilateral configuration with slider control features on both the top and bottom of the handle/housing.

As illustrated in FIGS. 13A-B, the sheath slider 1342 and string control slider 1346 each slide along the elongated guide along a longitudinal axis in a proximal or distal direction. At the distal end of the guide is a housing with a cavity 1345 into which at least a portion of the slide can be advanced. The sliders 1342, 1346 have a telescopic configuration, whereby at least one slider slides within or through at least one other slider along the longitudinal axis. As will be appreciated by persons of skill in the art, although the sheath slider 1342 slides through the string control slider 1346 in the configuration shown in FIGS. 13A-13B, the disclosure also includes designs where the string control slider 1342 slides within or through the sheath slider 1346.

In alternative configurations, a first slider can include a plunger slider rather than a sheath slider. The telescopic configuration of the sliders allows for a more streamlined, compact, and reduced-size insertion device. Additionally, this configuration can help avoid user confusion since the sliders move along the same path in the elongated guide. As with the previous example, an optional hollow area, indentation, cleft or cleavage 1348 can be provided in a proximal surface of the handle 1335 into which one or more strings can be held.

The insertion device 1400 of FIGS. 14A-14B, is similar to the insertion device 1300 of FIGS. 13A-13B, and has an elongated axis from a proximal end to a distal end, but the insertion device 1400 is further configurable to comprise a first cavity 1445a and a second cavity 1445b in the handle 1435, During step 3 of the insertion procedure, the sheath slider 1442 and string control slider 1446 are in the full proximal 10 position along the longitudinal axis of the elongated guide 1440, and at least partially surrounded by the proximal cavity 1445b. Each of the sheath control slider 1442 and the string control slider 1446 have a curved surface forming a recess into which a user's thumb fits as shown in FIG. 14B. Additional visual indication features 1460, 1460', 1460" are shown. Visual indication features can be provided on the elongated sheath 1432, the handle 1435, or both. The numbers 1, 2, and 3 on the insertion device components provide a visual indication to the user the appropriate positions of the insertion device components during the multiple phases of the insertion procedure. Visual indicators, such as numbers, can be applied in any suitable fashion including, but not limited to, printing, etching, molding, carving, and the like. Moreover, visual indicators can be positioned such that they are visible only during certain aspects of the procedure, and not visible during other aspects of the procedure.

Figure 15A:
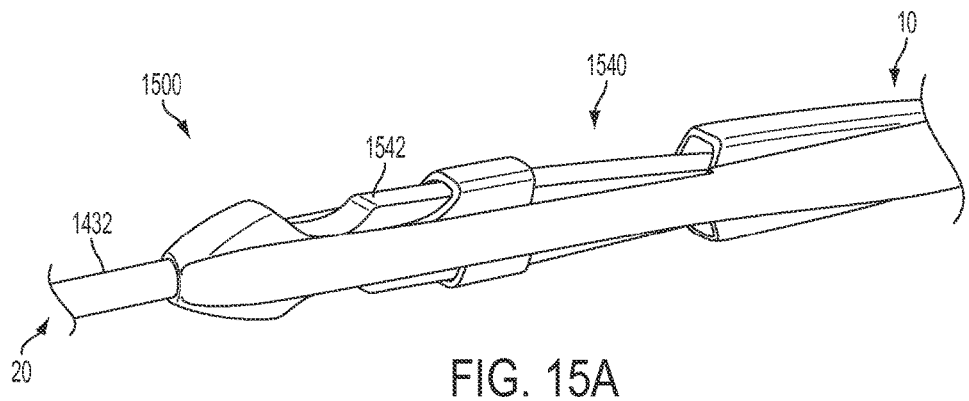
FIGS. 15A-15C illustrate an operational positioning of an insertion device comprising telescoping sliders during the first, second, and third phases of the IUD insertion procedure.
Figure 15B:
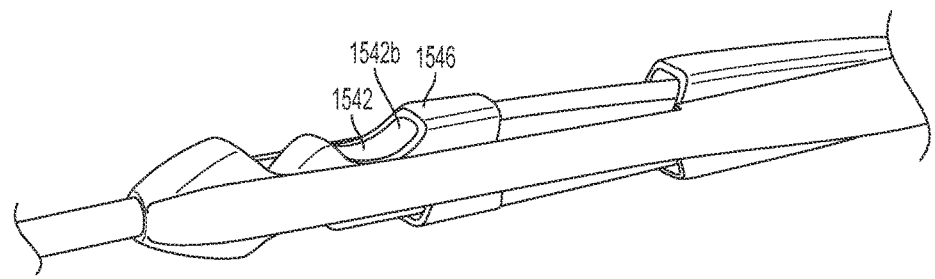
Figure 15C:
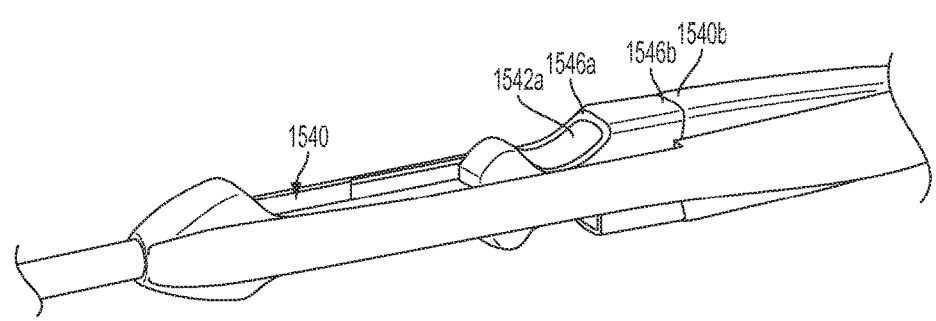

As with other configurations discussed above, alignment of certain control features or surfaces are configurable to correspond to a defined procedural step and corresponding IUD position, e.g., as shown in FIGS. 15A-15C. As shown in FIG. 15A, the insertion device 1500 is depicted as it would be configured during step 1 of the insertion procedure with the sheath slider 1542 is in a full distal 20 position along the longitudinal axis between the proximal end and the distal end of the elongated guide 1540. Each of the sheath slider 1542 and the string control slider 1546 have a curved surface forming a recess into which a user's thumb fits as shown in FIG. 15C. As shown in FIG. 15B, which depicts the insertion device 1500 as it would be configured during step 2 of the insertion procedure, the sheath slider 1542 and string control slider 1546 are each in a middle or intermediate position relative to a proximal end and distal end of the elongated guide 1540 along the longitudinal axis of the elongated guide, at a location between the distal and proximal ends of the elongated guide. As the user slides the sheath slider 1542 proximally along the elongated guide 1540 in transition from step 1 to step 2, the sheath slider 1542 approaches the string control slider 1546 and slides beneath or through a cavity in the string control slider 1546 in a telescopic manner.

As shown in FIG. 15B, a surface of the sheath slider 1542 aligns with a surface of the string control slider 1546 to form a smooth interface where a user's thumb meets both sliders simultaneously, or substantially simultaneously. As shown in FIG. 15B, in step 2, a first sheath slider surface 1542a and a first string control slider surface 1546a are aligned, signifying that the IUD is in an appropriate position corresponding to step 2. In step 3, as illustrated in FIG. 15C, corresponding to the insertion device 1500 configuration during step 3 of the insertion procedure, the alignment of the first sheath control slider surface 1542a and the first string control surface 1546a allows the user to simultaneously move both sliders in sync from step 2 to step 3. As shown in FIG. 15C, corresponding to the insertion device configuration during step 3 of the insertion procedure, the sheath slider 1542 and string control slider 1546 are in a proximal position along the longitudinal axis of the elongated guide 1540. When the sliders are retracted proximally, a second sheath control slider surface 1542b abuts a proximal elongated guide surface 1540b.

As discussed above, the insertion devices of the present disclosure can include one or more sliders including sheath slider where the sheath sliders have a recess in a proximal end into which a user's thumb is positionable, and a string control slider to control the string release feature and a sheath or plunger slider to control translational movement of the elongated sheath and the elongated inner member relative to one another along their longitudinal axes. As discussed above, the insertion devices can include one or more elongated guides in which the sliders glide along the longitudinal axis of the insertion device. In the above configurations a simple slider and elongated guide configuration has been discussed for the sake of simplicity and conciseness. In the above configurations, such as those shown in FIGS. 6, 8, and 10-15, the slider movement can cause simple, direct translational movement of the corresponding insertion device components—e.g., the sheath slider can be directly attached to the sheath, whereby when the sheath slider is moved backward a given distance, the sheath also moves backward the same distance. As will be understood by those of skill in the art, additional mechanisms of operation for the control features are envisioned by the insertion device of the present disclosure. The insertion devices of the present disclosure can include any number of a variety of different mechanisms of operation for transforming a user's input motion into translational or rotational movement of the insertion device components, such as those mechanisms available and known to those of skill in the art. For example, the insertion devices can include a crank system, a piston system, a rotary system, an oscillating lever system, a ratchet system, a rack and pinion system, a gear system, a hydraulic system, a spring system, a Geneva mechanism system, or the like, as well as combinations of any such systems.

Figures 16A, 16B, 16C:
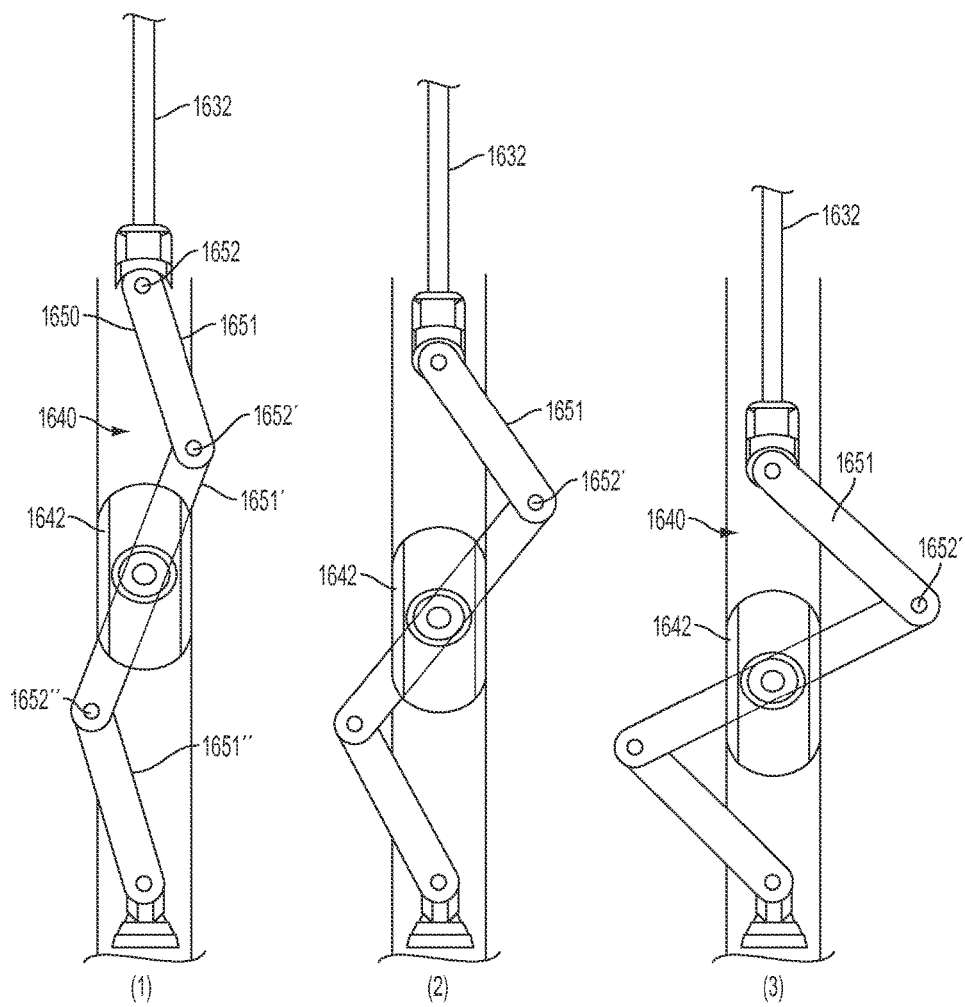
FIGS. 16A-16C illustrate an insertion device having a position control feature including a crank system.

In one general class of configurations, as shown in FIGS. 16A-16C, the insertion device includes a slider 1642 positioned within a elongated guide 1640 which controls a linkage system 1650. The configurations illustrated in FIGS. 16A-C are configurable to reduce an overall travel required by the user to achieve the various positions during use of the device. As will be appreciated by reviewing the figures, a travel multiplier can be achieved such that a given user movement is magnified and thus requires less actual movement by the user on the slider. Thus, the movement achieved in the handle is not 1:1 of the movement achieved at the distal end of the device. In configuration illustrated in FIGS. 16A-16C, the linkage system comprises one or more rods 1651, 1651', 1651" and pins 1652, 1652', 1652". The linkage system is attached to a translational member such as the sheath, plunger, or a string control feature. As illustrated in FIGS. 16A-16C, the slider 1642 moves along the elongated guide 1640, and the slider controls a linkage system 1650 which is attached to and moves the sheath 1632. As will be understood by those of skill in the art, the linkage system components are adjustable to correspond to target distances for movement of the sheath during, for example, phases 1, 2, and 3 of the IUD insertion procedure. In the aspect illustrated in FIGS. 16A-16C, the linkage system 1650 is fixed at the proximal end of the linkage system 1650, and the linkage system 1650 is attached to the sheath at the distal end of the linkage system 1650.

Figures 17A, 17B, 17C:
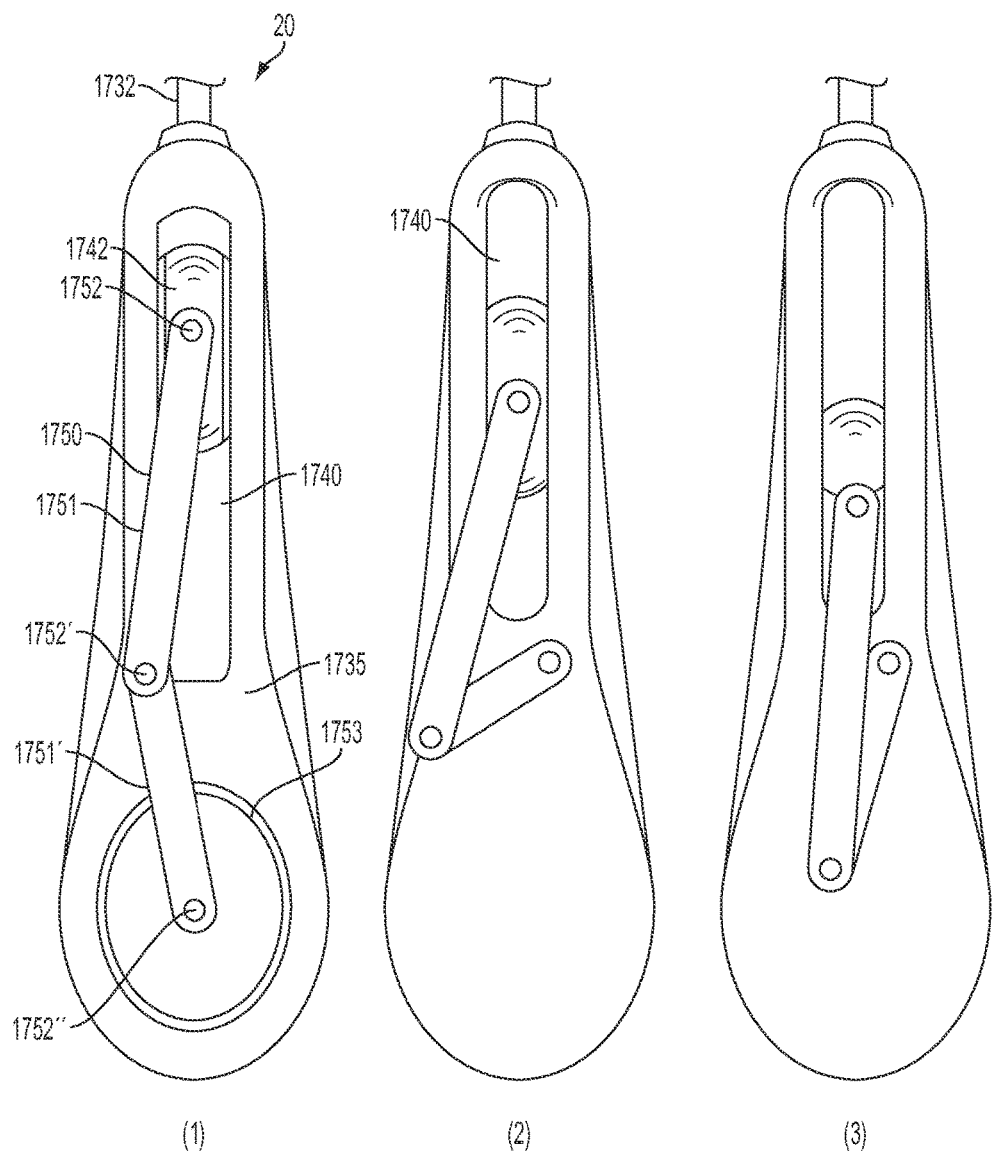
FIGS. 17A-17C illustrate an insertion device having a position control feature including a crank system.

A similar aspect is illustrated in FIGS. 17A-17C. The crank system 1750 features one or more rods 1751, 1751' and pins 1752, 1752', 1752". However, in this configuration, the crank system 1750 engages the slider 1742 at its distal end 20 and a gear 1753 at its proximal end 10. The crank system is positioned within the handle 1735 and at least a portion of the crank system 1750 operates within the elongated guide 1740. The crank system 1750 is further configurable to include a rotating dial member or gear 1753 attached to the proximal end of the crank system 1750 to limit or control the movement of the proximal end of the crank system 1750. As the gear 1753 is rotated about a central axis the longitudinal position of the sheath control slider 1742 which is in communication with the elongated sheath 1732, moves proximally as the gear moves in a counter-clockwise direction, as shown in FIGS. 17A-C. Pivot point shown 1752" is configurable such that it remains stationary during the movement depicted in FIG. 17. Where the pivot point 1752" remains stationary, the overall linear movement required of the user is reduced. This facilitates one-handed operation by a user during use.

Figure 18A:
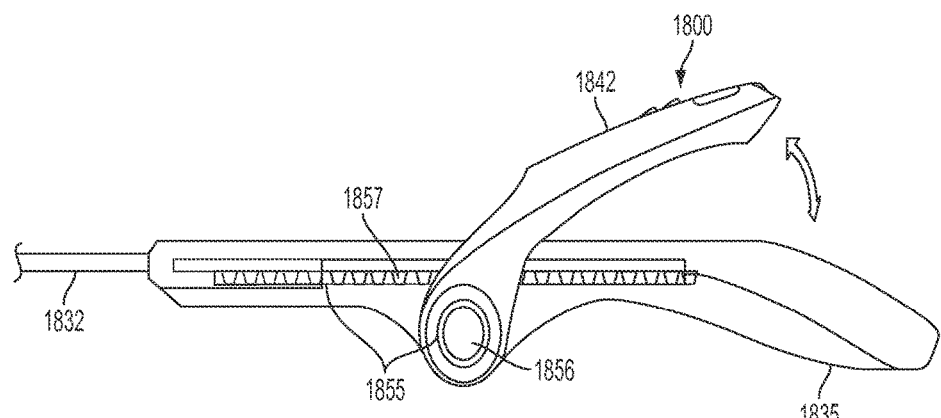
FIGS. 18A-18B illustrate an insertion device having a position control feature including a gear system.
Figure 18B:
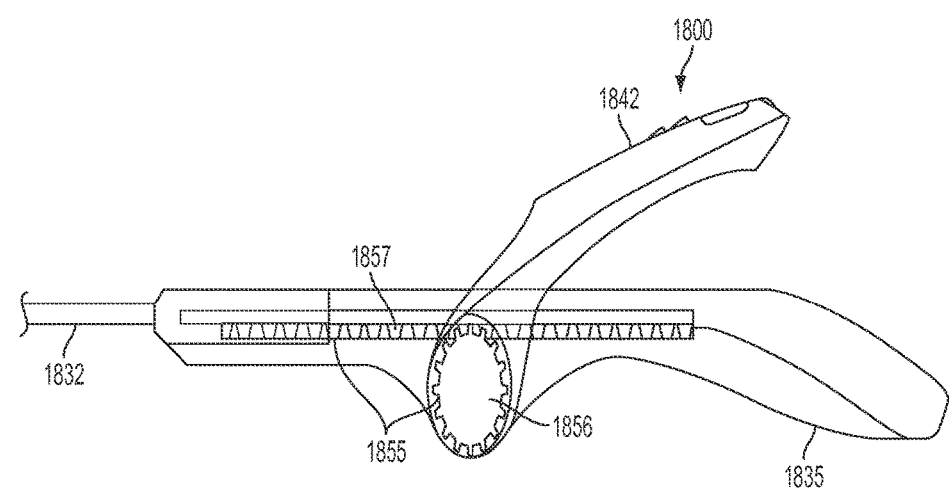

In another general class of configurations, as illustrated in FIGS. 18A-18B, the insertion device 1800 includes a handle 1835, a lever 1842 attached to a gear system 1855 including a first gear 1856, wherein the first gear 1856 moves a second gear 1857, wherein the second gear 1857 is attached to the sheath 1832. When the lever 1842 is actuated by the insertion device operator, e.g. by squeezing the lever, the first gear 1856 causes the second gear 1857 to move proximally, thereby moving the sheath 1832 proximally. The insertion device 1800 can further include a spring (not shown) attached to the lever 1842, wherein the spring (not shown) provides a counter-force to the user's input force applied to the lever 1842. The insertion device 1800 is further configurable to include a ratchet mechanism, whereby the spring returns the lever 1842 to its starting position without causing the sheath to move distally.

Figure 19A:
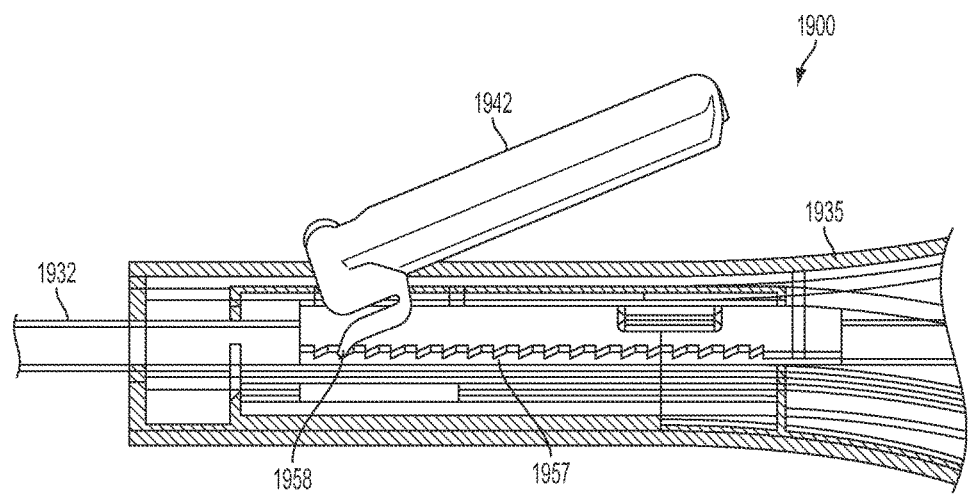
FIGS. 19A-19B illustrate an insertion device having a position control feature including a gear and ratchet system.
Figure 19B:
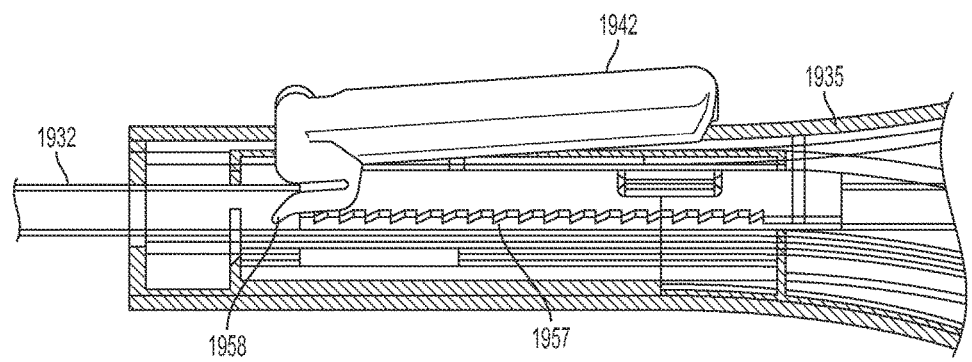
Figure 20A:
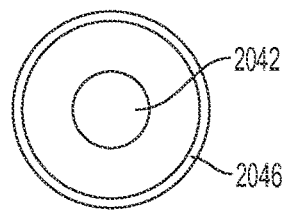
FIG. 20A illustrates a top view.
Figure 20B:
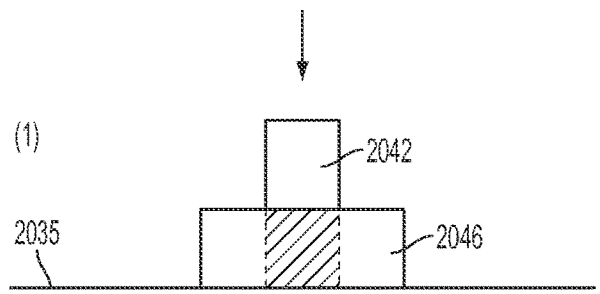
FIGS. 20B-20D illustrate cross-sectional side views, of actuatable, telescoping control buttons for controlling components of the insertion device.
Figure 20C:
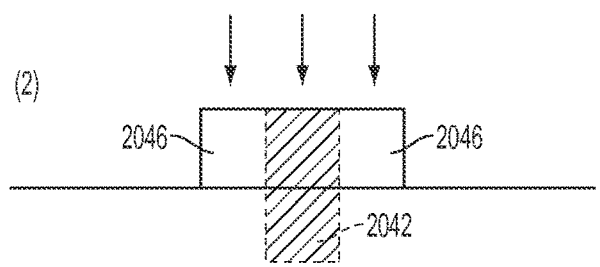
Figure 20D:
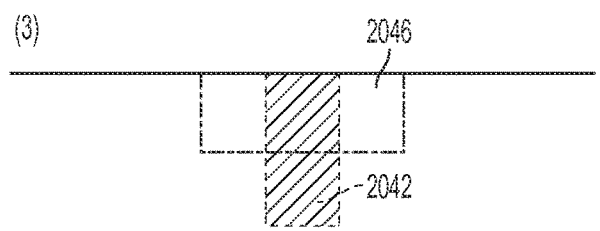
Figure 21A:
FIG. 21A illustrates a top view.
Figure 21B:
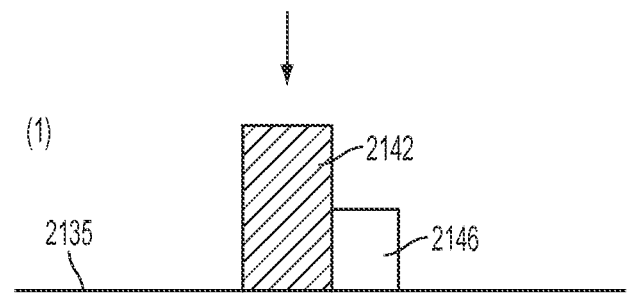
FIGS. 21B-21D illustrate cross-sectional side views, of actuatable, side-by-side control buttons for controlling components of the insertion device.
Figure 21C:
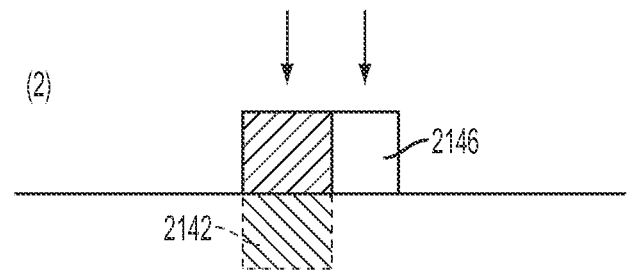
Figure 21D:
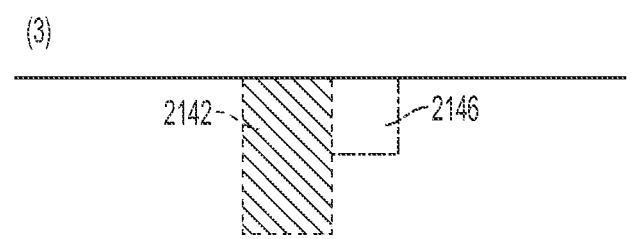

In another embodiment, as illustrated in FIGS. 19A-19B, the insertion device 1900 includes at least one gear or rack 1957 positioned within the handle 1935 housing attached to the lever 1942. When the lever 1942 is depressed by the operator, the gear 1957 moves a ratchet 1958 attached to the sheath 1932, whereby the gear 1957 moves the sheath proximally.

In other embodiments, as illustrated in FIGS. 20A-20D, 21A-21D, and 22A-22C, the insertion devices include position control features such as buttons 2042, 2046 which exhibit vertical movement rather than longitudinal movement along a elongated guide. In this manner, the insertion device operator can press downward on the one or more buttons to activate the position control features. For example, as illustrated in FIGS. 20A-20D, the insertion devices include a first button 2042 which is a sheath position control button, and a second button 2046 which is a string control button in the housing 2035. The string control button activates a string unlocking feature; exemplary string control features are discussed in further detail below. As illustrated in FIGS. 20A-20D, the first button is pressed downward in step 1 to retract the sheath. In step 2, a surface of the first button and a surface of the second button are aligned. In step 3, both the first and second buttons are pressed downward to further retract the sheath and activate the string control feature, such as a string unlocking feature. After step 3 is completed, the surfaces of the buttons can be aligned with the housing 2035 which provides a force-limiting feature preventing further downward movement of the buttons. In other embodiments, further movement of the buttons is prevented by a hard stop or a soft motion control feature, such as the features discussed in detail throughout the detailed description of this specification. As illustrated in FIGS. 20A-20D, the buttons can be telescoping with respect to one another, whereby a first button moves through or within the second button. The embodiment illustrated in FIGS. 21A-21D is similar to the embodiment illustrated in FIGS. 20A-20D, except that the sheath position control button 2142, and string control button 2146 are located side-by-side in the housing 2135 rather than in a telescoping configuration.

Figure 22A:
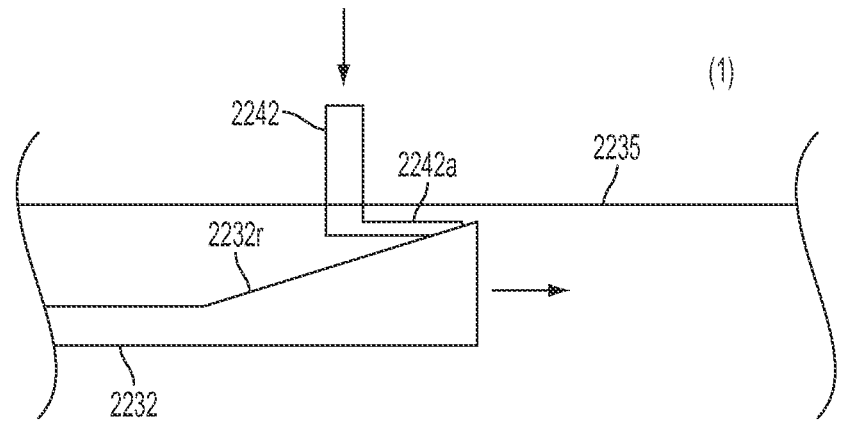
FIGS. 22A-22C illustrate cross-sectional side views illustrating a mechanism of action of a actuatable sheath position control button.
Figure 22B:
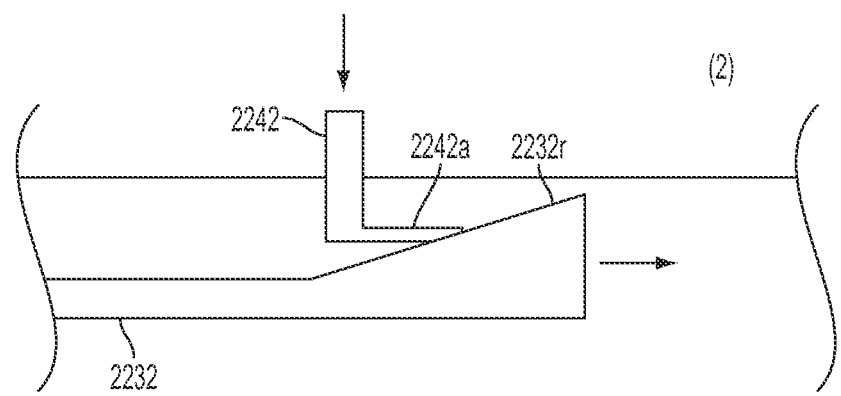
Figure 22C:
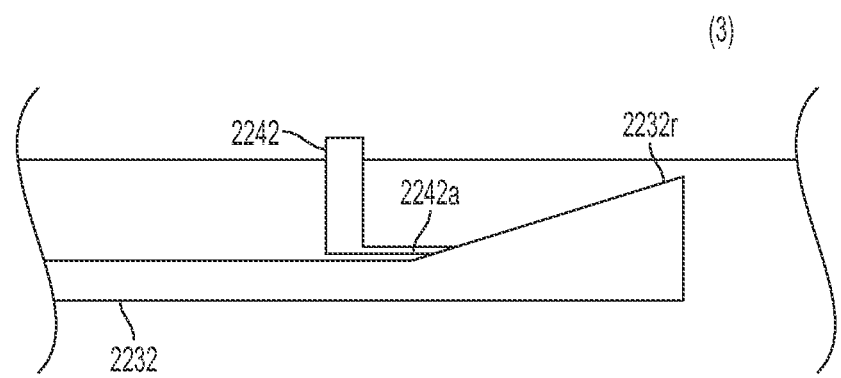

FIGS. 22A-22C illustrates a mechanism of action for the sheath position control buttons described in FIGS. 20A-20D and 21A-21D, according to an example embodiment of the present disclosure. As illustrated in FIGS. 22A-22C, the sheath control button 2242 positioned in the housing 2235 contacts a sheath feature 2232r during one or more phases of the insertion procedure. For example, the sheath feature can include a ramp or angled surface. When the button is pressed downward by the operator, the input force is translated from the button to a feature or surface 2242a of the button. The button feature or surface 2242a pushes against the sheath feature 2232r and moves the sheath in the backward direction. Additionally or alternatively, as will be understood by persons of skill in the art, the insertion device can be configured to push the plunger distally rather than push the sheath proximally. As can be seen FIGS. 22A-22C, the button feature 2242a moves along the ramp or angled surface 2232r, allowing simultaneous downward movement of the button 2242 and longitudinal movement of the sheath 2232. This mechanism of action is a non-limiting example of the embodiments envisioned by the present disclosure. Any suitable features and mechanisms are included in the present disclosure, as will be understood by persons of skill in the art. For example, the insertion device can include a gear system to allow simultaneous downward movement of the sheath position control feature and longitudinal movement of the sheath.

As described above, preserving a low profile dome shape at the distal end of the insertion device prevents or reduces trauma during the insertion process as well as premature escape of the IUD from the insertion device during the insertion process. In certain insertion device embodiments, in order to pass through the cervix without increased resistance, the insertion device must be positioned at the distal tip of the tube such that the arms and hands of the IUD are pressed together and form an atraumatic configuration at the tip of the insertion device. The insertion devices of the present disclosure are further adaptable to include one or more dimensional motion control features associated with the sheath and/or plunger to provide enhanced control of the distance between the plunger, sheath, and IUD, such that the IUD remains securely in the proper position during one or more steps of the insertion procedure. Alternatively or in addition to the position control features discussed above which are associated with the sliders, elongated guides, and housing, the sheath and/or plunger can include separate position control features directly attached to or associated with the sheath or plunger itself. These features can include dimensional motion control features to accurately control the distance between the tip of the plunger and the tip of the sheath. For example, as illustrated in the example embodiments of FIGS. 23A-23C, the insertion device can include a sheath 2332 and a plunger 2334, wherein one or both of the plunger 2334 and sheath 2332 each comprises one or more position control features associated therewith. For example, the plunger 2334 can include a first motion control feature 2338 having a first motion control surface 2338a and a second motion control surface 2338b on an opposing surface. The plunger 2334 can further include a second motion control feature 2339 having a first motion control surface 2339a. As depicted the first motion control surface 2338a of the first motion control feature 2338 is configured to face or oppose the first motion control surface 2339a of the second motion control feature 2339. The sheath 2332 is further adaptable and configurable to include one or more first motion control feature 2336 having a first motion control surface 2336a configured to face the first motion control feature 2338a of the first motion control feature 2338 of the plunger 2334 and a second opposing motion control surface 2336b configured to face the first motion control feature 2339a of the second motion control feature 2339 of the plunger 2334 The sheath 2332 is further adaptable to include additional motion control features such as one or more second motion control feature 2337a at a distal end and one or more third motion control features 2337b proximally positioned relative to the second motion control feature. As will be appreciated by those skilled in the art, the motion control features 2336, 2337 illustrated in the cross-section shown in FIGS. 23a-c can be distinct features placed at intervals on the interior surface of the sheath, or can form a continuous ring around an interior surface of the sheath.

Figures 23A, 23B, 23C:
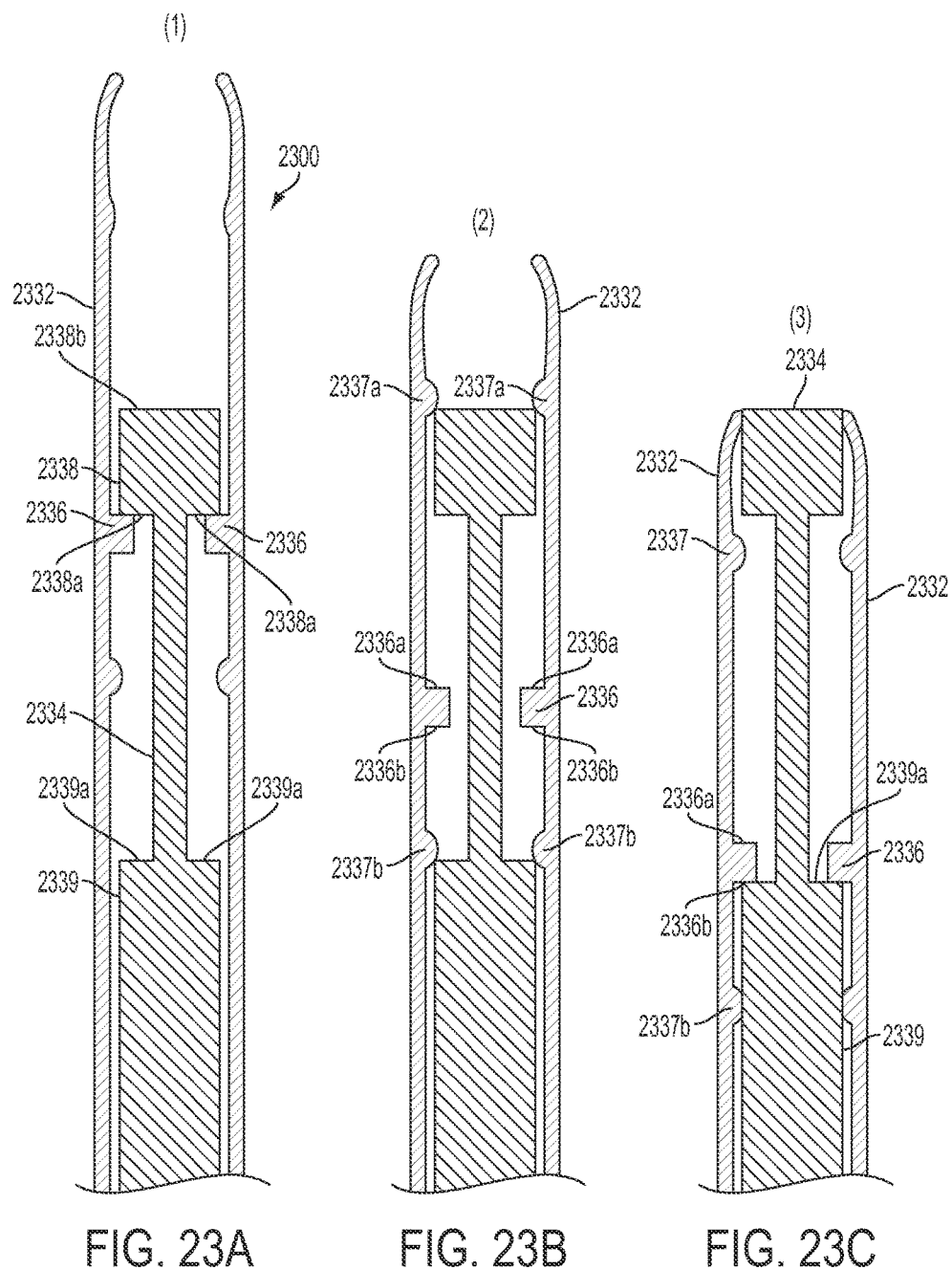
FIGS. 23A-23E illustrate various IUD position control features of the insertion device plunger and sheath.

As illustrated in FIGS. 23A-23C, the various position control features or motion control features, as well as the various motion control surfaces, are locatable at different positions along the longitudinal axis of the insertion device 2300. Much like the position control features discussed above, these features are adaptable to correspond to various phases of the IUD insertion procedure. These motion control features or motion control surfaces are configurable to control the position of the insertion device components during insertion, including the relative positions of the IUD, sheath, and plunger.

Figure 23D:
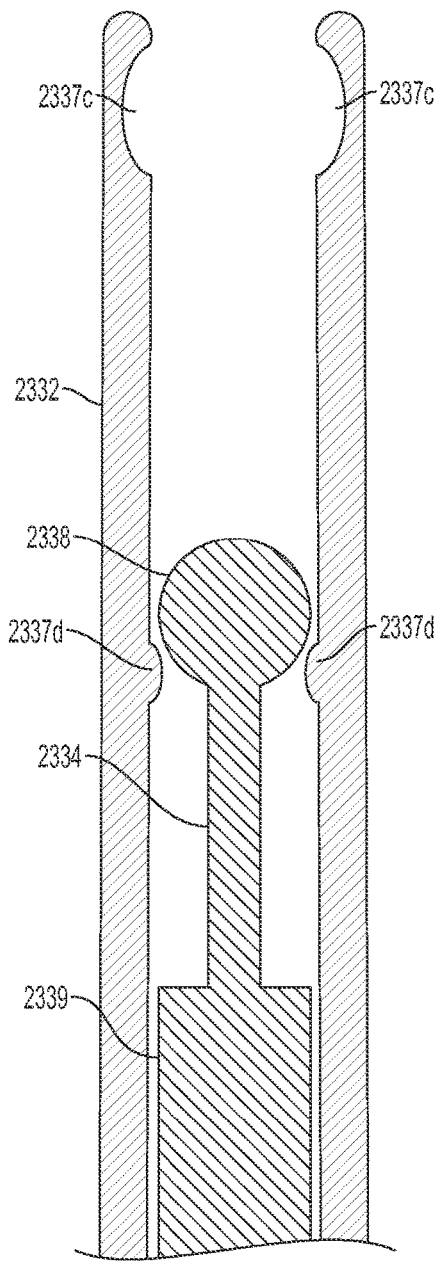
Figure 23E:
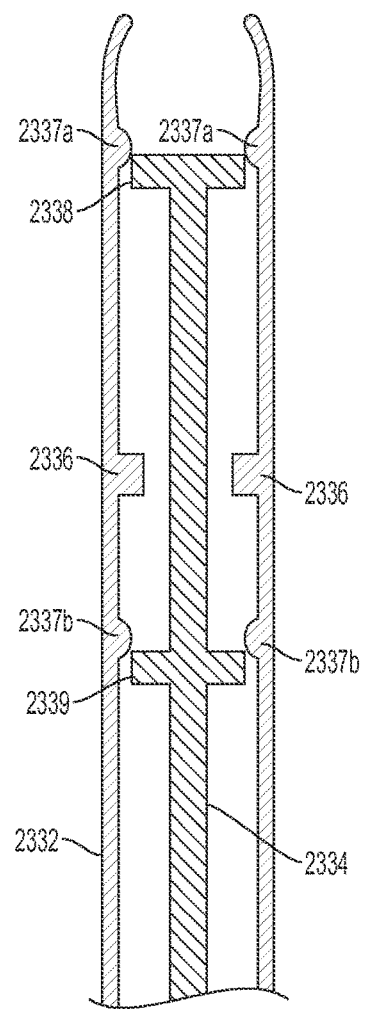

For example, in step 1 of an insertion procedure illustrated in FIG. 23A, a proximal surface of the distal plunger motion control feature 2338 contacts a distal surface of the first sheath motion control feature 2336 such that the first motion control surface 2338a of the distal plunger motion control feature 2338 contacts the first motion control surface 2336a of the sheath first motion control feature 2336, thereby preventing further movement of the plunger in the proximal direction and the sheath in the distal direction. In this manner, the motion control surfaces 2336a and 2338a are hard motion control surfaces with respect to one another. As will be appreciated by persons of skill in the art, these features or surfaces can also include soft motion control features or surfaces which merely impede rather than prohibit further movement. For example, as illustrated in FIG. 23D-E, the sheath 2332 includes one or more distally positioned soft motion control features 2337a, 2337b. In operation, for the device depicted in FIG. 23D, the sheath 2332 includes at least one motion control feature 2337c which is a cutout or detent that is conformable to a shape or profile of an IUD or a portion thereof. For example, the detent 2337c allows the IUD hands (not shown) to rest therein and properly align the IUD along the longitudinal axis of the sheath 2332. Additionally, the one or more detents 2337a can be positioned in limited locations which are located in-plane around an inner circumference of the sheath 2332 to properly align the IUD arms in-plane prior to deployment within the patient.

In step 2 of the insertion procedure illustrated in FIG. 23B, the sheath 2332 is retracted in the proximal direction (or the plunger is advanced distally) such that the sheath first motion control feature 2336 approaches the proximally positioned or second plunger motion control feature 2339. The insertion device 2300 is configurable to include one or more additional motion control features such as a second sheath motion control feature 2337a and a third sheath motion control feature 2337b. These motion control features can be soft motion control features which merely impede further movement of the sheath 2332 and plunger 2338 relative to one another and/or provide an indication, such as tactile feedback, to the insertion device operator that the insertion device 2300 has achieved an intermediate phase of the insertion procedure. The soft motion control features 2337a, 2337b can further be configurable to correspond to the IUD position in step 2, as illustrated in FIG. 4C and described above. These features provide a signal to the insertion device operator that the IUD arms are deployed from the sheath. As illustrated in FIG. 23B, the one or more sheath soft motion control features 2337a can be positioned distally along the sheath relative to the first sheath motion control feature 2336, and/or the one or more sheath soft motion control features 2337b. Moreover, the motion control features 2336b are locatable proximally along the sheath 2332 relative to the first sheath motion control feature 2336. These motion control features provide a low resistive force against the plunger 2338 after the insertion device 2300 is advanced past step 2 and into step 3. This can be achieved by minimizing the size or length of the first and second plunger motion control features 2336, 2339 along the longitudinal axis of the plunger 2334, as illustrated in FIGS. 23D and 23E. In this manner, only a short length or portion of the plunger 2334 will contact the resistive soft motion control features 2337a, 2337b, 2337d. For example, the plunger motion control features 2336, 2339 are configurable to have a length which is similar to the length of the sheath soft motion control features 2337a, 2337b, or can have a shape, such as a curved or rounded shape, which minimizes contact between the plunger motion control feature 2338 and the soft motion control feature 2337d.

In step 3 of the insertion procedure illustrated in FIG. 23C, the sheath 2332 is further retracted proximally (or the plunger is advanced distally), and the proximal plunger motion control feature 2339 contacts the first sheath motion control feature 2336 such that the first motion control surface 2339a of the proximal plunger motion control feature 2339 contacts the second motion control surface 2336b of the sheath first motion control feature 2336, thereby preventing further movement of the plunger in the proximal direction and the sheath in the distal direction. In this manner, the motion control surfaces 2336b and 2339a are hard motion control surfaces with respect to one another. As will be appreciated by persons of skill in the art, these features or surfaces can also include soft motion control features or surfaces which merely impede rather than prohibit further movement.

As will be understood by persons of skill in the art, the present disclosure includes variations of the example embodiment illustrated in FIGS. 23A-23C. For example, the sheath and/or plunger can include any suitable number of motion control features which can include any suitable number or arrangement of motion control surfaces. As discussed above regarding the position control features of the sliders, elongated guide, and housing, the plunger and/or sheath motion control features can include any suitable type of hard motion control features, soft motion control features, or any suitable combination thereof. For example, the motion control features or surfaces can include physical features such as detents, notches, grooves, protrusions, tabs, ridges, flanges, flaps, gates, flexible members, contours, curves, shapes, etc. Additionally, while the motion control features or surfaces are preferably located closest to the distal or front end of the insertion device, such features or surfaces can suitably be located at any suitable position along the longitudinal axes of the sheath and plunger.

With these plunger and sheath motion control features, loading the plunger and IUD into the sheath prior to insertion is achievable by pre-loading the components during insertion device manufacture. Additionally, the motion control features are arrangeable such that the motion control features are aligned in a first position and then misaligned in a second position which is achievable upon rotating one or more of the plunger and sheath relative to one another, thereby allowing the IUD and plunger to be loaded into the sheath by first rotating the components, then sliding the plunger motion control features past the sheath motion control features, and finally rotating the components again to realign the plunger and sheath motion control features so that they are aligned during the insertion procedure. In another embodiment, the IUD can be loaded into an opening in the housing/handle or the side wall of the sheath, as discussed in further detail below.

In still another embodiment, the insertion devices are adaptable to include a plunger having a feature for locking the IUD into place to prevent the IUD from moving relative to the plunger along the longitudinal axis of the insertion device during one or more phases of the insertion procedure. For example, the plunger can include a feature which grasps or pinches the IUD during at least the first insertion phase, and optionally the second and third phases. For example, the plunger can grasp or pinch the IUD at the proximal end of the IUD near the strings, or grasp or pinch the IUD strings. The insertion device can further include an IUD unlocking feature. For example, the sheath can include a feature which unlocks the IUD from the plunger as the sheath is moved during step 2 or step 3, or after step 3.

The insertion devices of the present disclosure are further adaptable to include features which provide an atraumatic distal or front end or tip of the insertion device to minimize pain induced by the insertion device as it passes through the patient's cervix and into the uterus, as well as during withdrawal of the insertion device from the patient after the IUD is inserted. The insertion devices of the present disclosure are also adaptable to include features which minimize the cross-sectional dimensions of the distal end of the insertion device during insertion and reduce or eliminate the blunt or abrupt features at the distal end of the insertion device which may cause pain or discomfort to the patient as the insertion device passes through the cervix during use.

Figure 24A:
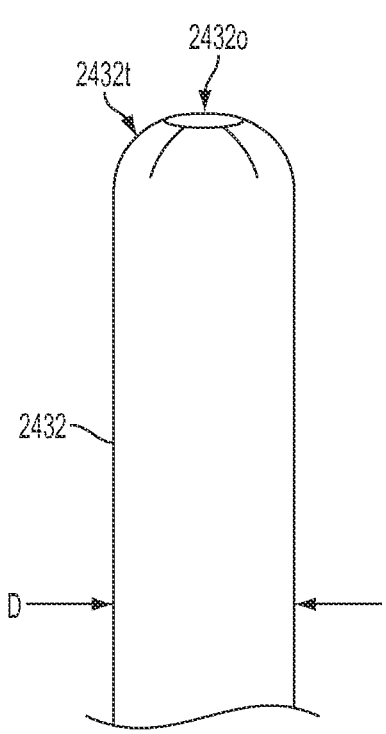
FIGS. 24A-24G illustrate various aspects of the elongated sheath of the insertion device and atraumatic sheath tip.
Figure 24B:
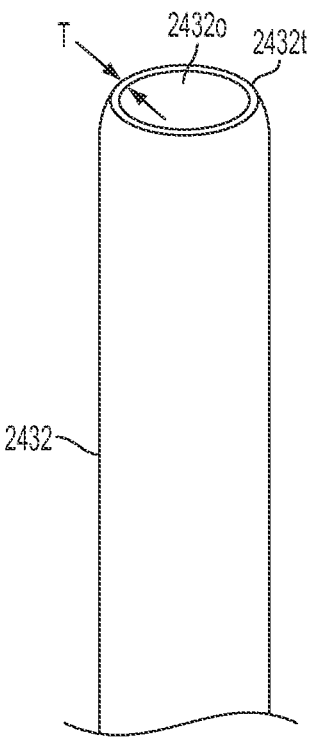
Figure 24C:
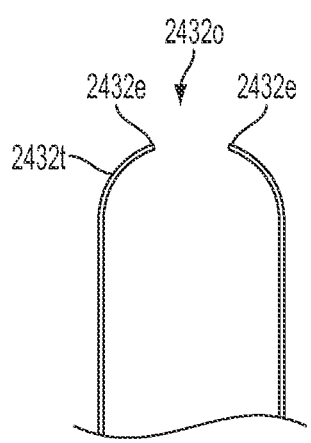

The insertion devices are also configurable to include a sheath 2432 having a tapered or rounded distal end or tip 2432t, wherein the cross-section, or outer diameter, D, of the insertion device sheath decreases from a proximal value towards the distal end or tip of the insertion device, as illustrated in FIGS. 24A-24G. The sheath tip 2432t is tapered or taperable toward the distal end of the sheath 2432, as illustrated in FIGS. 24A-24B. As illustrated in FIG. 24B, the thickness T of the sheath 2432 wall can also be minimized at the distal-most end of the sheath 2432 to reduce the impact of the sheath wall thickness on the patient. The thickness of the sheath wall can be reduced at the distal end of the sheath relative to the thickness measured at a different location along the longitudinal axis of the sheath 2432. Maintaining a thicker sheath wall away from the distal-most end of the sheath will allow for the appropriate rigidity of the sheath, while a reduced sheath wall thickness near the sheath tip 2432t will minimize any abrupt features which may scratch or pinch the patient during insertion. As illustrated in FIG. 24C, the ends 2432e of the sheath wall can further be rounded to minimize abrupt or sharp features of the insertion device. The insertion device sheath 2432 can also include an opening 2432o, as illustrated in FIGS. 24A-24C.

Figure 24D:
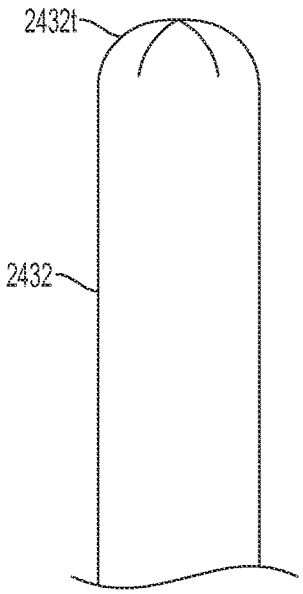
Figure 24E:
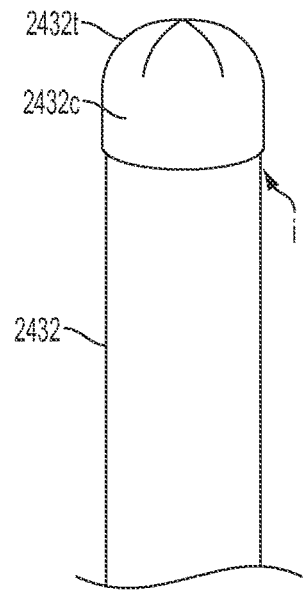
Figure 24F:
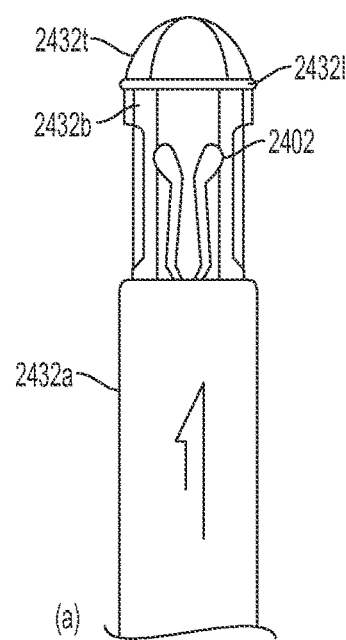
Figure 24G:
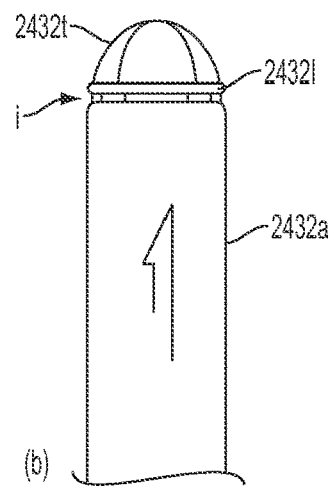

In another general class of embodiments, as illustrated in FIGS. 24D-24F, the sheath tip 2432t is formed such that the IUD is substantially or completely covered by the sheath 2432 during an initial phase of the insertion procedure, e.g., when the insertion device is inserted through the cervix. At this initial phase of the procedure the devices are configurable such that the sheath lacks or nearly completely lacks an opening at the sheath tip 2432t. The tip can be formed as part of the sheath, as illustrated in FIG. 24D. Alternatively, as illustrated in FIG. 24E, the sheath tip can include a separate component such as a sheath cap or cover 2432c which fits or slides over the sheath 2432 to cover the end of the sheath during insertion. Preferably, the sheath cover has a thickness which is thinner than the sheath wall, but is made from a material which is strong enough to contain the IUD during insertion. The sheath cover can be made from a material which is the same as the sheath material, or the sheath and cover can comprise different materials. The cover is configurable to be attached to the sheath via mechanical force or chemical adhesion, including suitable methods of attachment known in the art. As will be appreciated by those skilled in the art, if the diameter of the tapered tip is smaller than the diameter of the opening of the external orifice of the cervix, and then gradually increases in diameter along its length to accommodate the IUD, the tip can be advanced through the external orifice and as the diameter of the device increases the device will apply lateral pressure on the walls of the cervix causing the opening to the cervix to slowly increase in diameter to accommodate the remainder of the device.

In another example embodiment, as illustrated in FIG. 24F, the insertion device includes an outer sleeve or sheath 2432a and at least one inner sheath 2432b. The IUD 2402 is housed by the inner sheath 2432b, and the inner sheath slides into the outer sheath 2432a in a telescopic manner so that the inner sheath and IUD can be loaded into the outer sheath to prepare the insertion device for the IUD insertion procedure. The example embodiment illustrated in FIG. 24F depicts an inner sheath 2432b comprising the tapered or rounded sheath tip 2432t. However, as will be understood by persons of skill in the art, the inner sheath and/or the outer sheath is configurable to comprise the sheath tip 2432t. Preferably, the interface i between the sheath and cap of FIG. 24E, or between the inner and outer sheaths of FIG. 24F, is a seamless interface which will not pinch, scratch, bind or otherwise harm the patient during the insertion procedure. For example, a seamless interface is achievable by matching the outer diameter of both components at the interface, i, e.g., matching the outer diameters of the sheath 2432 and sheath cap 2432c at the interface i shown in FIG. 24E, or matching the outer diameters of the outer sheath 2432a and the inner sheath 2432b at the interface i shown in FIGS. 24F-G. In the embodiment illustrated in FIG. 24F, the inner sheath 2432b can include a lip 2432l which allows for the outer diameter of the inner sheath 2432b to match the outer diameter of the outer sheath 2432a, while at the same time allows the inner sheath to slide within the outer sheath along the portion of the inner sheath which is below the lip 2432l. In another example embodiment (not shown), the interface can be located at a distance along the longitudinal axis of the insertion device which is far enough from the distal end of the sheath such that the interface will not enter the patient's cervix during the insertion procedure.

Since the sheath and plunger motion control features are small due to their position inside the sheath or affixed to the plunger, the insertion devices are configurable to include one or more force-limiting features, such as those discussed above, to prevent the user from applying excessive force to the slider which could subsequently break or damage the sheath and plunger motion control features.

IV. Thread Locking and Unlocking Features

As described above, the insertion devices of the present disclosure include one or more string control features or mechanisms. The string control feature can include one or more string locking features and at least one string unlocking feature or mechanism. The one or more string control features or mechanisms can include manual features, automatic features, or a combination thereof.

In one general class of configurations, as illustrated in FIGS. 25A-25B and 26A-26E, the insertion devices are adaptable to include a dimensional feature such as an opening, detent, notch, wedge, or cleft 2548, whereby the one or more IUD strings (not shown) are firmly engageable within the dimensional feature. The dimensional string locking feature is formable in the insertion device housing 2535 or as part of another suitable insertion device component. In one example embodiment, the insertion device operator can pull the IUD strings into the dimensional string locking feature 2548 upon loading the IUD into the insertion device. In additional embodiments, the strings can be automatically placed or locked in the string locking feature, as discussed below in additional embodiments. The one or more string locking features can function to control the IUD position during insertion and/or move the strings out of the way to prevent the strings from interfering with the insertion procedure. Additional advantages will be appreciated by persons of skill in the art. The strings can be manually, automatically or semi-automatically removed from the locking feature 2548 upon completion of IUD insertion.

In addition to the at least one string locking feature, the insertion device includes one or more string unlocking features to remove the strings from a locked position. The one or more unlocking features can include manual and/or automatic string unlocking features. As illustrated in the example embodiment of FIGS. 26A-26E, the insertion device can include a movable string control feature 2649 which pushes or releases the strings out of the string locking feature 2648. As illustrated in FIGS. 26A-26E, the insertion device includes a movable string release feature which can move past or through the string locking feature 2648. As discussed above and illustrated in FIGS. 26A-26E, the string locking feature can include an opening or dimensional feature in the insertion device housing 2635. When the string unlocking feature 2649 is in a first position, the strings remain locked in the string locking feature 2648. When the string unlocking feature 2649 is moved, the strings are released or unlocked by the string unlocking feature 2649.

Figures 26B, 26C:
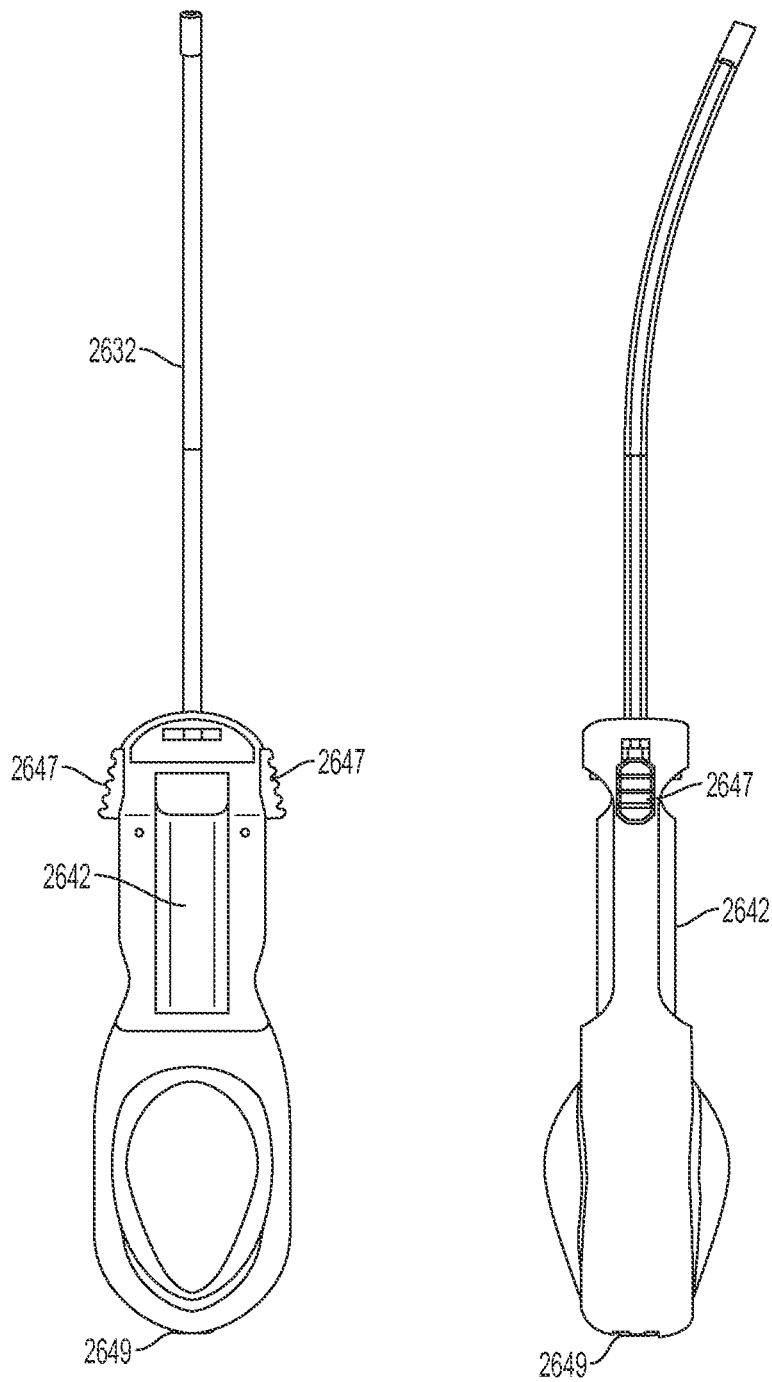

As in the example embodiment illustrated in FIGS. 26A-26C, the insertion device can include a feature 2649 which is both a string locking and string unlocking feature. For example, the string control feature 2649 is configurable to lock the IUD strings into place by pinching the strings against housing 2635 in a first position (not shown). For example, the strings can be pinched or locked in the string locking feature 2648 by the string control feature 2649. When the string control feature is moved (e.g., pushed proximally), as illustrated in FIG. 26A, the strings are released from the string locking feature 2648 since the string locking and unlocking control feature 2649 is no longer pinching or locking the strings against the housing 2635, string locking feature 2648, or another insertion device component. As illustrated in FIG. 26A, the housing or string locking feature 2648 and/or the string unlocking feature 2649 can include an angled or tilted surface, whereby a surface of the string unlocking feature 2649 contacts a surface of the string locking feature 2648 when the strings are locked, and the surfaces are not in contact when the strings are unlocked.

In the example embodiments illustrated in FIGS. 26D-26E, the string locking feature 2648 locks or controls the strings in a dimensional feature in the insertion device housing 2635, and the string unlocking feature 2649 releases, eases or unlocks the strings when it is moved from a first position (as illustrated in FIG. 26D) to a second position (as illustrated in FIG. 26E). For example, the strings are positionable such that they extend beyond, or protrude through, a proximal end of the insertion device through an opening in the string unlocking feature 2649. For example, the feature 2649 can include a hollow tube portion through which the strings are threaded. In this embodiment, the strings are pulled firmly from the opening in the feature 2649 and into the string locking feature 2648. When the string unlocking feature 2649 is moved proximally, the unlocking feature 2649 pushes against the strings to remove them from the locking feature 2648. As will be understood by persons of skill in the art, these non-limiting example embodiments are illustrated to illustrate the string control features envisioned by the present disclosure, and additional embodiments and mechanisms of operation are included, such as additional embodiments discussed throughout this specification.

The string control feature 2649, which can be a string locking and/or string unlocking feature, is further configurable to be controllable by a string control feature such as a slider 2646, as illustrated in FIGS. 26D-26E. As illustrated in FIG. 26D, the string control feature 2646 includes a slider position return feature 2646r which allows the user to move the slider 2646 back to its starting position. The slider position return feature can include a spring, detent, tab, or any other suitable feature, as will be understood by persons of skill in the art. The string control 2646 feature is adaptable to include a telescoping string control slider, e.g., as in the embodiment illustrated in FIGS. 13-15, as discussed in further detail above. Alternatively, or additionally, the string control feature 2649 is controllable by one or more string release buttons 2647, as illustrated in FIGS. 26B (top view) and 26C (side view). The buttons 2647 can be located in or on the housing in a separate location from the sheath control slider 2642, as illustrated in FIGS. 26B-26C. The at least one button 2647 can include a slider, a depressible button, or any other suitable control feature or mechanism for moving the string unlocking feature 2649. The string control feature 2649 can be adapted and configured to include an elongated member which is physically attached to or operatively connected to the one or more string control features such as the string release slider 2646 or the string release button 2647.

Figure 27A:
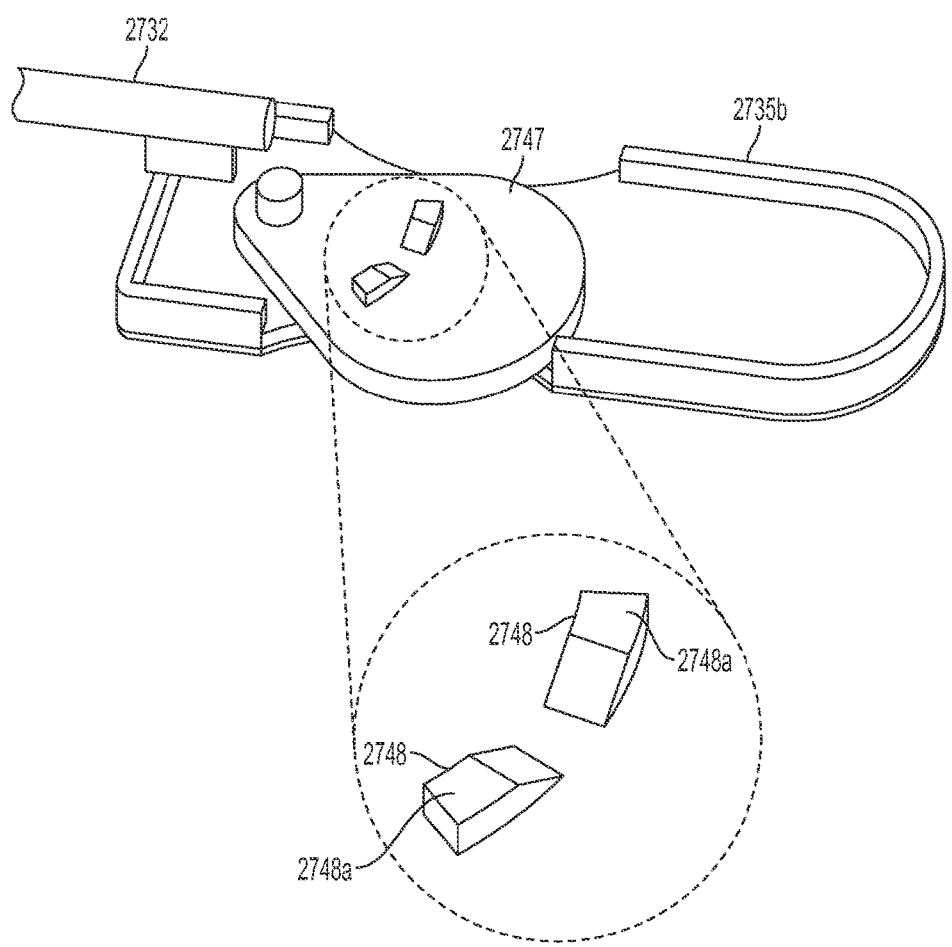
FIGS. 27A-27C illustrate various string control features, including string locking and string unlocking features.
Figure 27B:
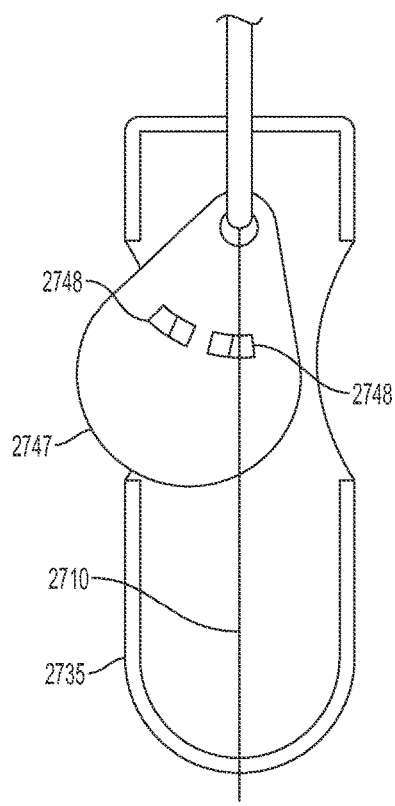
Figure 27C:
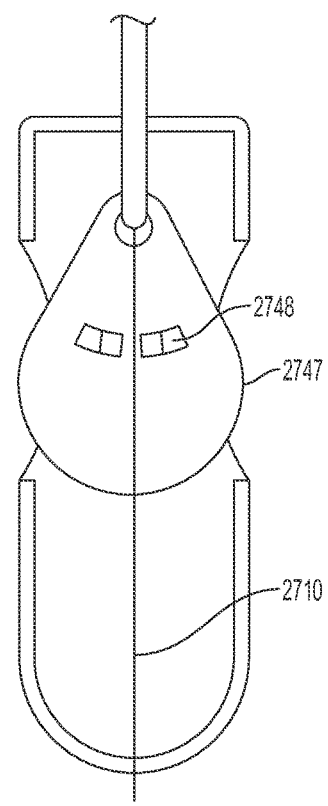

FIGS. 27A-27C show additional details of the insertion device 800 illustrated in FIGS. 8A-8F and described in further detail above. In one configuration, as illustrated in FIGS. 27A-27C, the insertion device includes a string control feature 2747 comprising one or more dimensional string locking features 2748. The string locking features 2748 are configurable such that each feature include a surface 2748a adapted and configured to pinch or lock the one or more IUD strings 2710 which extend from within the elongated sheath 2732 against another component or surface of the insertion device. The string locking features 2748 or surfaces 2748a are formable from ramps, curved surfaces, tilted surfaces, rounded features, depressions, protrusions, or other suitable dimensional features on an interior surface of the lower surface of the housing 2735b. The string control feature 2747 provides both a string locking and string unlocking mechanism. When the string control feature is moved from a first position to a second position, the IUD string is locked or restrained in a first position or unlocked or unrestrained. When the string control feature 2747 is in a first position, as illustrated in FIG. 27C, the at least one IUD string 2710 is lockable or restrainable into place by the string locking feature 2748, whereby the surface 2748a of the feature 2748 pinches, presses or restrains the string against another component or surface of the insertion device (not shown), such as an interior surface of the handle 2735. When the string control feature 2747 is moved to a second position, as illustrated in FIG. 27C, the string is released from the locked position. The string locking features 2748 include a curved or tilted surface to allow for gradual locking or restraining of the insertion device as the curved or tilted surface moves across the string. The string control feature 2747 is moveable through a range of motion from the locked to unlocked position by sliding, swiveling, or otherwise moving the feature 2747.

Figure 28:
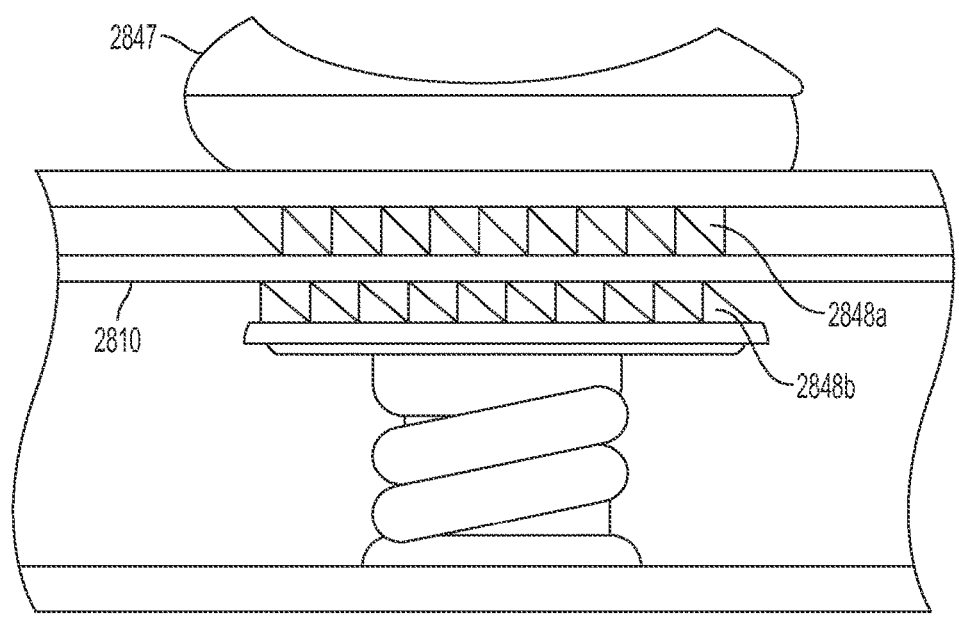
FIG. 28 illustrates an example aspect of an insertion device including string control features.

In still another embodiment, the insertion device includes a string locking feature comprising one or more grooves or teeth which grab and lock the string into place, pinching the string against the grooves or teeth and another surface of the insertion device. For example, as illustrated in FIG. 28, the string locking feature 2847 comprises a first component with at least one surface having teeth 2848a. The string locking feature 2847 may further comprise a second component with at least one surface having teeth 2848b wherein the teeth of the first component face the teeth of the second component. Moving the string locking feature 2847 toward the second component surface 2848b causes the two surfaces having teeth to engage or pinch a string 2810 positioned between the surfaces, thereby locking the string into place. In one embodiment, the string is locked or restrained by depressing the string control feature 2847 and released or unlocked by releasing the string control feature 2847. In other embodiments, the string is lockable by another feature such as a latch or hinge which secures the surfaces 2848a, 2848b together. In still other embodiments, the string control feature 2847 is moved by sliding or rotating the string control feature 2847, whereby the string is pinched between a first surface of the string control feature 2847 and a second surface, wherein the first and/or second surface comprises teeth or grooves. As will be appreciated by those skilled in the art, the string control mechanisms are adaptable to secure a string in a first position, and then release the string, or to control the tension of the string relative to the IUD during deployment by restraining the string or strings until the string is released. Thus, all string locking and unlocking features and mechanisms are adaptable to lock, restrain, tension, or release (either partially or fully) the strings that engage the mechanisms.

In still other embodiments, the string locking and unlocking feature or mechanism is adaptable to include a hinge or clamp feature, whereby the strings are locked when the hinge or clamp is closed or tightened, and the strings are unlocked when the hinge or clamp is opened or loosened.

In yet another embodiment, the insertion devices are configurable to include one or more mechanisms which prevent the user from deploying the IUD while the strings remain in a locked or restrained position. Such a feature can facilitate the prevention of pain associated with the insertion procedure when the device operator pulls on the deployed IUD strings, e.g. when the insertion device attempts to retract the insertion device post-insertion while the strings remain locked. By requiring that the strings are unlocked before the insertion device will allow full deployment of the IUD, the preventative feature provides a feedback mechanism, signal or reminder to the operator that the strings need to be unlocked before proceeding with the procedure.

Figure 29A:
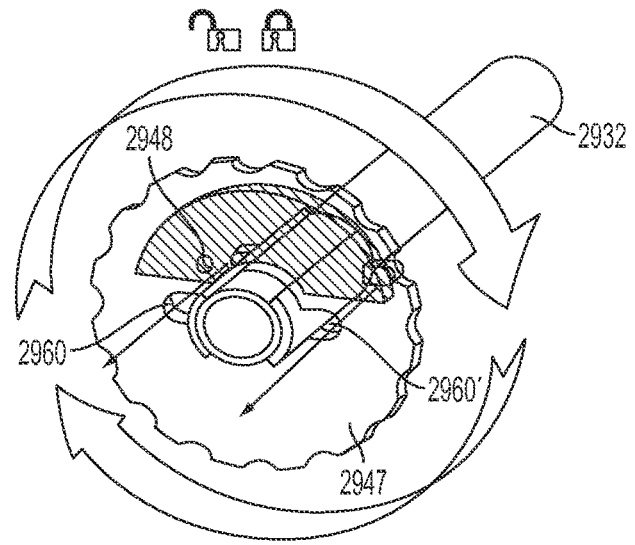
FIGS. 29A-29D illustrate various string control features, including string locking and string unlocking features, as well as sheath alignment features.
Figure 29B:
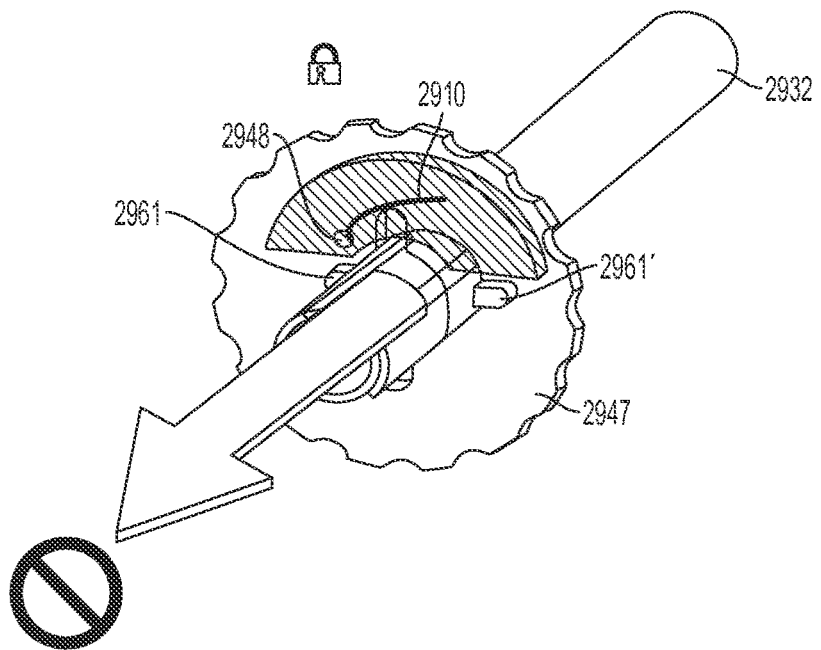
Figure 29C:
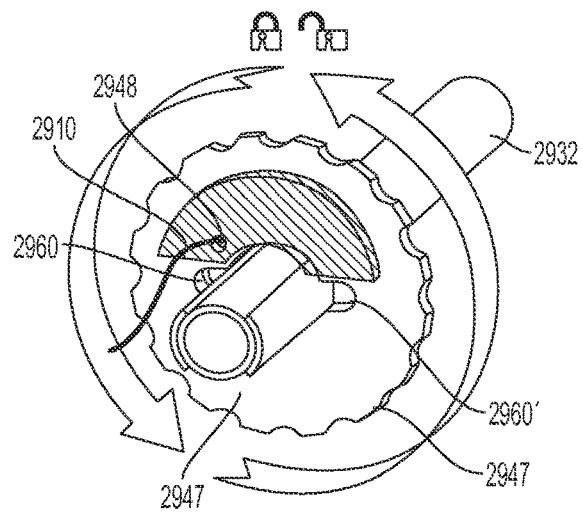
Figure 29D:
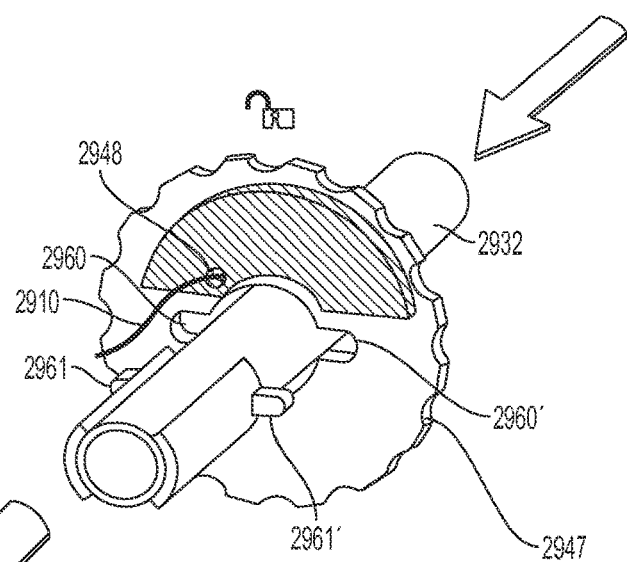

In one example embodiment, as illustrated in FIGS. 29A-29D, the insertion devices disclosed herein are configurable to include a string locking and unlocking feature 2947, which includes one or more alignment features 2960. As illustrated in FIGS. 29A-29D, the IUD strings are locked and unlocked by the string control feature 2947. The string 2910 passes through an aperture 2948. For example, sliding or rotating the string control feature 2947 can lock and unlock the strings depending on the direction the feature is moved or rotated. When the strings are locked or pinched by the string locking feature 2947, as illustrated in FIG. 29B, the string control feature 2947 exhibits an interface which prevents the sheath from proceeding beyond the string control feature interface. For example, the sheath can include one or more dimensional features 2961, such as tabs or protrusions, which align with one or more features 2960 of the string control feature 2947, such as the openings 2960, 2960' illustrated in FIGS. 29A-29D. When the strings are locked, sheath features 2961, 2961' are not aligned with the openings 2960, 2960' in the string locking feature 2947, and the sheath 2932 cannot be retracted, as illustrated in FIG. 29B. When the strings are unlocked, the sheath features 2961. 2961' are aligned with the openings 2960, 2960' in the string locking feature 2947, and the sheath can be retracted, as illustrated in FIGS. 29C-29D.

In yet another embodiment, the insertion device includes a string cutting feature. The string cutting feature can be a string unlocking feature, whereby the strings are cut by a cutting feature of the insertion device and thereby released from a locked position. Alternatively, the string cutting feature can be separate from the string unlocking feature. As will be understood by persons of skill in the art, the string cutting feature can include a blade or any known mechanism suitable for cutting or breaking the IUD strings.

Either manual, automatic or semi-automatic string locking or unlocking features are contemplated in the insertion devices of the present disclosure. Incorporating any of the features mentioned above, the insertion devices are configurable to include an automatic string locking feature, whereby the strings are automatically locked and unlocked by the insertion device without requiring additional procedural steps or user input. Automatic locking and unlocking features can include any suitable features or mechanisms known in the art, as well as the features of the present disclosure discussed herein. For a manual process, a user pulls on the strings when the device is in a correct or desired position or configuration, e.g. when a dome shape is achieved, and then positions the one or more strings into the cleft such that the cleft walls pinch the strings, thereby locking the strings into place.

V. Feedback Features

As described above, the insertion devices of the present disclosure are adaptable and configurable to include one or more indicator or signal features which provide a sensory signal to the user that the IUD and other insertion device components are in an appropriate or targeted position corresponding to one or more phases of the IUD insertion procedure. The sensory indicator features or user feedback of the present disclosure includes, but is not limited to, a visual indicator such as a visual alignment feature described above, an auditory indicator such as a click or other noise heard by the insertion device operator, and/or a tactile indicator feature which can be felt by the operator, such as a tactile indicator felt by the operator's finger or thumb (e.g., when the one component of the device engages another component, such as occurs with configurations featuring soft motion control features).

The insertion devices are further configurable to include one or more signal features to alert the operator at various stages of the insertion procedure or to provide assurance that the IUD is properly positioned, thereby signaling the operator to perform the next step in the procedure. Likewise, such guidance can inform the clinician of instances where the IUD is improperly positioned, either by the lack of the aforementioned positive signal showing proper IUD positioning, or by including an additional negative signal feature. The insertion devices include non-visible indicator features such as tactile or auditory indicator features. In this manner, the insertion device provides indicators without requiring the user to look away from patient and back toward the insertion device, whereby the user can focus on the patient at the point of insertion.

Figure 30A:
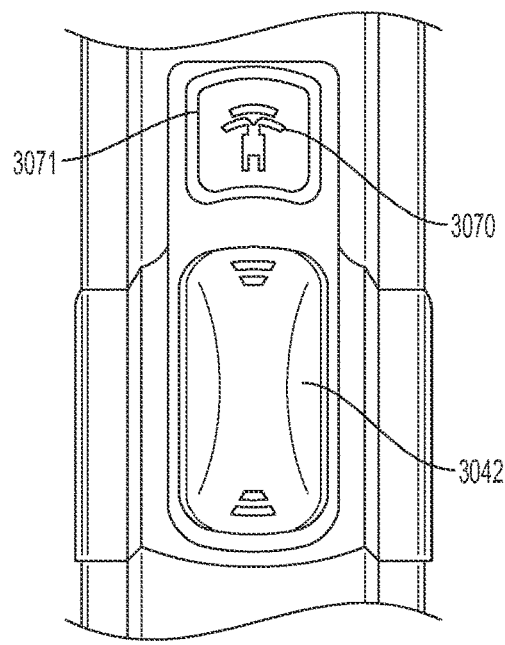
FIGS. 30A-30B illustrate indication features of the insertion device.
Figure 30B:
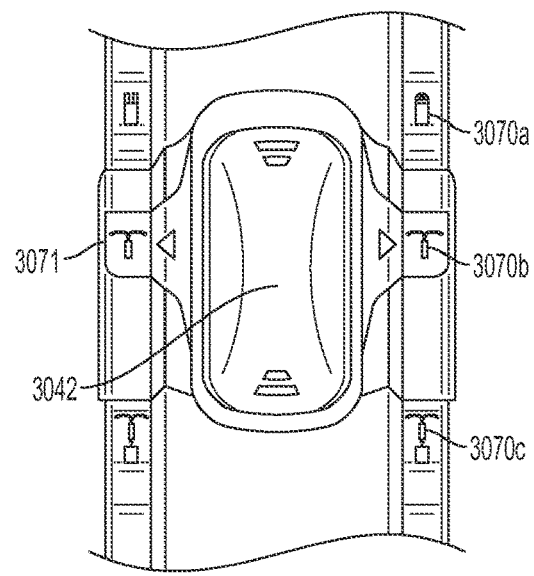

In additional aspects of the disclosure, the insertion devices are adaptable to display a visual indicator symbol such as a picture, word, number, pattern, color change, or the like, whenever the IUD location corresponds to a procedural step (or, conversely, whenever the IUD location does not correspond to a procedural step). As illustrated in FIGS. 30A-30B, indication features of the insertion device can include symbols 3070 which depict the IUD positioning corresponding to the procedural step and insertion device positioning. For example, the slider 3042 can include a viewer window 3071 which displays a symbol depicting the corresponding IUD positioning at various slider positions. When the slider 3042 is moved by the operator, the window aligns with and shows the appropriate symbol printed or molded onto the insertion device housing or another insertion device component corresponding to a configuration of the IUD and/or IUD and insertion device at a corresponding procedural step.

VI. Pre-Insertion IUD Loading

Figure 31A:
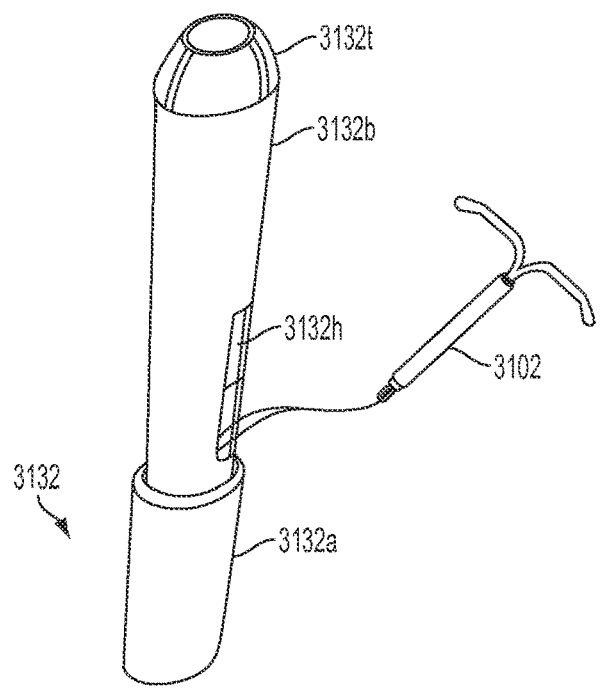
FIGS. 31A-31B illustrate features of the insertion device sheath, including IUD loading features and methods.
Figure 31B:
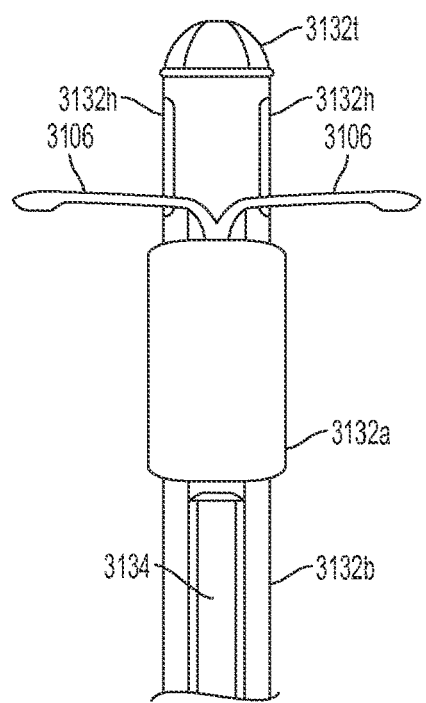

The present disclosure includes various features for preparing the insertion device for the IUD insertion procedure, as well as related methods. For example, the IUD 3102 which has arms 3106 can be loaded into the housing or sheath 3132 through one or more openings 3132*h* in the tip 3132*t* of the insertion device sheath, including an outer sheath 3132*a* or an inner sheath 3132*b*, as illustrated in FIGS. 31A-31B. The plunger 3134 is positioned within the sheath 3132 and engages the proximal end of the IUD 3132.

Figure 32A:
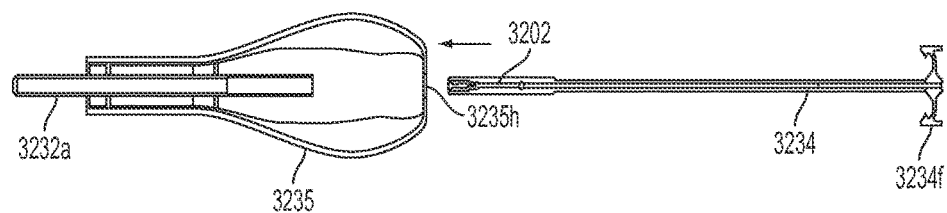
FIGS. 32A-32B illustrate IUD loading features and methods.
Figure 32B:
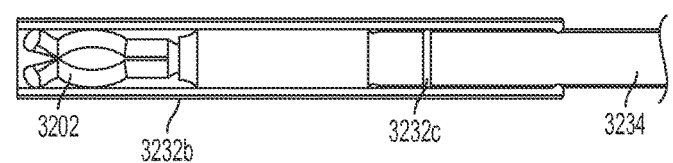

In additional aspects, as illustrated in FIG. 32A-32B, the IUD 3202 and plunger 3234 are simultaneously loaded into the insertion device through an opening 3235*h* in the insertion device housing 3235. The plunger 3234 is adaptable and configurable to include one or more features 3234*f* for attaching the plunger 3234 to the housing 3235 upon loading the plunger 3234 and IUD 3202 into the insertion device. As illustrated in FIG. 32B, the insertion device can further be adapted and configured to include a packing sleeve or inner sheath 3232*b* which provides a loading sheath to fold the IUD 3202 for loading into the insertion device. The packing sleeve or inner sheath 3232*b* can include one or more stopping features 3232*c* for stopping the packing sleeve 3232*b* from traveling into the outer sheath 3232*a* as the plunger 3234 is inserted through the housing and into the outer sheath. For example, the stopping feature 3232*c* is configurable to include a dimensional feature such as a protrusion which contacts a surface within the housing 3235 and prevents the packing sleeve from further movement. The IUD can be a T-shaped IUD, or any other IUD configuration, which is pre-packaged with the IUD arms in the extended position. The packing sleeve can be slid over the IUD prior to IUD loading to fold the IUD arms together for loading into the insertion device.

In another aspect, the handle or housing top and bottom pieces can be separated or opened to allow for loading of the plunger and IUD. For example, the housing can include a hinge which allows the housing to swing open for IUD loading.

In still another aspect of the present disclosure, the sheath or plunger position control features allow movement of the sheath or plunger to load the IUD into the sheath for insertion. For example, the IUD can be loaded into the insertion device sheath by advancing the sheath distal to cover the IUD prior to insertion. The insertion device can include a sheath slider located in a second middle position along the elongated guide prior to IUD insertion. While the IUD is locked to the plunger or housing, the slider is moved distal to advance the sheath distal and cover the IUD arms. Then, the insertion procedure is started with the sheath slider the first distal position. Step 2 of the insertion procedure involves moving the sheath slider backward to the second middle position, and step 3 involves moving the sheath slider backward to the third proximal position along the elongated guide.

While various aspects of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary aspects, but should be defined only in accordance with the following claims and their equivalents. As will be understood by persons of skill in the art, any of the foregoing device or process components can be used in any suitable combination to form the insertion device of the present disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An insertion device for inserting an IUD comprising:
   an elongated sheath having a proximal end and a distal end, a lumen extending between the proximal end and the distal end wherein the elongated sheath defines an axis for operation of the insertion device and wherein the IUD is positionable within the elongated sheath at the distal end of the elongated sheath;
   an elongated inner member having a proximal end and a distal end disposable within the lumen of the elongated sheath wherein a proximal end of the IUD is positionable adjacent the distal end of the elongated inner member;
   a proximally positioned user interface, wherein the proximally positioned user interface further comprises one or more elongated guides formed at least partially therein and along at least a portion of a length thereof wherein the one or more elongated guides are one or more elongated channels formed in an exterior surface of the proximally positioned user interface; and
   a moveable sheath slider having a proximal end, a distal end, and a curved surface wherein the moveable sheath slider is configured to move proximally or distally along the axis within the one or more channels formed in the exterior surface of the user interface in communication with the elongated sheath wherein the moveable sheath slider controls axial movement of the elongated sheath along the axis;
   a string control slider having a curved distal surface for abutting with the curved surface of the moveable sheath slider when the sheath slider is adjacent the string control slider; and
   a string aperture positioned proximally on the user interface,
   wherein the elongated guide further comprises one or more of at least one of soft motion control features along the length of the one or more channels formed in the exterior surface of the user interface wherein the one or more soft motion control features provides tactile feedback to a user when the moveable sheath slider moves from a first position along the length of the one or more channels to a second position along the length of the one or more channels corresponding to a location for a soft motion control.

2. The insertion device of claim 1, wherein the one or more elongated guides have a length, a width and a depth, and further wherein the elongated guide width is at least one of a variable length along and a staged width selected from two or more of a first width and a second width.

3. The insertion device of claim 1, wherein the one or more elongated guides have an in-plane profile selected from rectangular, s-shaped, c-shaped, u-shaped, w-shaped, circular, semi-circular, and oval.

4. The insertion device of claim 1, wherein the sheath slider comprises one or more surface profiles adapted and configured to mechanically complement the one or more motion control features.

5. The insertion device of claim 4, wherein the one or more surface profiles of the sheath slider are selected from the group comprising one or more of each of non-planar surfaces, curved surfaces, and angled surfaces.

6. The insertion device of claim 1, wherein the proximally positioned user interface and the sheath slider further comprises one or more alignment surfaces, wherein the one or more alignment surfaces of the user interface is adapted and configured to mechanically complement the one or more alignment surfaces of the sheath.

7. The insertion device of claim 6 wherein a first sheath slider alignment surface aligns with a first user interface alignment surface at a first position along a length of the one or more elongated guides.

8. The insertion device of claim 6, wherein the one or more sheath slider alignment surfaces and the one or more user interface alignment surfaces are selected from the group comprising a curved surface, an angled surface, a tilted surface and a dimensional surface.

9. The insertion device of claim 1, wherein the one or more elongated guides further comprises one or more cavities on one or more of the proximal end of the elongated guide and the distal end of the elongated guide wherein the one or more cavities are adapted and configured to house at least a portion of the movable sheath slider.

10. The insertion device of claim 1, wherein the string control slider is adaptable and configurable to securely move within the one or more elongated guides.

11. The insertion device of claim 1, wherein the moveable sheath slider and the string control slider are adapted and configured to operate at least one of simultaneously and independently within the one or more elongated guides.

12. The insertion device of claim 1, wherein the sheath slider and the string control slider are telescopically movable along at least a first portion of the one or more elongated guides, and further wherein the sheath slider and the string control slider are configurable such that at least one of the sheath slider and the string slider partially surrounds the remaining slider.

13. The insertion device of claim 1, wherein the sheath slider and string control slider are further configurable to comprise one or more vertical surfaces, wherein the one or more vertical surfaces are selected from the group comprising a first sheath slider vertical surface, a second sheath slider vertical surface, a first string control slider vertical surface, and a second string control vertical surface, wherein one or more of the vertical surfaces are configured to form an aligned adjacent surface at one or more positions along a length of the one or more elongated guides.

14. The insertion device of claim 1, wherein the sheath slider and the string control slider have a combined width less than or equal to at least one of 0.75 inches (19 mm), 0.7 inches (17.8 mm), 0.5 inches (12.7 mm), 0.35 inches (8.9 mm), or 0.25 inches (6.3 mm).

15. The insertion device of claim 1, wherein the insertion device is configurable to receive the IUD within a distal end of the lumen of the elongated sheath and wherein the insertion device further comprises at least one string locking feature adaptable and configurable to secure one or more string components of the IUD.

16. The insertion device of claim 15, wherein the at least one string locking feature comprises one or more of a cleft, a clamp, a wedge, a pincher, a spring, or teeth.

17. The insertion device of claim 16, wherein the string locking feature comprises a cleft, and the string locking feature comprises a movable member which pushes the one or more strings out of the cleft to unlock the one or more strings.

18. The insertion device of claim 1, wherein the distal end of the elongated sheath has an atraumatic tip selected from the group comprising a rounded tip and a tapered tip.

19. The insertion device of claim 18, wherein the distal end of the elongated sheath has an outer diameter of about 3 mm to 5 mm.

20. The insertion device of claim 18, wherein the distal end of the elongated sheath has an outer diameter which is equal to or less than 80%, 50%, 30% of the outer diameter of the proximal end of the elongated sheath.

21. The insertion device of claim 18, wherein the distal end of the elongated sheath has an outer diameter which is less than a maximum cross-sectional dimension of the IUD positionable within the lumen of the elongated sheath.

22. The insertion device of claim 18, wherein the distal end of the elongated sheath further comprises one or more slits or flaps at a forward end of the sheath.

23. The insertion device of claim 1 further comprising one or more feedback mechanisms selected from the group comprising audible, visible, and tactile.

24. The insertion device of claim 1 wherein an elongate member of the IUD comprises a core part around which a jacket-like polymeric reservoir containing an active agent has been fitted.

25. The insertion device of claim 24 wherein the active agent is a hormone used for the treatment of menopausal troubles or for contraception.

26. The insertion device of claim 1 wherein the IUD includes an active agent that is a hormone used for treatment of menopausal troubles or for contraception.

* * * * *